United States Patent

Stephens et al.

[11] Patent Number: 5,750,342
[45] Date of Patent: May 12, 1998

[54] NUCLEIC ACID LIGANDS OF TISSUE TARGET

[75] Inventors: Andrew Stephens, Denver; Dan Schneider; Larry Gold, both of Boulder, all of Colo.; Ulrich Speck, Berlin, Germany

[73] Assignees: NeXstar Pharmaceuticals, Inc., Boulder, Colo.; Schering Akiengesellschaft, Berlin, Germany

[21] Appl. No.: 433,124

[22] Filed: May 3, 1995

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and Ser. No. 964,624, Oct. 21, 1992, Pat. No. 5,496,938.

[51] Int. Cl.$^6$ ............ C12Q 19/34; C12Q 1/68; C07H 21/02; C07H 21/04
[52] U.S. Cl. ............ 435/6; 435/91.2; 536/23.1; 536/25.4; 935/77; 935/78
[58] Field of Search ............ 435/6, 91.2; 935/77, 935/78; 536/25.4, 23.1

[56] References Cited

FOREIGN PATENT DOCUMENTS

| 2 183 661 | 6/1987 | United Kingdom . |
|---|---|---|
| WO 89/06694 | 7/1989 | WIPO . |
| WO 94/06934 | 3/1994 | WIPO . |

OTHER PUBLICATIONS

Davis et al. (1978) The Lancet 1:1185.
Davis et al. (1980) Circulation 61:982.
Fischman et al. (1989) J. Nucl. Med. 30:1095.
Ginsberg et al. (1990) Arteriosclerosis 10:256.
Isaacsohn et al. (1986) Metabolism 35:364.
Lees et al. (1983) J. Nucl. Med. 24:154.
Lees et al. (1988) Arteriosclerosis 8:461.
Mettinger et al. (1978) The Lancet 1:242.
Minar et al. (1989) Stroke 20:27.
Moerlein et al. (1991) J. Nuc. Med. 32:300.
Ord et al. (1992) Circulation 85:288.
Roberts et al. (1983) J. Lipid Research 24:1160.
Tsai and Keene (1993) J. Immunol. 150:1137.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

This invention discloses high-affinity oligonucleotide ligands to complex tissue targets, specifically nucleic acid ligands having the ability to bind to complex tissue targets, and the methods for obtaining such ligands. Tissue targets comprise cells, subcellular components, aggregates or cells, collections of cells, and higher ordered structures. Specifically, nucleic acid ligands to peripheral blood mononuclear cells (PBMC), fibrin clots, and carotid arteries are described.

7 Claims, 1 Drawing Sheet

Carotid SELEX-Schematic

NUCLEIC ACID LIGANDS OF TISSUE TARGET

RELATED APPLICATIONS

This application is a Continuation-in-Part of U.S. patent application Ser. No. 07/714,131, filed Jun. 10, 1991, entitled "Nucleic Acid Ligands"(now U.S. Pat. No. 5,475,096), which is a Continuation-in Part of U.S. patent application Ser. No. 07/536,428, filed Jun. 11, 1990, entitled "Systematic Evolution of Ligands by Exponential Enrichment", now abandoned, and U.S. patent application Ser. No. 07/964,624, filed Oct. 21, 1992, entitled "Methods of Producing Nucleic Acid Ligands" (now U.S. Pat. No. 5,496,938).

FIELD OF THE INVENTION

Described herein are methods for identifying and preparing nucleic acid ligands to tissues. Tissues are described herein as a collection of macromolecules in a heterogeneous environment. According to this definition, tissues encompass a single cell type, a collection of cell types, an aggregate of cells or an aggregate of macromolecules. The method utilized herein for identifying such nucleic acid ligands is called SELEX, an acronym for Systematic Evolution of Ligands by EXponential enrichment. Specifically disclosed herein are high-affinity nucleic acid ligands which bind to various tissues.

BACKGROUND OF THE INVENTION

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands" (now U.S. Pat. No. 5,475,096), U.S. patent application Ser. No. 07/931,473, filed Aug. 17, 1992, entitled "Nucleic Acid Ligands", now U.S. Pat. No. 5,270,163 (see also WO 91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", describes the use of SELEX in conjunction with gel electrophoresis to select nucleic acid molecules with specific structural characteristics, such as bent DNA. U.S. patent application Ser. No. 08/123,935, filed Sept. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands" (now U.S. Pat. No. 5,496,938) describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX", describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sept. 8, 1993, entitled "High Affinity Nucleic Acid Ligands Containing Modified Nucleotides", that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Without question, the SELEX process is very powerful. However, to date the process has been successfully demonstrated primarily with pure, simple targets, such as proteins or small molecules. The present invention provides the first demonstration that complex targets are also compatible with the SELEX process.

It is desirable to be able to obtain nucleic acid ligands to complex tissue targets for various reasons. First, tissue SELEX can be useful to obtain nucleic acid ligands when a distinct target is unknown but a general mode of action of the desired ligand is suggested. Second, tissue SELEX can be useful when nucleic acid ligands are desired based on functional results. Third, it can be desirable to obtain nucleic acid ligands to a complex tissue target when it is unclear which single target would be effective. It is also useful to obtain nucleic acid ligands to a complex tissue target if the purified target is unavailable or unstable in its purified form (i.e., a membrane protein).

BRIEF SUMMARY OF THE INVENTION

The present invention includes methods of identifying and producing nucleic acid ligands to complex targets such as tissues and the nucleic acid ligands so identified and produced. More particularly, nucleic acid ligands are provided that are capable of binding specifically to tissues which are macromolecules in a heterogeneous environment, such as whole cells or substructures thereof, aggregates of cells, collections of cells, aggregates of macromolecules and the like.

Further included in this invention is a method of identifying nucleic acid ligands to tissues comprising the steps of (a) preparing a candidate mixture of nucleic acids, (b) partitioning between members of said candidate mixture on the basis of affinity to tissue, and (c) amplifying the selected molecules to yield a mixture of nucleic acids enriched for nucleic acid sequences with a relatively higher affinity for binding to tissue. Also included are nucleic acid ligands identified according to such method.

Another embodiment of the invention includes methods wherein a negative selection is performed in order to perfect the discrimination between subtle differences of similar tissue types. In this embodiment, the resulting ligands are specific not only for a particular tissue type, but can discriminate between subtly different tissues of the same type. For example, this method can discriminate between normal and abnormal tissue types, between induced and uninduced tissue types, etc.

In another embodiment of the invention, a method is provided for identifying previously unknown or uncharacterized epitopes which are components of a larger unknown macromolecule on the tissue target. The ligands that are evolved by the present invention are capable of binding to previously unknown epitopes and the macromolecule which comprises the unknown epitope can then be identified by standard methods. For example, ligands can be evolved to a previously unknown protein found in the context of a complex tissue target. The ligand of the invention can be used to purify the protein away from the tissue target by standard protein purification and identification methods. These standard methods include affinity purification, microsequencing and cDNA databank searches. In this aspect, the newly identified epitopes which are components of a larger unknown macromolecule, such as new or previously uncharacterized proteins, are provided by the invention. These new epitopes and the macromolecules of which they are a component will be useful as diagnostic and therapeutic agents as well as the ligands that helped identify them.

More specifically, the present invention includes nucleic acid ligands to peripheral blood mononuclear cells (PBMC), clots and restenotic arterial cells, including those ligands shown in Tables 2, 5, and 8, respectively. Also included are nucleic acid ligands to the above-described tissues that are substantially homologous to any of the given ligands and that have substantially the same ability to bind the above-described tissues. Further included in this invention are nucleic acid ligands to the above-described tissues that have substantially the same structural form as the ligands presented herein.

DETAILED DESCRIPTION OF THE INVENTION

Figure 1:
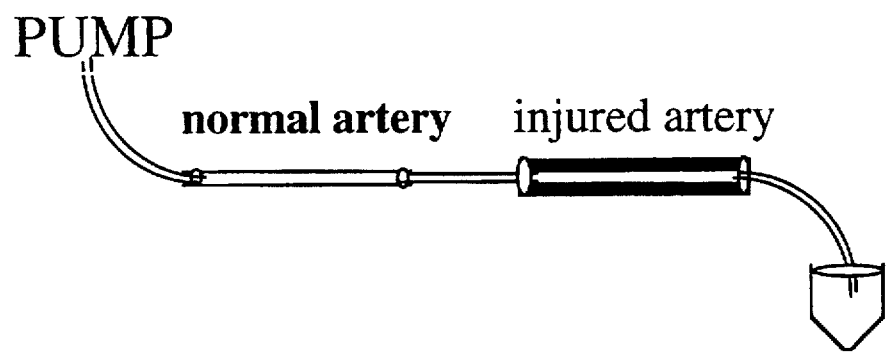
FIG. 1 shows a schematic representation used in the carotid artery SELEX procedures.

This application describes nucleic acid ligands to complex tissue targets identified generally according to the method known as SELEX. As stated earlier, the SELEX technology is described in detail, in the SELEX Patent Applications which are incorporated herein by reference. This method, referred to as Tissue SELEX, incorporates complex targets in contrast to the more simple targets previously used in the SELEX process. Certain terms used to describe the invention herein are defined as follows:

"SELEX" methodology refers to the combination of selection of nucleic acid ligands which interact with a target in a desirable manner, for example binding to a protein, with amplification of those selected nucleic acids as described in detail above and in the SELEX Patent Applications. Iterative cycling of the selection/amplification steps allows selection of one or a small number of nucleic acids which interact most strongly with the target from a pool which contains a very large number of nucleic acids. Cycling of the selection/ amplification procedure is continued until a selected goal is achieved.

"Tissue SELEX" methodology applies the SELEX methodology to tissue targets. Tissue SELEX has several advantages. First, using Tissue SELEX one can obtain ligands to specific cell types in the absence of a defined understanding of the involved epitope. The epitope against which a ligand is evolved is usually a substructural component of a larger macromolecule. The ligands found by this method could also be useful in identifying new proteins or other new macromolecules on the tissue target. The new proteins or other new macromolecules which comprise a newly identified epitope can be purified and characterized using standard procedures. Second, ligands can be obtained to defined epitopes or macromolecules in the context of their physiologic cellular or membrane environment. Third, it is possible to obtain ligands to tissues in a functionally altered phenotype, e.g., activated, migrating, etc. The ligands and the new macromolecules containing the ligand epitopes identified by this process may be useful as diagnostics or therapeutics.

Tissue SELEX is a powerful methodology which allows one to identify nucleic acid ligands that can mediate many different cell behaviors, such as apoptosis, anergy, differentiation, proliferation, etc., without prior knowledge of the identity of the specific tissue targets that control these changes. The sensitivity of the SELEX process may lead to the generation of oligonucleotides that recognize potentially every different epitope on the complex tissue target. Larger numbers of different sequence motifs are expected using the tissue SELEX process, as compared with simple-target SELEX, since it is believed that different motifs will recognize distinct epitopes on the complex tissue target. Some epitopes may lie within the same protein, but many will be directed to various proteins or other molecules on the tissue. Tissue SELEX can be done in vivo or in vitro.

In one embodiment, a negative selection process (termed counter-SELEX) is employed to enhance the possibility that the ligands derived by tissue SELEX have precise specificity and affinity. In this embodiment, ligands are selected for a specific tissue and then a negative selection is done against a related tissue which does not have certain characteristics for which the ligand is desired. The negative selection can be done against a similar cell line or cell type, different cells, normal tissue, plasma or blood, a non-specific antibody or other available ligand. An example of this negative selection would be to first select using a tumor cell target(such as a malignant melanoma) and then counterselect the resulting nucleic acids against a similar cell type which is not tumorogenic (such as normal human melanocytes). Ligands that interact with both normal and neoplastic tissue will be removed by this negative selection and only those nucleic acid ligands that specifically bind the tumor cells will be identified (or retained). The resulting nucleic acid ligand would be specific for tumors. This technique will provide the ability to identify nucleic acid ligands that can discriminate between two closely related targets, i.e., between a cancerous cell and an untransformed cell of the same tissue type. The negative selection can also be done in vivo. Using this method one can not only generate ligands to specific targets on complex tissue surfaces, but also be able to recognize the differences between normal and abnormal tissue of a particular type.

"SELEX Target" or "Target" refers to any compound upon which a nucleic acid can act in a predetermined desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, etc., without limitation. Virtually any chemical or biological effector would be a suitable SELEX target. Molecules of any size can serve as SELEX targets. A target can also be modified in certain ways to enhance the likelihood of an interaction between the target and the nucleic acid.

"Tissue target" or "Tissue" refers to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the preferred embodiment, tissues are insoluble macromolecules which are orders of magnitude larger than simpler SELEX targets. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue, and muscle tissue.

Examples of tissues which fall within this definition include, but are not limited to, heterogeneous aggregates of macromolecules such as fibrin clots which are acellular; homogeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. Virtually any modification of the nucleic acid is contemplated by this invention.

"Nucleic acid test mixture" or "nucleic acid candidate mixture" is a mixture of nucleic acids of differing, randomized sequence. The source of a "nucleic acid test mixture" can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process. The length of the randomized section of the nucleic acid is generally between 8 and 250 nucleotides, preferably between 8 and 60 nucleotides.

"Nucleic acid ligand" is a nucleic acid which has been isolated from the nucleic acid candidate mixture that acts on a target in a desirable manner. Examples of actions on a target in a desirable manner include, but are not limited to binding of the target, catalytically changing the target, reacting with the target in a way which modifies/alters the target or the functional activity of the target, covalently attaching to the target as in a suicide inhibitor, facilitating the reaction between the target and another molecule. In most, but not all, instances this desirable manner is binding to the target. In the most preferred embodiment, a nucleic acid ligand is a non-naturally occurring nucleic acid ligand having a specific binding affinity for a tissue target molecule, such target molecule being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by the target molecule. Nucleic acid ligand includes nucleic acid sequences that are substantially homologous to the nucleic acid ligands actually isolated by the Tissue SELEX procedures. By substantially homologous it is meant a degree of primary sequence homology in excess of 70%, most preferably in excess of 80%. In the past it has been shown that the sequence homologies of various nucleic acid ligands to a specific target shows that sequences with little or no primary homology may have substantially the same ability to bind the target. For these reasons, this invention also includes nucleic acid ligands that have substantially the same ability to bind a target as the nucleic acid ligands identified by the Tissue SELEX process. Substantially the same ability to bind a target means that the affinity is within a few orders of magnitude of the affinity of the ligands described herein. It is well within the skill of those of ordinary skill in the art to determine whether a given sequence—substantially homologous to those specifically described herein—has substantially the same ability to bind a tissue target.

"Partitioning" means any process for separating nucleic acid ligands from the remainder of the unreacted nucleic acid candidate mixture. Partitioning can be accomplished by various methods known in the art. Filter binding, affinity chromatography, liquid-liquid partitioning, filtration, gel shift, density gradient centrifugation are all examples of suitable partitioning methods. Equilibrium partitioning methods can also be used as described in detail below. Since the tissue targets of the present invention are non-soluble, there are numerous simple partitioning methods which are well suited to this invention. The simple partitioning methods include any method for separating a solid from a liquid, such as, centrifugation with and without oils, membrane separations and simply washing the insoluble tissue target. The ligands can also be specifically eluted from the target with a specific antibody or ligand. The choice of partitioning method will depend on properties of the target and the nucleic acid and can be made according to principles and properties known to those of ordinary skill in the art.

"Amplifying" means any process or combination of process steps that increases the amount or number of copies of a molecule or class of molecules. In preferred embodiments, amplification occurs after members of the test mixture have been partitioned, and it is the facilitating nucleic acid associated with a desirable product that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplication can be made after each round of amplification, if necessary.

"Randomized" is a term used to describe a segment of a nucleic acid having, in principle, any possible sequence over a given length. Randomized sequences will be of various lengths, as desired, ranging from about eight to more than one hundred nucleotides. The chemical or enzymatic reactions by which random sequence segments are made may not yield mathematically random sequences due to unknown biases or nucleotide preferences that may exist. The term. "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into a randomized sequence, for example, by altering the molar ratios of precursor nucleoside (or deoxynucleoside) triphosphates in the synthesis reaction or the ratio of phosphoramidites in the chemical synthesis. A deliberate bias may be desired, for example, to affect secondary structure, to introduce bias toward molecules known to have facilitating activity, to introduce certain structural characteristics, or based on preliminary results.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to more complicated tissue targets.

Negative selection (Counter-SELEX) is optionally employed before, during or after the Tissue SELEX process. The negative selection provides the ability to discriminate between closely related but different tissue types. For example, negative selection can be introduced to identify nucleic acid ligands that have a high specificity for a tumor cell but do not recognize the cognate normal tissue. Similarly, nucleic acid ligands can be identified which specifically recognize atherosclerotic arterial tissue but not normal arterial tissue. Nucleic acid ligands which recognize fibrin, but not fibrinogen can also be identified by this method. Additionally, nucleic acid ligands to a cell type which express a certain receptor can be counter-selected with a cell line engineered not to express the receptor (or other such macromolecule).

One of ordinary skill in the art will readily understand that various mechanisms can be employed to accomplish this negative selection. The following examples are provided mostly for illustrative purposes and are not meant in any way as limiting the procedures of negative selection. Negative selection or Counter-SELEX methods were first described in U.S. patent application Ser. No. 08/134,028, filed Oct. 7, 1993, entitled "High-Affinity Nucleic Acid Ligands that Discriminate Between Theophylline and Caffeine", which is herein incorporated by reference. A particular implementation of negative selection is embodied using equilibrium partitioning. In this method, two cell lines or other tissue types are separated by a semi-permeable membrane (0.45–0.90 µm pore size) in an equilibrium dialysis chamber; one cell line is the neoplastic target cell line, the other, the normal tissue used for the negative selection. The choice of cell or tissue type for the negative selection will be determined by the specific end results desired and will sometimes consist of a non-malignant cell line of the same tissue type as the neoplastic target. For other experiments, various normal cell types could be combined to create the negative epitope "sink." The random pool of nucleic acids is placed into the dialysis chamber (on the side of the normal cells; this avoids background from high avidity targets which are common to both the tumor and normal cells) and allowed to equilibrate between the two cell lines. Those nucleic acid sequences that remain bound to the target cell line or tissue at equilibrium are selectively recovered and amplified for the next round of SELEX.

This example of negative selection methodology is quite powerful. First, equilibrium dialysis negative selection allows the positive and negative selection to be carried out simultaneously. Second, the stringency of the negative selection can be varied through the alteration of the relative amounts of "positive" and "negative" cells placed on each side of the dialysis membrane. These two characteristics of equilibrium dialysis negative selection allow precise control over the evolution of nucleic acid ligands specific for the target cell or tissue type.

This same type of equilibrium partitioning negative selection can be carried out with adherent cell lines. In this embodiment, monolayers of target and negative cells or tissues are plated in different wells of a multi-welled plate. After adherence, media, along with an oligonucleotide pool, is added such that the wells are connected by the volume of cell media. After equilibration of the oligonucleotide pool, those sequences bound by the target cell line or tissue type would be isolated and amplified for the next round of SELEX.

The equilibrium negative selection strategies above offer a powerful way of generating nucleic acid ligands to tissue targets and especially tumor associated antigens (TAAs).

Additionally, there are several other negative selection methods, which could be classified as "post-SELEX screening procedures." The most simple of these procedures is the testing of individual nucleic acid ligands (those sequences generated by tissue SELEX and demonstrated to be high-affinity ligands for the tissue target) against normal tissue for cross-reactivity. However, this approach is a tedious and time-consuming process.

A more fruitful "post-SELEX" method is to perform a negative selection, for example using a normal tissue as the negative selection target, on a pool that has already been evolved from a SELEX against a desirable complex tissue target, for example a transformed cell line. This example would suggest the performance of two to three negative selections on a normal tissue using a late-round, highly evolved pool from a SELEX of a transformed cell line. The binding of certain sequences to the normal tissue would be used to subtract these sequences from the evolved pool. This method allows one to quickly eliminate from several hundred to several thousand nucleic acid sequences that show a high affinity for those targets common to both the normal and the transformed cell lines.

Another "post-SELEX" screening method is a variation of a photocrosslinking experiment. As an example, it is possible to synthetically incorporate a highly photoreactive nitrine group (which is also iodinatable) on the 5' end of a PCR primer used in the tissue SELEX protocols. Late-round pools from for example, a tumor cell line SELEX would be amplified with this photoactivatable (and $^{125}$I-labeled) primer, and this sequence pool would then be irradiated in the presence of the tumor cell line, and in the presence of normal tissue. Membrane proteins would be isolated and solubilized for analysis on an SDS gel. One would expect to see many different protein epitopes tagged by specific oligonucleotide sequences, for both the tumor and the normal cell lines. A few tagged targets will be unique to the tumor cell line. Because the oligonucleotides have been photochemically linked to the protein targets in a manner which does not destroy the base sequence of the oligonucleotide, it is possible to isolate a tumor-specific band from an SDS gel, and use PCR to recover a specific sequence motif that recognizes a particular tumor antigen. Thus, in one step, it will be possible to remove from a pool oligonucleotide sequences that recognize possibly hundreds of cell surface antigens, leaving one or a few families of sequences that binds specifically to a single tumor-specific antigen.

As described above, the Tissue SELEX methods can include the identification of macromolecules which comprise new epitopes on the tissue target. The nucleic acid ligand to the new epitope component of the macromolecule can be employed to purify, identify and characterize the macromolecule. The new macromolecule can be a previously unknown protein or peptide, lipid, carbohydrate, etc. Virtually any molecule that is part of the molecular make-up of a tissue can be identified by the Tissue SELEX process.

In order to fully exploit this aspect of the invention, it is important to develop strategies for the purification and identification of new macromolecules which comprise the new epitopes and to determine the roles these new macromolecular components of the tissue play in biological systems. The methods for purifying new macromolecules are well-known, especially in the art of protein purification. These standard purification methods include crosslinking, affinity chromatography, peptide microsequencing, Edman sequencing, mass spectrometry, and cDNA library searches.

The following discussion describes this process as it would be applied to the identification of a new tumor-associated antigen (TAA). For the purposes of this discussion, a TAA is a macromolecule that is expressed on a tumor cell, but not on a similar normal cell. A TAA may or may not be immunogenic. A TAA is merely one example of the kind of macromolecules which can be identified by the Tissue SELEX process and simply used for illustrative purposes. However, it is readily apparent that this process can be extrapolated to any new macromolecule identified by the Tissue SELEX process.

As applied to TAAs, the identification of new TAAs by the Tissue SELEX process is composed of two main parts: one, developing strategies for the purification and identification of new TAAs, and two, the elucidation of the role these tumor antigens play in cancer (i.e., determining the biological significance of each particular TAA in the development and progression of a particular cancer).

The steps of purification and identification of most of the TAAs should be straightforward and understood by one skilled in the art of protein purification. As with antibodies, SELEX provides a reagent—a high-affinity ligand specific for the tumor antigen—that is incredibly useful for the purification of the antigen from whole cells or other tissues. As a non-limiting example, most antigens will be amenable to some type of photo-affinity crosslinking or in the negative selection strategies section above. Specific crosslinking of the TAA, using a photoactivatable oligonucleotide with a 3' biotin conjugate will allow one-pass purification of the TAA target using streptavidin coated beads. An alternative method to this purification strategy is to use a column-bound high-affinity nucleic acid ligand to affinity purify the TAA target from solubilized target cell membrane preparations.

There are many compelling reasons to believe that the method provided herein for identifying macromolecules that comprise new epitopes on tissues offers distinct advantages over traditional methods of new macromolecule discovery. Again, the following discussion will be directed to tumor-associated antigen discovery, but one will readily understand that it can be broadly extrapolated to all new macromolecule discovery.

As applied to tumor-associated antigens, one must fully consider that all that is known about tumor antigens has been derived from the immune system's reaction to particular antigens; science has depended on the particular restrictions of the immune system, and the system's repertoires to distinguish antigenic differences between neoplastic and normal tissue. It is entirely possible that other tumor antigens exist that are not subject to immune response. Some investigators have hypothesized that there may in fact be many antigenic differences between cancer and normal tissue, which are, unfortunately, not immunogenic.

The SELEX methodology provides an improved way to identify TAAs that avoids the restrictions posed by the immune system:

a. SELEX can actually provide a deeper search of TAAs than can the entire potential antibody repertoire of an organism—the size of the nucleic acid libraries used in SELEX is unrivaled by any biological system;

b. SELEX provides nucleic acid ligands to targets, including those which are not antigenic to the immune system because of tolerance. Many of the TAAs which have been identified are oncofetal—they are antigens expressed at some point during development or cell differentiation. As prior "self" antigens, they elicit no overt immune response because of earlier immune system tolerization. A SELEX-based search for TAAs avoids the circular nature of using the immune system as a means of identifying tumor antigens;

c. SELEX nucleic acid ligands have been shown to be exquisitely sensitive to target conformation. While most antibodies recognize conformational, or discontinuous eptitopes, antibody functional epitopes are composed of only a few amino acids. The potential binding surface of an oligonucleotide ligand is much larger than that of an antibody variable region, and may provide greater conformational discrimination of large targets. Additionally, cross-reactivity for SELEX ligands is substantially less of a problem than for monoclonal antibodies. A considerable set of restrictions also controls T-cell mediated tumor responses. These immune system limitations provide important biological functions; however, they limit the immune system's power for TAA identification.

d. SELEX is possibly more sensitive to small quantities of antigen than the immune system. Although the immune system's threshold for reactivity has been estimated to be 200 copies/cell for an antigenic MHC-presented peptide, a B-cell antibody response (necessary for any antigen that is not a peptide-carbohydrates, lipids or conformational antigens) to a monovalent target requires antigen concentrations of about 100 mM. SELEX can generate ligands to TAA targets with a low representation on the cell surface; and e. SELEX provides a rapid and thorough method of TAA discovery. Screening of monoclonal antibodies to tissue sections, and purification and identification of MHC peptides are painstaking processes that set practical limits on the depth and completeness of searches for TAAs. Tissue SELEX experiments take a much abbreviated length of time.

Nucleic acid ligands to tissue targets or the tissue epitopes identified by the method of the invention are useful as diagnostic reagents and as pharmaceuticals. The nucleic acid ligands are also useful for the identification of new macromolecules. The nucleic acid ligands are useful in any application that would be suitable for use of an antibody.

As diagnostic reagents, the ligands or tissue epitopes can be used in both in vitro diagnostics and in vivo imaging applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek for a diagnostic ligand. Details regarding use of the ligands in diagnostic applications is well known to one of ordinary skill in the art. Nucleic acid ligands that bind specifically to pathological tissues such as tumors may have a role in imaging pathological conditions such as human tumor imaging and even therapeutic delivery of cytotoxic compounds or immune enhancing substances.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labelling tag in order to track the presence of a ligand. Such a tag could be used in a number of diagnostic procedures.

Specifically, oligonucleotide ligands with high specificity for particular tumor antigens could become as important as monoclonal antibodies for the detection, imaging, and surveillance of cancer. Modified nucleic acid ligands show nuclease resistance in plasma, and the use of 5' and 3' capping structures will provide stability in animals that rivals that of monoclonal antibodies (and without the immunogenicity of animal-derived MAbs). Radionuclides, magnetic compounds, and the like can be conjugated to tumor-specific oligonucleotides for cancer imaging. SELEX tumor ligands can also be used to determine if these tumor antigens are sloughed off tumors, and are detectable in the plasma like PSA.

The nucleic acid ligands to tissue targets or newly identified macromolecules components of tissue are also useful as pharmaceuticals. Therapeutic uses include the treatment or prevention of diseases or medical conditions in human patients. Therapeutic uses also include veterinary applications. The ligands can bind to receptors and be useful as receptor antagonists. Conversely, under certain circumstances the ligands can bind to receptors and cause receptor capping and act as receptor agonists.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

Standard formulations can be used for the nucleic acid ligands of the invention and are known to one of ordinary skill in the art.

The following examples provide a non-limiting description of the present invention. Example One describes obtaining ssDNA ligands to the complex tissue target peripheral blood mononuclear cells (PBMC). Ligands to PBMC have many uses including imaging lymph nodes for cancer screening and flow cytometry uses for AIDS monitoring.

Example Two describes the ability to obtain RNA ligands to human fibrin clots. The pyrimidine residues of these RNA ligands have been modified with flourine at the 2'-position of the sugar. The fibrin ligands are useful as diagnostic agents as described below.

Circulating fibrinogen is cleaved to insoluble fibrin by the actions of the common product of the intrinsic and extrinsic coagulation cascade, thrombin. Fibrin provides a fibrous network for the clot allowing platelet deposition and later fibroblast invasion. Fibrin is present in large amounts in all thrombi, relatively less in platelet-rich arterial clots than fibrin-rich venous clots. Fibrin also can provide the nidus for atherosclerotic plaques and restenotic lesions by harboring thrombin and other mitogens which can lead to endothelial activation and smooth muscle cell proliferation.

The noninvasive detection and localization of thrombi remains a major challenge in clinical diagnosis. Deep vein thrombosis (DVT) and pulmonary embolism (PE) carry with them a high rate of mortality and morbidity. Deep-vein thrombosis (DVT) is a major complication of hospitalization and is diagnosed by physical exam less than one third of the time. Patients at risk include those with a major medical illness, malignancy, undergoing general abdominal, thoracic surgery or major orthopaedic surgery. High risk patients carry a 40–80% risk of DVT with a 1–2% risk of fatal pulmonary embolism (PE) (Weinmann, E. E. and Salzman, E. W. (1994) New Engl. J. Med. 331:1630–1641). PE accounts for 50,000 deaths/yr. 90% of PEs are non-fatal but carry significant morbidity: dyspnea, pulmonary infarction, abcess, or hypertension. 95% of PEs arise as a complication of DVT. Diagnosis of these conditions is difficult and has not improved, as noted by the high rate of undiagnosed PE on autopsy, which has not improved over time. Freiman et al. found evidence of subclinical PE in 64% of consecutive autopsies among persons with various causes of death (Freiman, D. G., Suyemoto, J. and Wessler, S., (1965) N. Engl. J. Med., 272, 1278–1280). Arterial thrombus, mostly secondary to atheromatosis, is even more difficult to diagnose non-invasively.

Non-invasive imaging of venous clots has relied on ultrasonic visualization of the deep venous system of the lower extremities. These studies are limited (generally only the thigh region) and are extremely operator dependent. PE diagnosis is generally done by ventilation and perfusion scanning using radioisotopes with the gold-standard being invasive pulmonary angiography. Radiolabeled fibrinogen has been used historically (Lensing, A. W. and Hirsh, J. (1993) Thromb Haemost (Germany) 69:2–7. It requires either prospective administration or thrombus extension after it becomes clinically apparent. A number of reports of radiolabeled antibodies to either fibrin or platelets have been reported. These are sensitive but slow, with adequate images appearing 12–48 hours after injection of the tracer. The need for delayed images is due to clearance of the unbound antibody from the vasculature to allow for adequate signal-to-noise ratio. No significant imaging of coronary artery disease has been reported. The conjecture is that the thickness of the blood pool in the left ventricle of the heart significantly obscures the signal from the small overlying epicardial coronary arteries. Arterial imaging has been performed on the larger vessels of the aorta or femoral arteries using either anti-fibrin or anti-platelet antibodies. Both antibodies have problems: the antifibrin Abs bind to epitopes that are poorly accessible and which are constantly changing through clot stabilization and fibrinolysis; the anti-platelet Abs bind to epitopes which exist in circulating blood, thereby increasing their background. Meaningful high resolution detection of disease in small arteries will require high specificity, rapid clearance of unbound material, and probably 3-dimensional tomographic imaging technologies. In many respects, RNA ligands are suitable agents for these diagnostic approaches. A superior non-invasive diagnostic test for pulmonary embolism would be particularly clinically relevant.

Example Three describes the ability to obtain RNA ligands to rat stenotic carotid arteries. The stenotic carotid arteries ligands are useful as diagnostic and pharmaceutical agents as described below.

Atherosclerosis is one of the major causes of mortality in the world. There has been much effort in identifying and targeting both therapeutics and diagnostic agents to this pathological tissue. Experimentally atherosclerosis suffers from the absence of ideal animal models. Rodent vessels are significantly different from the primate especially with respect to the neointima. Primate model are expensive. The pig or 'minipig' provides a model for restenosis but does not provide a good model of primary atherosclerosis. Recently, transgenic mouse models have become available, but they are still poorly defined.

Although mechanisms and components of atherosclerosis are not completely defined most investigators would agree that smooth muscle cells play an important role. The consensus is that these SMCs proliferate within the intima and are in some form 'activated'. The rat balloon-injured carotid artery model is one of the best understood models of response to arterial damage. Although there are limits to this model, there is clear evidence that in response to endothelial damage a proliferative response occurs primarily involving the SMCs. Many unique proteins have been identified from this tissue as well as signals responsible for SMC activation, migration and proliferation, as well as, extracellular matrix deposition. As such this remains a viable model of restenosis and less directly, primary atherosclerosis.

The rat balloon-injured carotid (RBIC) model provides a unique model for testing the hypothesis that nucleic acid ligands can be evolved by the SELEX methodology which is capable of recognizing pathological tissue to the exclusion of closely related normal tissue. RBIC are relatively well understood with respect to their composition and structure, are easily and reproducibly produced in a readily available lab animal, and have relevance to human pathologic conditions.

EXAMPLE ONE ssDNA Ligands to Peripheral Blood Mononuclear Cells (PBMC)

This example demonstrates the ability to obtain ssDNA ligands to the complex tissue target human peripheral blood mononuclear cells (PBMC). PBMC are isolated from whole blood as described below and contain a complex mixture of cell types including B-lymphocytes, T-lymphocytes and monocytes. Ligands to PBMC have many uses including imaging lymph nodes for cancer screening and flow cytometry uses for AIDS monitoring.

A. MATERIALS and METHODS

Isolation of PBMCs

Fresh human blood was collected in heparinized vacutainers and up to 35 ml of whole blood was layered atop 10 ml of ficoll (Sigma Histopaque-1077®) in a 50 ml polyethylene conical tube. The samples were centrifuged at 400×g for 30 minutes at room temperature to separate the blood into three layers: red blood cells (RBCs) below the ficoll, peripheral blood mononuclear cells (PBMCs, including B lymphocytes, T lymphocytes, and monocytes) immediately above the ficoll, and acellular plasma above the PBMCs. Following centrifugation, the plasma was aspirated with a pasteur pipet to within 0.5 cm of the opaque PBMC interface. The PBMC interface, also referred to as the "buffy coat", was transferred to a 15 ml conical tube with a pasteur pipet, 10 ml of phosphate buffered saline solution (PBS, 137 mM NaCl, 2.7 mM KCl, 10.1 mM $Na_2HPO_4$, 1.8 mM $KH_2PO_4$) was added, and the cells were washed by gentle aspiration. The cells were then centrifuged at 250×g for 10 minutes at room temperature and the supernatant aspirated and discarded. The cell pellet was resuspended in 5 ml PBS, mixed by gentle aspiration, centrifuged at 250×g for 10 minutes at room temperature, and the supernatant aspirated and discarded. This washing step was repeated a third time, and the cells were resuspended in a final volume of 0.3 ml PBS, transferred to a 1.7 ml eppendorf tube, and stored on ice. PBMC yield and viability were measured by diluting the cells 1:50 in PBS, adding an equal volume of 0.4% trypan blue, and counting viable cells with a hemocytometer. Typical yields were $10^6$ cells/ml of whole blood with >95% viability.

Generation of Degenerate ssDNA Library

A library of synthetic DNA oligonucleotides containing 40 random nucleotides flanked by invariant primer annealing sites (oligonucleotide 1, 5'-AGGGAGGAC GATGCGG-$[N]_{40}$-CAGACGACTCGCCCGA-3') (SEQ ID NO: 1) was amplified by the Polymerase Chain Reaction (PCR) for three cycles using oligonucleotides 2 (5'-AGGGAGGACGATGCGG-3') (SEQ ID NO: 2) and 3 (5'-(Biotin)$_3$-TCGGGCGAGTCGTCTG-3') (SEQ ID NO: 3) as primers. Oligonucleotide 3 had three biotin phosphoramidites conjugated to its 5' terminus. The 72 nucleotide double stranded product was denatured by adding an equal volume of formamide and heating to 95° C. for 3 minutes, and electrophoresed on an 8% polyacrylamide gel containing 8M urea. The DNA strand lacking the biotin tag migrates faster than the biotinylated strand, and was isolated by excision from the gel, elution by squashing in 0.4 ml 2 mM EDTA and gentle agitation for 15 minutes, and centrifugation for 5 minutes using a microcentrifuge filter unit (CoStar Spin-X) to partition the ssDNA from the gel slurry. The recovered ssDNA was precipitated with 0.5M NaCl and 2 volumes of ethanol, pelleted by centrifugation, washed once with 0.4 ml 70% ethanol, dried, and resuspended in deionized, distilled water (dd$H_2O$).

Selection for PBMC Affinity and Amplification

The affinity of the degenerate ssDNA library for PBMCs was determined using a cell-excess nitrocellulose filter binding assay as described in Carey, et al. (1983) Biochemistry 22:2601–2609. Since the number of possible DNA binding targets on the surface of a PBMC is unknown, affinity values are reported as the concentration of cells (in units of cells/µl) showing half saturation in this assay. Selections for PBMC affinity were performed under DNA-excess conditions predicted to saturate available target sites, with heparin (Calbiochem, average M. W. 5000) added in excess of DNA to act as a non-amplifiable competitor and to increase stringency. PBMCs, DNA, and heparin were equilibrated for 15 minutes at 37° C. and PBMC:DNA complexes were partitioned from free DNA by filtration. PBMC-independent (background) retention of DNA was measured by filtering a similar reaction lacking PBMCs. Filters were prewet with 1 ml of wash buffer (50 mM Tris Acetate, pH 7.4) and following application of the sample, washed with 5 ml of wash buffer to remove unbound DNA. For selections 9–21, 0.5M urea was added to the wash buffer to further reduce background retention. To minimize the likelihood of enriching for DNA with an affinity for the filter, we alternated among three different filter types: nitrocellulose (Millipore, Type HA, 0.45 μm), acrylic-coated nylon (Gelman Sciences, Versapor-450, 0.45 μm) and glass microfibre (Whatman, GF/C).

For the first selection, 1.4 μM DNA (70 pmoles or about $4 \times 10^{13}$ molecules) was equilibrated with 100 μM heparin and PBMCs at final concentrations of 40,000, 20,000, 10,000, 5,000, and 2,500 cells in 50 μl PBS. The fraction of total DNA complexed to PBMCs and retained by the filters was calculated by measuring Cerenkov radiation in a scintillation counter. A plot of fraction of DNA bound as a function of total DNA gives a linear relationship with a slope equal to the number of DNA molecules bound per cell (an estimate of the number of DNA binding targets per cell). For each subsequent selection, 5–9 PBMC concentrations were tested and plotted in this fashion and the DNA/cell value recorded. In an additional effort to reduce enrichment for filter binders each selection, the filter with the cell concentration retaining between 1% and 10% of total DNA, and if possible, at least 10 times more DNA than PBMC-independent (background) retention, was chosen for further amplification and enrichment. The selected DNA was harvested from the filter as described in Tuerk and Gold (1990) Science 249:505–510, amplified by PCR, and size-purified by electrophoresis on an 8% polyacrylamide, 8M urea gel as described above. As enrichment progressed through successive selections, stringency was increased by decreasing the DNA concentration, increasing the heparin concentration, and for selections #12–21, performing the selections in fresh human plasma instead of PBS. Performing selections in plasma adds an element of specificity, as PBMC-binding DNA molecules with a higher affinity for a plasma component will be depleted from the library. The DNA, PBMC, and heparin concentrations, as well as other relevant selection data, are summarized in Table 1.

Cloning and Sequencing Isolates

Following selection #21, 2 pmol of the selected library was amplified by PCR using oligonucleotide 4 (5'-CCG AAGCTTAATACGACTCACTATAGGGAGGAC GATGCGG-3', containing a Hind III restriction endonuclease cleavage site, underlined) (SEQ ID NO: 4) and oligonucleotide 5 (5'-GCC GGATCCTCGGGCGAGTCGTCTG-3', containing a Bam HI site, underlined) (SEQ ID NO: 5) as primers. The double-stranded product was size-purified on an 8% polyacrylamide gel and recovered as described above. Fifteen pmol of the PCR product was digested with Hind III and BamHI, along with 1 pmol pUC19 (all from New England Biolabs) for 3 hours at 37° C. Following digestion, the sample was extracted once each with one volume of phenol and chloroform and recovered by precipitation as described above. The selected library was ligated into pUC19 with DNA ligase (New England Biolabs) for 3 hours at 37° C. and the ligation product introduced into *E. Coli* DH1αcells by electroporation transformation. Vectors from successful transformations were isolated using a standard plasmid mini-prep protocol and sequenced by dideoxy extension of end-labeled oligonucleotide 6 (5'-TTCACAC AGGAAACAG-3')(SEQ ID NO: 6) with Sequenase T7 DNA Polymerase (United States Biochemical). For a detailed description of these techniques, refer to Schneider, et al. (1993) FASEB 7:201–207. Larger quantities of individual ligands (>20 pmol) were prepared by amplifying the vector inserts by PCR using oligonucleotides 2 and 3 as primers and denaturing and size-purifying the product as described above.

Competition Assay Measuring Disruption of PBMC:DNA Complexes

In a 20 μl reaction containing 100 μM heparin in PBS, 10 nM end-labeled DNA was equilibrated with a saturating concentration of PBMCs (10,000 cells/μl) for 10 minutes at 37° C. 5 μl of unlabeled competitor DNA was then added to a final concentration ranging from 1.25 nM to 3.2 μM and allowed to equilibrate for 10 minutes at 37° C. Reactions were filtered and the percent of total labeled DNA retained on the filter was recorded.

B. RESULTS

Affinity for PBMCs was Enriched 40-Fold, and is Heparin Dependent

Following 21 rounds of enrichment by selection and amplification, the affinity of the DNA library for PBMCs was enriched by a factor of 40. In a cell-excess titration in PBS and 100 μM heparin, the degenerate library (DNA-0) showed half saturation at 43,500 cells/μl, while the fully enriched library (DNA-21) showed half saturation at 1,000 cells/μl. The difference in affinity between DNA-0 and DNA-21 is heparin dependent and most sensitive in the range of 10–100 μM. Below 10 μM, binding of the random library approaches that of the selected library, while above 100 μM, binding of the selected library begins to decrease and approach that of the random library. The relationship between heparin concentration and DNA binding demonstrates the ability of heparin to effectively compete for non-specific binding sites on PBMCs.

Enriched Library Consists of Families with Conserved Elements

From the enriched library, 34 members were isolated and sequenced as shown in Table 2 (SEQ ID NOs: 7–39). Of these 34 sequences, 33 were unique, and 29 contained the sequence TAGGG (or a variation one base removed) in two locations within the 40 nucleotide random cassette. When aligned by the TAGGG pentamers, additional conserved elements emerged and were used to classify the isolates into families as shown in Table 2. The sequences of the 34 isolates from the enriched library are aligned by their conserved TAGGG elements (boldface) and classified into families sharing other conserved elements. Only the sequence of the evolved 40 nucleotide cassette is shown in the alignment. The sequences of the invariant flanking regions are shown in the box and are the same as those from SEQ ID NO:1. Runs of 2 or more G residues are underlined. The 10 isolates chosen for further characterization are indicated with a bullet. Computer algorithms were unable to identify any stable secondary structures for the selected ligands, possibly due to an overall lack of pyrimidine residues (particularly C residues) in the random cassette. However, conservation of a complex higher-order structure cannot be ruled out, as a large number of GG elements (underlined in Table 2 and consistent with the formation of G-quartet motifs) were selected for in the random region and exist upstream in the invariant flanking region.

Isolates from the Enriched Library Bind PBMCs with High Affinity

To compare the affinity of the selected families for PBMCs, one member of each was chosen for a binding assay (indicated with a bullet in Table 2). The affinities of the chosen ligands in PBS and 100 μM heparin ranged from 400–3,000 cells/μl except ligand L9, which lacked the conserved TAGGG elements and showed half saturation at 15,400 cells/μl as shown in Table 3.

The Enriched Library Binds PBMCs but not RBCs

A DNA ligand is most useful if it not only shows high affinity binding to PBMCs, but also shows specific binding to PBMCs. Using the cell-excess binding assay described above, the affinities of DNA-0 and DNA-21 for human PBMCs, rat PBMCs, and human red blood cells (RBCs) were compared. In PBS and 2.5 mM heparin, rat PBMCs mimic human PBMCs in their interaction with each DNA library. In PBS and 100 µM heparin, DNA-21 binds better than DNA-0 to human RBCs, but even at cell concentrations as high as $10^5$/µl (saturation conditions for PBMC binding to DNA-21), RBCs show only 5% binding to DNA-21 and less than 1% binding to DNA-0.

DNA:PBMC Complexes are Disrupted by DNA Competitor

A characteristic of dead cells is an inability to pump out internalized DNA. To demonstrate that the DNA binding seen in the binding assays is a measure of complex formation on the surface of viable cells rather than internalization by dead cells, we pre-bound a saturating concentration of PBMCs with radiolabeled DNA-21 and followed with a chase of excess unlabeled DNA-21 at various concentrations. When the data is plotted as the percent of labelled DNA bound as a function of competitor concentration, a sigmoidal relationship is seen showing one-half saturation at approximately 20 nM competitor and approaching zero as the competitor concentration increases. When this data is plotted as a scatchard, two types of interactions are seen: a high affinity interaction with a $K_d$ value of 8 nM and a stoichiometry of $3 \times 10^5$ DNA/cell, and a low affinity interaction with a $K_d$ value of 460 nM and a stoichiometry of $3 \times 10^6$ DNA/cell. Internalization of DNA by dead PBMCs is inconsistent with these results, as all of the pre-bound DNA-21 is competed off at concentrations of unlabeled DNA-21 above 1000 nM.

EXAMPLE TWO

2'F RNA Ligands to Human Fibrin Clots

This example describes the ability to obtain RNA ligands to human fibrin clots. The pyrimidine residues of these RNA ligands have been modified with flourines at the 2'-position of the sugar. The fibrin ligands are useful as diagnostic agents as described previously.

A. METHODS

Clot formation

Human blood was collected in EDTA Vacutainer tubes (Becton-Dickenson), spun at 4° C. in a clinical centrifuge. Plasma was removed and stored at −70° C. Clots were generated in glass tubes by the addition of $CaCl_2$ to a final concentration of 20 mM, incubated for 12–16 hr at 37° C.

For the SELEX protocol, the clots were generated in the presence of a glass hanger. Clots were washed 2 hr at 20° C. by continuous exchange of 125 ml 0.01M HEPES, 0.125M NaCl, 2 mM $MgCl_2$, pH 7.5 (Fibrin buffer).

For the in vitro assays, clots were generated by recalcification of 50 ml plasma in 96-well micro dishes. After 12–16 hr in a humidified chamber at 37° C., the clots were washed by 4×200 µl buffer changes at 15 min each.

For the in vivo pulmonary embolism assay, clots were generated from recalcified plasma as above. Clots from 2 ml plasma were rimmed and centrifuged for 10 min in a clinical centrifuge. They were washed with 2 ml buffer with centrifugation. Clots were then homogenized for 1 min at low speed with a Tissue-Tearor (Biospec Products). Homogenate was washed 3×2 ml buffer followed by passage through 18, 20, 21, 22, and 23 Ga needles respectively. Homogenate was resuspended in 0.5 volumes buffer relative to initial plasma volume.

Generation of RNA Pool

2'F-pyrimidine, 2'OH-purine RNA was used for this SELEX. The initial DNA template, 40N8, was synthesized on a solid-phase automated DNA synthesizer by standard techniques and had the sequence gggagauaagaauaaacgcucaa-40N-uucgacaggaggcucacaacaggc (SEQ ID NO: 40). All subsequent PCR rounds utilized the primers 5'-taatacgactcactataggagauaagaauaaacgcucaa (SEQ ID NO: 41) and 5'-gcctgttgtgagcctcctgtcgaa (SEQ ID NO: 42) as the 5' and 3' primers respectively. PCR, reverse transcription and generation of RNA with T7 RNA polymerase was performed as previously described. Transcription of 2'F RNA was performed in the presence of 1 µmM each ATP and GTP (in the presence or absence of $\alpha$-$^{32}$P-ATP), and 3 mM each 2'F UTP and 2'F CTP. Transcription proceeded for 5–14 hr at 37° C. followed by gel electrophoretic purification in the presence of formamide and 7M urea.

SELEX Protocol

The general protocol used for this SELEX is outlined in Table 4. Clots from 0.5 ml plasma were immersed in a 1–4 mM soln of 2'F RNA pool in fibrin buffer for 1 hr at 20° C. Clots were washed by immersion with 4×1 ml buffer for 30 min each. The clot was then macerated with a sharp blade and shaken vigorously for 1 hr in 0.6 ml phenol and 0.45 ml 7M urea. 0.4 ml $CHCl_3$ is added to elicit a phase separation, followed by centrifugation at 14,000 RPM. The aqueous phase was extracted with equal volumes 1:1 phenol:$CHCl_3$, then $CHCl_3$, and precipitated with 1.5 ml 1:1 isopropanol: ethanol in the presence of NaOAc and tRNA as a carrier. Generally 0.5–10 pmoles RNA was recovered from a SELEX round.

Stringency and specificity were added to the SELEX after the pool showed signs of increased binding in buffer. Initially, after seven rounds of SELEX, the SELEX binding reaction was done in heparin-anticoagulated plasma. Subsequent washes were done in buffer. At later rounds, washes were also performed in heparinized plasma. No attempt was made to alter the clot size or RNA concentration. A first SELEX performed in this manner yielded a significant amount of fibrinogen cross-reactivity. A second SELEX was performed which diverged from the first at round six, at which time a fibrinogen 'Counter-SELEX' was added. 1–4 nmoles of a 1 mM transcribed pool RNA was premixed with human fibrinogen to a final concentration of 25 µM. After 15 min incubation at 37° C., the solution was filtered two times through three 1 cm diameter, 0.45 micron, nitrocellulose filters. This resulted in the removal of 80–90% of the protein. The filtered RNA was requantitated and added to clot SELEX reaction.

Sequence Alignment

CLUSTER Algorithm

CLUSTER is a program that performs multiple sequence alignment with reoptimization of gap placement within the growing consensus. The algorithm consists of two parts: sequence alignment and clustering. Sequence alignment uses the dynamic programming algorithm of Altschul and Erickson (Altschul and Erickson (1986) Bulletin of Mathematical Biology 48:603–616) with a weight vector selected on an a priori statistical basis, namely, a match=1.0, mismatch=−⅓, gap opening=−1.0 and gap extension=⅓. The total cost of alignment is the sum of each pairwise alignment within the consensus, utilizing the quasi-natural gap costs of Altschul (Altschul (1989) J. Theoretical Biology 138:297–309). Normalization of alignment costs allows for comparison between alignments that contain different numbers of sequences. The normalization used in CLUSTER compares an alignment to the best possible one in which every position matches. A normalized score is the cost of alignment divided by the cost of the best possible alignment. The K-Means algorithm clusters sequences into families. Here, the algorithm is modified slightly from the original version (Tou and Gonzales (1974) *Pattern recognition principles* (Addison-Wesley Publishing Company)) to a accommodat cost of alignment as the distance measure. Convergence occurs when there is only one family, or the cost to combine any two clusters is beyond a threshold. Optimization (Step 3) pulls out subsets of sequences and realigns them as described by (Subbiah and Harrison (1989) J. Mol. Biol. 209:539–548).

Fibrinogen binding

Fibrinogen binding was determined by standard nitrocellulose filter binding assays as described in the SELEX Patent Applications.

In vitro clot assay

To 50 µl clot in microtiter wells was added 5,000 or 25,000 CPM (~0.5 or 2.5 pmoles) in 100 µl. Clots were incubated for 1 hr followed by 4×200 µl buffer washes at 15 min each. Microtiter wells were counted directly in the presence of scintillant.

In vivo pulmonary embolism assay

Clot homogenate prepared as above from 200 µl plasma was admixed with 100 pmoles (~1×10$^6$ CPM) for 15 min at 22° C. just prior to injecting suspension via a 23-ga needle into the tail vein of a 200–250 gm Sprague-Dawley male rat. At predetermined times, the animal was sacrificed by exsanguination followed by removal of the lungs. The left lung, which consists of only one lobe, was pressed onto Whatman one paper and then dried on a gel dryer at 80° C. for 2 hr and subjected to autoradiography. The multi-lobar right lung was homogenized in 1 ml buffer and quantitated in scintillant.

Histologic autoradiography

To visualize clot-bound RNA, histologic autoradiography was employed. RNA was 5'-end-labeled with γ-$^{33}$P-ATP. Binding was performed as described for the SELEX reactions or for the in vivo pulmonary embolism assay. Tissues were fixed at least 24 hours in 10% neutral buffered formalin, processed to paraffin, and made into 5 µm sections on poly-L-lysine slides. After drying in 60° C. oven, they were deparaffinized and rehydrated prior to exposure. Lungs were perfused with normal saline via the right atrium and inflated with 10% formalin prior to removal, fixation and imbedding. Slides were dipped in melted nuclear emulsion (Amersham LM-1), allowed to dry, and exposed at 4° C. Slides were developed in Dektol developer (Kodak), fixed (Kodak Fixer), and stained in Giemsa (Sigma).

B. RESULTS

Two separate SELEXes were performed on fibrin clot as outlined in Table 4. The two SELEXes differed in the degree and method of counter-SELEX. In the first SELEX (termed FC), eleven total rounds were performed. The binding reaction was performed in buffer for the first seven rounds. The binding was done in human heparinized plasma for rounds eight and nine. The final rounds were done in whole human heparinized blood. In all rounds, the clot was washed with Fibrin buffer. The second SELEX (termed FCN) diverged from the first at round six when there was a first indication of enrichment. A 25 µM fibrinogen counter-SELEX was added to each round beginning at round six. In addition, the binding reactions were done in heparinized human plasma and the clots were washed with plasma instead of physiologic buffer for rounds 7–14. The final round pools bound 2.5% and 6.4%, respectively, in the presence of heparinized plasma. The round twelve and fourteen pools for the first and second SELEXes, respectively, were sequenced. In both cases RNA sequencing indicated considerable nonrandomness. The pools were amplified with new primers containing EcoR1 and Hind III sites on the 5' and 3' end, respectively, and cloned into pUC 18.

Visualization of clot binding

The round eleven pool from the initial SELEX was 5'-end labeled with $^{33}$P. The pool was admixed with clot in an identical manner to a SELEX in Fibrin buffer. After washing the clot was fixed in formalin, imbedded, sectioned and overlayed with autoradiography emulsion. Development of the sections showed the RNA (visualized as black grains) were coating the outside of the clot with some diffusion into the interstices of the clot. In another experiment, the rat PE model was performed with $^{33}$P kinased ligand. The pool was pre-bound to the homogenized clot and injected into the tail vein of a rat. At fifteen minutes the rat pulmonary bed was perfused with saline via the right atrium. The lungs were inflated and fixed by injection of 10% formalin into the trachea prior to removal and placement in formalin. Tissues were processed as above. Tissues showed black grains only in close association with intravascular clots. There was no evidence of RNA pooling downstream of occluded vessels. Furthermore, when the study was run with a non-evolved round 0 pool no black grains were visualized within the lung.

Sequence analysis and activity screening

Seventy-two clones of each were sequenced (SEQ ID NOS: 43–130). Eighty-eight unique clones were seen and 15 clones differed by only one nucleotide. The sequences were combined for analysis and grouped into sequence motifs by the application of CLUSTER and visual inspection as shown in Table 5. Only the sequence of the evolved 40 nucleotide cassette is shown in the alignment. The sequences of the invariant flanking regions are included in each clone and are the same of those in SEQ ID NO:40. When the unique clones from both SELEXes were combined for CLUSTER analysis they formed 17 separate motifs. 27/88 clones (31%) were grouped into two major motifs. Motif I and II had 15 and 12 members, respectively. A third motif (Motif III) contained 9 members primarily from the first SELEX and had properties similar to Motif I. Four of the motifs had only two members each.

78/88 (89%) clones were screened for binding in the qualitative in vitro microtiter plate assay. These clones were grouped into high, medium and low affinity with 37, 10, and 31 members in each group, respectively. 46/78 clones screened were further screened for fibrinogen-binding activity. The screen was a standard nitrocellulose binding assay employing a four-point curve from 0.1–10 µM fibrinogen concentration. Sixteen of the clones were further screened for clot binding in the in vivo rat pulmonary embolism assay. Results for each of these assays are shown in Table 5.

Of the 27 clones in the major two sequence motifs, 24 were evaluated by the initial screen for binding in the microtiter plate assay. Of those, 15/24 (63%) were characterized as high-affinity or moderate-affinity clot binders. The fibrinogen-binding screen was also divided into high, moderate and low affinity groups with 14, 6, and 26 in each group, respectively. In the fibrinogen-binding screen, high-affinity binders were included if the Kd<1 mM, while low-affinity binders included those clones with a Kd>1 mM. In Motif I, 10/11 (91%) were in the high- or moderate-affinity for fibrinogen binding while, in Motif II, 0/9 (0%) fell in the high- or moderate affinity fibrinogen binding groups. Eleven members of Motifs I, II were tested in the in vivo PE assay. The clones from Motif I had on average 40% increase in clot binding over Motif II when the binding reaction was performed in buffer. However, when the binding reaction was performed in heparinized plasma, Motif I had a binding decrease by 90% while Motif II had a decrease of only 10%. There was a clear distinction between Motif I and II in the degree of fibrinogen binding. Motif I bound clots with a slightly greater degree than Motif II but had a significant degree of crossreactivity. More definitive fibrinogen binding curves indicated that Motif I clones had Kd of 200–600 nM. The Kd(fibrinogen) of Motif II is too high to be quantitated accurately. 1–3% binding was seen at the highest fibrinogen concentration of 10 μM. One can extrapolate a Kd of greater than 100 μM.

Binding Quantitation

The two best binders in the PE model which had the lowest affinity for fibrinogen were pursued. Both of these clones resided in Motif II. Clone 69 (SEQ ID NO: 55) was analyzed for binding in vitro homogenized clot. By adding a fixed amount of radiolabeled clone 69 (2 nM) to a fixed amount of clot (200 μliters plasma equivalent) with increasing amount of nonradiolabeled ligand, binding could be quantitated. Analyzing data in a Scatchard format yields a two-component curve with high and low affinity binding components. There were 200 nM high affinity sites per 200 μliters plasma equivalent. The ligand bound these sites with a Kd of 10–20 nM. These sites were saturable. Furthermore, if the ligand was pre-bound to the clot homogenate, it could be competed off the clot by the addition of 3 μM unlabeled clone FC 69 with a half-life of 37 min. The labeled ligand did not diffuse off the clot homogenate to any significant degree over 4 hours in the presence of buffer alone or 3 mM of a 2'F clone which had no measurable affinity for clots. As such it appears that the binding of a specific ligand to clots is specific and stable.

Clone Truncation

Boundary experiments were performed in which the ligand was radiolabeled on either the 5' or 3' end. The ligand was subjected to partial cleavage by modest alkaline hydrolysis and bound to fibrin. Binding RNAs were purified and sequenced. The results are shown in Table 6. Typically a ladder was seen until a region critical to binding was lost, at which point there is a step-off on the sequencing gel. Duplicating the reaction with both ends labeled allowed the determination of both the 5' and 3' boundary. Boundary studies were performed on one clone from Motif I and two clones from Motif II. All clones could be folded into a putative secondary structure which was consistent with the boundaries. The Motif I could be folded into a 'dumbell' structure. Motif II used a significant amount of the 3'-fixed region. It could be folded into a stem-loop/bulge structure. Based on the boundaries and the structure potentials four nested synthetic 2'F oligonucleotides of clone FC 69 (SEQ ID NO: 55) were synthesized by automated solid-phase synthesizer ranging from 25–41 nucleotides in length (SEQ ID NOS: 131–134). These were tested for binding to homogenized clot by competition with full-length material both in vitro and in the rat PE model. In the in vitro assay, qualitatively binding was seen with all four clones, 69.4 (SEQ ID NO: 134) (the longest) being the best. In the rat PE model, again, all four truncates bound clot. The two truncates with four additional nucleotides past the boundary on the 3'-end showed 3-fold increased binding over those whose sequence ended exactly at the 3'-boundary. The binding to clots in the lung as normalized to full-length material was 32, 118, 36, and 108% for each of the four truncates, respectively. Furthermore, the binding of the best truncate in this assay, 69.2 (SEQ ID NO: 133)(29-nucleotides), was partially inhibited by the addition of 1 μM unlabeled full-length clone FC 69.

EXAMPLE THREE

RNA Lipands to Stenotic Carotid Arteries

This example describes the ability to obtain RNA ligands to rat stenotic carotid arteries. The stenotic carotid arteries ligands are useful as diagnostic and pharmaceutical agents as described previously.

A. METHODS

Generation of RNA Pool

2'F-pyrimidine, 2'OH-purine RNA was used for this SELEX. The initial DNA template, 40N8, was synthesized on a solid-phase automated DNA synthesizer by standard techniques and had the sequence gggagauaagaauaaacgcucaa-40N-uucgacaggaggcucacaacaggc (SEQ ID NO: 40). All subsequent PCR rounds utilized the primers: 5'-taatacgactcactatagggagauaagaauaaacgcucaa (SEQ ID NO: 41) and 5'-gcctgttgtgagcctcctgtcgaa (SEQ ID NO: 42) as the 5' and 3' primers, respectively. PCR, reverse transcription and generation of RNA with T7 RNA polymerase was performed as previously described. Transcription of 2'F RNA was performed in the presence of 1 mM each ATP and GTP (in the presence or absence of α-$^{32}$P-ATP), and 3 mM each 2'F UTP and 2'F CTP. Transcription proceeded for 5–14 hr at 37° C. followed by gel electrophoretic purification in the presence of formamide and 7M urea.

SELEX Protocol 250 gm male Sprague-Dawley were subjected to either unilateral or bilateral balloon-injury of the carotids. Rats were anesthetized with isoflourane. The carotids exposed by a 1 cm midline incision. The common, internal, and external carotid were identified. A #2 French Fogarty catheter was inserted into the external carotid just above the bifurcation and advanced to the aortic arch. The balloon was inflated and pulled back to the bifurcation. This was repeated six times. The catheter was removed, and the external carotid was ligated. The skin was closed by cyanoacrylate glue. Injuries were allowed to develop for 10–14 days.

At the time of SELEX, animals were sacrificed under anesthesia by exsanguination. Both carotid arteries were dissected from the bifurcation to the aortic arch. The arteries were gently stripped of any associated connective tissue. Twelve rounds of SELEX were performed ex vivo as indicated in Table 7. The first three rounds were done by simply immersing two arteries in 0.5 ml of a 2 μM RNA solution. The binding reaction was rotated at 20° C. Carotid segments were then washed with four 1 ml buffer washes for 15 min each prior to harvesting the bound RNA. Subsequently, two carotid arteries were ligated together in series with a small length of polyethylene tubing. The distal ends were also canulated with tubing for attachment to a syringe pump and collection of eluant. These procedures were done with minimal disruption to the arterial segments. For the SELEX, 0.75–2.3 nmoles in one ml physiologic buffer was passed through the arterial segments at 4 ml/hr. This was followed by washing the segments with an additional 1 ml of buffer at 4 ml/hr. The segments were taken out of line, counted by Cherenkov radiation, and processed for RNA extraction. Rounds 4–7 were performed in this manner with both artery segments having been balloon-injured. All tissue was processed for RNA extraction. In rounds 8–12, an uninjured artery was ligated upstream from an injured artery as shown in FIG. 1. Perfusion proceeded as above. Both artery segments were counted, but only the injured segment was processed for RNA extraction. Rounds 8–12 were done to 'counter-SELEX' against the evolved RNA binding normal arterial endothelium. In a subsequent control, it was shown that the uninjured artery had an intact monolayer of intimal endothelium by Factor VIII immunohistochemistry.

Tissue Extraction of 2'F-RNA

Carotid segments were minced with a scalpel and homogenized with 1 ml TRIZOL Reagent (Gibco). Homogenate was clarified by centrifugation, phase-separated with $CHCl_3$, and the aqueous phase precipitated with IpOH, all according the manufacturers protocol. Purified RNA was resuspended in $H_2O$, and digested for 15 min at 37° C. with 0.1 U/μL DNAse I (Pharmacia) and 100 μg/ml RNAse A (Sigma) in reverse transcription buffer. 2'F-pyrimidine, 2'OH-purine RNA is stable to RNAse A digestion. The digest was phenol, phenol/$CHCl_3$ extracted and EtOH precipitated out of Na Acetate. The RNA was then subjected to RT/PCR under standard conditions to generate a template for T7 RNA polymerase. After twelve rounds the pool was cloned and sequenced. The sequences identified as C# in Table 8 were obtained by this protocol.

In Vivo SELEX

In a subsequent SELEX, 3–5 nmoles of the Round twelve pool was injected directly into the tail vein of a rat with a 14 day unilateral lesion. After 15 min, the animal was sacrificed and the carotids processed. RNA was amplified as before. Four Rounds of in vivo SELEX were done as indicated in Table 7. This pool was cloned and sequenced and the sequences from both cloning steps were combined for sequence analysis. The sequences identified as Civ# in Table 8 were obtained by this protocol.

Binding Analysis

Binding of RNA either as a pool or individual clones was performed by comparing $^{32}P$ counts bound to normal versus injured carotid artery segments. Binding was visualized by histologic autoradiography in either the ex vivo perfusion system or by overlaying RNA onto fresh-frozen carotid artery slices.

Histologic autoradiography

To visualize carotid-bound RNA, histologic autoradiography was employed. RNA was 5'-end-labeled with $\gamma$-$^{33}P$-ATP. Binding was performed as described for the SELEX reactions. Tissues are fixed at least 24 hours in 10% neutral buffered formalin, processed to paraffin, and made into 5 mm sections on poly-L-lysine slides. After drying in 60° C. oven, they are deparaffinized and rehydrated prior to exposure. Slides are dipped in melted nuclear emulsion (Amersham LM-1), allowed to dry, and exposed at 4° C. Slides are developed in Dektol developer (Kodak), fixed (Kodak Fixer), and stained in Giemsa (Sigma).

Fresh-frozen carotid sections were prepared by imbedding normal or injured carotid artery segments in OCT and freezing at −20° C. 5 μm sections were cut on a cryostat, placed on a slide (typically a normal and injured section were juxtaposed on a single slide), and stored frozen at −5° C. Slides were warmed to room temperature, the paired sections are encircled with a grease pencil, and pre-bound with 30 ml PBS, 0.5% Tween-20, 1 mM low molecular weight heparin (Calbiochem). After 15 min the solution was removed and 30 μl of the same solution containing 10,000 CPM (~1 pmole) 33p-labeled RNA is added for 30 min. Slides were washed twice with PBS/Tween-20, twice with PBS. Slides were fixed in 10% neutral buffered formalin, then rinsed in distilled water prior to exposure.

Sequence Alignment
CLUSTER Algorithm.

CLUSTER is a program that performs multiple sequence alignment with reoptimization of gap placement within the growing consensus. The algorithm consists of two parts: sequence alignment and clustering. Sequence alignment uses the dynamic programming algorithm of Altschul and Erickson (Altschul and Erickson (1986) Bulletin of Mathematical Biology 48:603–616) with a weight vector selected on an a priori statistical basis, namely, a match=1.0, mismatch=−⅓, gap opening=−1.0 and gap extension=−⅓. The total cost of alignment is the sum of each pairwise alignment within the consensus, utilizing the quasi-natural gap costs of Altschul (Altschul (1989) J. Theoretical Biology 138:297–309). Normalization of alignment costs allows for comparison between alignments that contain different numbers of sequences. The normalization used in CLUSTER compares an alignment to the best possible one in which every position matches. A normalized score is the cost of alignment divided by the cost of the best possible alignment. The K-Means algorithm clusters sequences into families. Here, the algorithm is modified slightly from the original version (Tou and Gonzales (1974) *Pattern recognition principles* (Addison-Wesley Publishing Company)) to accommodate cost of alignment as the distance measure. Convergence occurs when there is only one family, or the cost to combine any two clusters is beyond a threshold. Optimization (Step 3) pulls out subsets of sequences and realigns them as described by (Subbiah and Harrison (1989) J. Mol. Biol. 209:539–548).

B. RESULTS
SELEX

Twelve rounds of ex vivo RBIC SELEX was performed followed by four rounds of in vivo SELEX as indicated in Table 7. Pools were cloned and sequenced after the ex vivo SELEX and the ex vivo/in vivo SELEX; the sequences are provided in Table 8. Only the sequence of the evolved 40 nucleotide cassette is shown in the alignment of Table 8. The sequences of the invariant flanking regions are included in each clone and are the same as those of SEQ ID NO: 40. The last five rounds of the ex vivo SELEX were done with a normal carotid artery as a negative selection (Counter-SELEX). Evaluation of these rounds indicated that over the last five rounds the injured carotid bound between 0.07–0.5% without a trend towards increased binding in the later rounds. The discrimination between normal and injured was 3.2–4.5, again without a trend toward increased discrimination. At round twelve, the RNA pool was sequenced and shown to be significantly non-random.

The pool was then taken forward in the in vivo SELEX. Very little RNA was recovered from the injured carotid arteries (0.2–0.6 pmoles). Comparing CPM in the normal versus injured yielded discrimination values of 2.61–3.54. At the first round of in vivo SELEX, equal amounts of round XII RNA and Round 0 RNA were injected into two different animals both with unilateral balloon injuries. There was no discrimination for the Round 0 RNA (i.e. the same number of counts bound the normal as the injured artery), whereas in the round 12 pool, 2.61 times more RNA bound the injured carotid as compared to the uninjured. At Round 15, the evolved pool was injected into the animal or perfused through an ex vivo apparatus exactly as had been done for rounds 8–12. The discrimination of the Round 15 RNA was 4.61, which was higher than had ever been seen during the ex vivo SELEX.

Seventy-two clones from the ex vivo SELEX were sequenced, of which 50 were unique as shown in Table 8.

The striking finding was that of the seventy-two clones, two were present in multiple copies. One clone (clone C33 (SEQ ID NO: 146)) had nine identical or one base difference copies, while another (clone C37 (SEQ ID NO: 186)) had ten copies. Thus nineteen of twenty-two copies in the initial sequencing arose from two sequences. Sequences stemming from those two persisted after the in vivo SELEX with clones related to C33 generating the largest single family in the combined analysis (Motif I).

Analysis of Clone Binding

Of the ninety-four unique clones from the two SELEX methods, twenty-eight were screened for binding to fresh-frozen rat carotid artery sections. These were qualitatively graded by intensity of staining (+, ++, +++) and specificity (s, ns) as shown in Table 8. Clones were seen with a variety of patterns from no visible binding to strong binding of all tissue components. Specificity was graded based on relative intensity of binding to neointimal tissue over normal or injured media or adventia. Early on C33 (SEQ ID NO: 146) was found to have both increased intensity and specificity over both unevolved Round 0 or Round 12 pool RNA. Further screening uncovered three other clones with better binding characteristics: C59 (SEQ ID NO: 150) , Civ45 (SEQ ID NO: 202) , and Civ37 (SEQ ID NO: 210). Civ41 (SEQ ID NO: 158) was of interest because it was of the same Motif as C33 and C59, but had very intense staining and little specificity: staining neointima, as well as normal an injured media. Civ45 in three independent binding experiments had the most intense staining in a specifically neointimal distribution. This clone also showed an slight increase in binding to injured media over normal media. If smooth muscle cells migrate from the media to the neointima in the injured artery, then it may not be surprising that whatever this clone is binding exists within the injured media. Of the four clones noted with high specificity, two of them are from Motif I and are closely related. Three of the four contain the sequence GUUUG (underlined in Table 8). Putative secondary structures are shown in Table 9. It is unknown at this time whether these structures correlate to the true structure. In the absence of boundary experiments they provide a basis for truncation studies.

Clone C33 and C59 were $^{33}$P-labeled and perfused in an ex vivo manner. Although not quantitated, they showed dramatic binding to the lumenal wall of the damage artery but not to the normal vessel.

C59 was used to stain fresh-frozen section of RBIC of different ages. Carotids were harvested at 1, 2, 4, 6, 8, 16 wks after balloon injury. The neointimal signal was greatest at 2–6 wks. It was minimally present at one wk and disappeared after six. The pattern of staining neointima in the highly specific clones is diffusely granular. Silver grains are not obviously associated with smooth muscle cell bodies. One hypothesis is that RNAs are binding to components of the extracellular matrix (ECM). It is known that SMCs require an ECM scaffold to migrate. They have been shown to lay down unique proteoglycans in the course neointimal proliferation. The presence and disappearance of these unique proteoglycans corresponds temporally to the binding of RNAs to neointima. As such one viable possibility is that the RNAs are binding specifically to these proteoglycans.

TABLE 1

Summary of Selection Parameters and Data for PBMC SELEX

| Selection | [DNA] nM | [PBMC] cells/µl | [heparin] µM | Filter Type | % PBMC retention | % bkgd retention | DNA/cell |
|---|---|---|---|---|---|---|---|
| 1 | 1,400 | 40,000 | 100 | NC | 3.1 | 0.1 | $6.0 \times 10^5$ |
| 2 | 900 | 120,000 | 100 | NC | 4.7 | 0.3 | $2.0 \times 10^5$ |
| 3 | 800 | 92,000 | 100 | GF | 3.5 | 0.8 | $9.0 \times 10^4$ |
| 4 | 480 | 60,800 | 100 | AN | 1.8 | 0.08 | $8.7 \times 10^4$ |
| 5 | 500 | 52,500 | 500 | NC | 4.6 | 0.3 | $2.2 \times 10^5$ |
| 6 | 990 | 18,300 | 500 | NC | 1.3 | 0.05 | $5.0 \times 10^5$ |
| 7 | 750 | 14,400 | 2,500 | NC | 1.6 | 0.09 | $2.2 \times 10^5$ |
| 8 | 560 | 47,800 | 2,500 | AN | 4.0 | 0.2 | $2.8 \times 10^5$ |
| 9* | 100 | 11,200 | 2,500 | NC | 7.2 | 0.5 | $9.3 \times 10^4$ |
| 10* | 100 | 12,600 | 2,500 | AN | 3.1 | 0.6 | $1.0 \times 10^5$ |
| 11* | 100 | 5,100 | 2,500 | NC | 5.7 | 0.7 | $7.3 \times 10^4$ |
| 12* | 50 | 37,500 | 2,500 + plasma | NC | 2.2 | 0.1 | $2.3 \times 10^4$ |
| 13* | 50 | 75,000 | 2,500 + plasma | AN | 4.9 | 0.3 | $2.2 \times 10^4$ |
| 14* | 10 | 32,000 | 2,500 + plasma | NC | 0.9 | 0.2 | $1.6 \times 10^3$ |
| 15* | 10 | 32,000 | plasma | NC | 3.1 | 0.3 | $2.3 \times 10^3$ |
| 16* | 10 | 112,000 | plasma | AN | 5.6 | 0.5 | $3.1 \times 10^3$ |
| 17* | 10 | 65,000 | plasma | NC | 3.0 | 0.6 | $3.1 \times 10^3$ |
| 18* | 10 | 87,300 | plasma | AN | 4.8 | 0.5 | $4.2 \times 10^3$ |
| 19* | 10 | 118,560 | plasma | AN | 6.0 | 0.5 | $3.3 \times 10^3$ |
| 20* | 10 | 94,560 | plasma | NC | 4.0 | 0.3 | $3.1 \times 10^3$ |
| 21* | 10 | 48,000 | plasma | AN | 7.3 | 0.7 | $5.8 \times 10^3$ |

TABLE 2

PBMC SEQUENCES

| Degenerate ssDNA Library |
|---|
| 5'- AGGGAGGACGATGCGG - [N]$_{40}$ - CAGACGACTCGCCCGA - 3'  (SEQ ID NO: 1)<br>5'fixed region     random region     3'fixed region |

| Ligand | Random Region (fixed regions are provided as described above) | | | SEQ ID NO: |
|---|---|---|---|---|
| • L49 | GGGGTCGGTTCGGGCATA | TAGGG TATTCTTCGTA | GAGGG | 7 |
| L8 | GGGGTCGGTTCGGGCATA | TAGGG TATTCTTCGTA | AAGGG | 8 |
| L35 | GGGGTCGGTTCGGGCATA | TAGGG TATCCTTCGTA | GAGGG | 9 |
| • L1,L34 | CACGT TAGTAGGAT | TAGGA TTATTCAGGTTG | TAGGG AACA | 10 |
| L29 | CACGTTCAGCAGGAT | TAGGG TTGTTTNGGTTG | TAGGG ACACA | 11 |
| L18 | CACGG TAGTAAGTAG | TAGGG TATTATA AT | TAGGG GATCCA | 12 |
| L21 | CACGG CAGTATTATT | CAGGG GTCTTAGATAT | TAGGG GGCA | 13 |
| • L42 | CACGGTAGGTTTTAGA | TAGGG ATATTTGGTG | TAGGG AGCA | 14 |
| L5 | CACGGTAGGTTATAGA | TAGGG ATATTTNTTG | TAGGG AACA | 15 |
| L11 | CACGGTAGGTTTTAGA | TAGGG ATATTTGATG | TAGGG AGCA | 16 |
| L25 | CACGGTAGGTTTTAGA | TAGGG ATATTTGGTA | TAGGG AGCA | 17 |
| L36 | CACGGTAGGCTTTAGA | TAGGG ATATTTGATG | TAGGG AGCA | 18 |
| • L26 | GGGGAG | TAGGG TATTTAAAAATGT | TAGGG TAAGTTTCCTC | 19 |
| L10 | GGGGAG | TAGGG TATTTAAAGTGT | CAGGG TAAGTTTCCTC | 20 |
| • L7 | CGTAGTAAGAAGTATTAT | TAGGG ATATTG | TAGGG GCGCTA | 21 |
| L22 | CGTAGTAAGAAGTATTAT | TAGGG ATATTG | CAGGG GCGCTA | 22 |
| • L43 | GGCAGCAAGA GTTTGAT | TAGGG TATAGT | TAGGG GCGCTG | 23 |
| L19 | GCAGCAAGA GTTTGAT | TAGGG TATAGT | TAGGG GCGCTGC | 24 |
| L41 | GCAGTAAGG GTTTGAT | TAGGG TATAGT | TAGGG GCGCTGC | 25 |
| L46 | GCAGCAAGAGG TTGAT | TAGGG TATAGT | TAGGG GCGCTG | 26 |
| L20 | CGGCAAGATGATTGAA | TAGGG GATCTAAAGT | TAGGG GCGC | 27 |
| L6 | GCAGCAGG TG | TAGGG GTATAGATGGA | TAGGG ATTTCTTCT | 28 |
| • L28 | CACA | TAGGG GAAATGA GAATAG | TAGGG TATTAATACAGTG | 29 |
| L38 | CACA | TAGGG GAAATGA GAAGAA | TAGGG TATTAATACAGTG | 30 |
| L50 | CAGGT | TAGGG GAAAGGTTTAATAAT | TAGGG TATAAAT GTG | 31 |
| • L14 | CAGGTAGAGA | TAGGG AAGTTTTATG | TAGGG GACAATTCGT | 32 |
| L44 | CAGGTAGAGA | TAGGG AAGTTTTATG | TAGGG GACAATTCGT | 33 |
| • L31 | CACAA | TAGGG AAATTT GTTGTTATAGT | TAGGG ATACTGGA | 34 |
| l40 | GGCCGAA | TAGGG AAATTTA TTATTACT | AACAGTAATCCCC | 35 |
| L48 | CAGGACT | TAGGG ATTTAGTTGTTT | TAGGG GTTATGTAGT | 36 |

TABLE 2-continued

PBMC SEQUENCES

| Degenerate ssDNA Library | |
|---|---|
| 5'- AGGGAGGACGATGCGG - [N]$_{40}$ - CAGACGACTCGCCCGA - 3'<br>   5'fixed              random      3'fixed<br>   region              region      region | (SEQ ID NO: 1) |

| Ligand | Random Region (fixed regions are provided as described above) | SEQ ID NO: |
|---|---|---|
| • L9 | GGGGGGATGAGATGTAATCCACATGTCACTTATTAAGTCC | 37 |
| L12 | CAGGGGATGGGATGTAATCCTCATGTCACTTATTAAGTCC | 38 |
| L13 | TACGACTACGATTGAGTATCCGGCTATAATATTACCATTG | 39 |

TABLE 3

Sequences and Affinities of Selected PBMC Ligands

| LIGAND | SEQUENCE OF RANDOM REGION | AFFINITY (PBMC/µl) | SEQ ID NO: |
|---|---|---|---|
| DNA-0 | Degenerate DNA Library | 43,500 | 1 |
| DNA-21 | Enriched DNA Library | 1,000 | |
| L1 | CACGTTAGTAGGATTAGGATTATTCAGGTTGTAGGGAACA | 3,000 | 10 |
| L7 | CGTAGTAAGAAGTATTATTAGGGATATTGTAGGGGCGCTA | 700 | 21 |
| L14 | CAGGTAGAGATAGGGAAGTTTTATGTAGGGGACAATTCGT | 1,200 | 32 |
| L26 | GGGGAGTAGGGTATTTAAAAATGTTAGGGTAAGTTTCCTC | 800 | 19 |
| L28 | CACATAGGGAAATGAGAATAGTAGGGTATTAATACAGTG | 2,400 | 29 |
| L31 | CACAATAGGGAAATTTGTTGTTATAGTTAGGGATACTGGA | 1,800 | 34 |
| L42 | CACGTAGGTTTTAGATAGGGATATTTGGTGTAGGGAGCA | 1,100 | 14 |
| L43 | GGCAGCAAGAGTTTGATTAGGGTATAGTTAGGGGCGCTG | 700 | 23 |
| L49 | GGGGTCGGTTCGGGCATATAGGGTATTCTTCGTAGAGGG | 400 | 7 |
| L9 | GGGGGGATGAGATGTAATCCACATGTCACTTATTAAGTCC | 15,400 | 37 |

TABLE 4

Serum Clot SELEX 2'F-40N8-RNA

| Round | Method | [Clot] | [RNA] | [NaCl] | Wash | Volume, ml | % bound | Yield, pm | Background |
|---|---|---|---|---|---|---|---|---|---|
| FC | | | | | | | | | |
| 1 | clot incubation | 500 ul plasma | 4.00E-06 | 125 mM | Buffer | 0.5 | 1 | 26 | |
| 2 | " | " | 4.00E-06 | 125 mM | " | " | 0.66 | 12.3 | |
| 3 | " | " | 1.90E-06 | 125 mM | " | " | 0.18 | 1.6 | |
| 4 | " | " | 4.00E-06 | 125 mM | " | " | 0.18 | 3.5 | |
| 5 | " | " | 4.00E-06 | 125 mM | " | " | 0.37 | 7.8 | |
| 6 | " | " | 4.00E-06 | 125 mM | " | " | 2.9 | 50 | |
| 7 | " | " | 4.00E-06 | 125 mM | " | " | 6.2 | 81 | |
| 8 | " | " | 3.00E-06 | Hep. Plasma | " | " | 9 | 67 | |
| 9 | " | " | 4.00E-06 | Hep. Plasma | " | " | 4 | 53 | long wash |
| 10 | " | " | 2.90E-06 | Hep. Blood | " | " | 7.9 | 70 | |
| 11 | " | " | 4.00E-06 | Hep. Blood | " | " | 2.5 | 46 | |
| FCN | | | | | | | | | Counter-SELEX |
| 7 | clot incubation | 500 ul plasma | 5.40E-06 | Hep. Plasma | Hep. Plasma | 0.5 | 0.7 | 20 | 0.025 mM fibrinogen |
| 8 | " | " | 1.93E-06 | " | " | " | 1.3 | 8.6 | " |
| 9 | " | " | 2.47E-06 | " | " | " | 1.4 | 15 | " |
| 10 | " | " | 6.00E-07 | " | " | " | 2.3 | 4.7 | " |
| 11 | " | " | 2.00E-06 | " | " | " | 2.6 | 20 | " |
| 12 | " | " | 3.80E-07 | " | " | " | 1.8 | 14 | " |
| 13 | " | " | 1.80E-06 | " | " | " | 1.9 | 12 | " |
| 14 | " | " | 2.10E-06 | " | " | " | 5.1 | 41 | " |

TABLE 5

Fibrin-Binding Clones

| FINAL CLUSTERS | | SEQ ID NO | In Vitro Clot Binding | Fibrinogen Affinity | Binding PE Assay |
|---|---|---|---|---|---|
| FC1 | : AGGGCUCGUGUGCCAAAUCGCUAACAAC-AAGCUAGCUGAU | 43 | o | | |
| FCN54 | : CUGGGCUCAUCCGGCGAAU-GAUG-CAAGGAAGAUUUCACAU | 44 | o | % | |
| score 0.365079 | | | | | |
| FC3 | : AAGGA-UAG-UGUGCU--CCUGUA--CCAAAUUUCCAAAGCGAUAU | 45 | o | | |
| FC73 | : AAAGAGUAA---AGCG--CG-GAA--CAGGAUUCACGUUGCGCUCUU | 46 | o | | |
| FC75 | : AAAGAGUAA---AGCG--CG-GAA--CAGGAUUCACGUUGCGCUCA | 47 | o | | |
| FCN6 | : CAACGAUUAUCUUUUCGGCCGUGAAACCCAAACUGACGCC | 48 | o | % | |
| score 0.292824 | | | | | |
| FC4 | : CGCGAGGAUAGGGUG--CAGCUUCUGUUCCAAAUACGUGA-AU | 49 | * | | |
| FC12 | : UAAGUCGAAGAGCUCCUGAUCCAAACCAUCGA-AAG-GACGU | 50 | o | | |
| FC28 | : GG-UAAGUUG--GAGCUCCUUAUCCAAGCACGCAAUAAGUGAC | 51 | o | | |
| MOTIF II score 0.355556 | | | | | |
| FC6 | : UUUGGCGU-GG-GAU-CCUGGA-CUGAAGG---AUUUUGACGAUGC | 52 | o | | |
| FC45 | : AUUCAAGACA-GA-GAC-UUUCCU-U-GAA--U-GCUCUGUCCCAUAA | 53 | | | |
| FC54 | : ACAAAUGU-GC-GAC-CUUGGA-C-GAAGUUAACUCGGACGGUUC | 54 | o | | |
| FC69 | : ACAAAUGU-GC-GCC-CUUGGA-C-GAAGUUAACUCGGACGGUUC | 55 | * | % | $ |
| FC72 | : ACAAAUGU-GC-GCC-CUUGGA-C-GAAGUUAACUCGGACGGUUG | 56 | * | % | |
| FCN16 | : ACAAAUGU-GC-GCC-CUUGGA-C-GAAGUUAACUCGGACGGUUC | 57 | o | % | |
| FCN19 | : AAGUCU-GA-GACUCCUGGA-CUGAA-UUAGCUAGGACGGCUG | 58 | ● | % | $ |
| FCN30 | : UAGGAGCCUAGCAGCC-CCUGCAUC-GA---UCACUAGGAUGGUU | 59 | * | % | $ |
| FCN38 | : AAAGUGUAGC-CUU-CCUGGA-CUGUAGGU-ACUAGGACGGUCC | 60 | * | % | @ |
| FCN44 | : ACAAAUGU-GC-UCC-CUUGGA-C-GAAGUUAACUCGG-CGG | 61 | * | % | $ |
| FCN55 | : AAGAAGCUG-GC-GAC-AGGCGA---AAAGCAGACU-UGAGGGGAA | 62 | o | % | @ |
| FCN72 | : AGUAG-GU-GA-GGCUUCUGGA-CUGAAG-UAACUAGGUCGGUUC | 63 | * | % | @ |
| score 0.339752 | | | | | |
| FC8 | : CAUGA-GCUGCUGGACCAAA-CAGAUG-GAGG---AACCA-CCGUGU | 64 | * | | |
| FC39 | : GA-GCU-CUUGACGAAAACCUAUGCGAGAUGGAUACU-CGGUU | 65 | | | |
| FC40 | : GA-GCU-CUUGACGAAAACCUAUGCGAGAAGGAUACU-CGGUU | 66 | | | |
| FC41 | : GA-GCU-CUAGACGAAAACCUAUGCGAGAUG-AUACU-CGGUC | 67 | o | | |
| FC55 | : UGA-GCU-CUUGAAGAAGUCC-----GAAC---AUUCUCCUUUCUGCGACU | 68 | o | | |
| FC64 | : GA-GCUCCGGGAUCCAAGCG--UGCAACA---ACACU-AUGCCCAC | 69 | o | | |
| FC65 | : AAUAC-CCU-CGGGAACCAAUCC-----GACCCU-AUUUUGCAGUUUG | 70 | * | | |
| FCN59 | : AUGAUGCU-CCUGAAGUAAUCACCAG-GAC----AUCCU-CGGCAU | 71 | o | % | |
| FC9 | : GCAAU--CU-CGGACUAGACCAACGACCUUCGUUUGACGCUC-A | 72 | o | % | @ |
| FC18 | : CCGAUUU--CU-AGGACG-GAUUUACG---GAGAAUUGAGUCGC-AAG | 73 | o | | |
| MOTIF I score 0.262803 | | | | | |
| FC38 | : A-CGG-CGAGAAUGACAAU-GUUAUUCUACGAGCGAAGGAUUA | 74 | | | |
| FC50 | : GCAAU--CU-CGGACUAGACUAACGACCUUGGUUUGACGCUA-A | 75 | * | # | $ |
| FC51 | : GCAAU--CU-CGGACUAGACUAACGACCUUCGUUUGACGCUC-A | 76 | * | # | $ |
| FC60 | : AGAGCAGCGGAGGUGUGAGCUCUGACUCUG--AACAGCUG | 77 | o | | |
| FC76 | : CGGGAUUU--CU-CGGAAAAGACUAACGAC--UAAUUCCAGAACC | 78 | o | | |
| FCN11 | : GCAAU--CU-CGGACUAGGCUAACGACCUUUGUUUGACGCUC-A | 79 | * | # | |
| FCN14 | : GCAAU--CU-CGGACUAGACUAACGACCUUCGUUUGACGCUU-A | 80 | * | # | $ |
| FCN26 | : UC--CA-AGGACCAAACGGUGUUCGGCAGUGGACU-UU-AGCAA | 81 | o | # | |
| FCN28 | : UGGGCUAC--AU-GUGAGUACACCAGCGUGAGAGUUCUUAGG | 82 | o | # | |
| FCN29 | : CUGUGCAGUAACUGCGGAUGAGACCAACCGG-AUGGCUCAAC | 83 | ● | # | |
| FCN57 | : ACAAU--CU-CGGACUAGACUAACGACCUUCGUUUGACGCUU-A | 84 | * | # | |
| FCN61 | : GCAAU--CU-CGGACGAGACUAACGACCUUCGUUUGACGCUU-A | 85 | * | # | |
| FCN65 | : AGCGCUAGAUGGACGAGAGACUUUUAAGUAGC-AAGCGGUA | 86 | * | | |
| score 0.274690 | | | | | |
| FC10 | : CAGACUCAGAGCGCCGUGAGCUUCUGAAG-CAA--UCGCAGGU | 87 | * | # | |
| FC53 | : G-CGGGGAGCUCCUCGAGAAACUGAGUUCAACUUCCCAGGU | 88 | o | # | |
| MOTIF III score 0.387597 | | | | | |
| FC14 | : GUGUUGGAGCUCUUGAUUGGAAAAG---UAGA--ACAAAUCGAAA | 89 | * | # | $ |
| FC30 | : GUGUUGGAGCUCUUGAUUGGAAAAU--UAGA--GCAAAUCGAAA | 90 | * | # | $ |
| FC49 | : CAAUCCGAGCUCUUGAA-GCAAUCC--UUGAUUGCAAGAUGAU | 91 | o | | |
| FC52 | : UCGGAUG-AGCUCUUGAA-GCAGUUC--AAGG--ACAGACAUAAAG | 92 | * | | |
| FC59 | : UUCCAGGU-UAGCGGCCAAACC--UCGA-CUUGAACAGACUUUA | 93 | o | | |
| FC70 | : GUGUUGGAGCUCUUGAUUGGAAAAG--UAGA--GCAAAACGAAA | 94 | * | # | $ |
| FC74 | : GUGUUGGAGCUCUUGAUUGGAAAAG--UAGA--GCAAAUCGAAA | 95 | * | # | $ |

TABLE 5-continued

Fibrin-Binding Clones

| FINAL CLUSTERS | | SEQ ID NO | In Vitro Clot Binding | Fibrinogen Affinity | Binding PE Assay |
|---|---|---|---|---|---|
| FCN2 | : GUGGUGCUGCAAUUGCUCGGUCGGC---GUGCUCUCUACUUGA | 96 | | | |
| FCN3 | : GCUCAAGAGACUGAA-GGAAAAGCUUAGAGCUCAAAGC-AUA | 97 | | | |
| score 0.306520 | | | | | |
| FC22 | : CGUGUUGGGUUCAAAGACCAGCUUACGGUACACAGUACGA | 98 | o | | |
| FCN31 | : UC-UGUUGG-UUCAAAGACUUGCUAAGGGGUCGAAGCACCCU | 99 | * | / | |
| score 0.492063 | | | | | |
| FC24 | : GAC-GACAAAG-AGUCCGUUC-CAAACCUC-UGAGACAGGGU | 100 | o | | |
| FCN8 | : U-AGCAAGUCCCACAUCCCAGACGGG-CUAAAAAGAGGUGGA | 101 | o | % | |
| FCN18 | : AUGAAC--GACCGCGG--GCAGUCGCGU-UCAAAUGAG-UGGUUUU | 102 | ● | % | |
| FCN24 | : AUGAGUA-GACCGAGGAAGCACCCGGCUCUCAAAUGAG-UGA | 103 | * | / | |
| FCN64 | : AUGAGUA-GACCGAGGAAGCACCCGGCUCUCAAAUGAC-UGA | 104 | o | / | |
| score 0.294667 | | | | | |
| FC25 | : AAGGCC-AU--CAGGGCAAAGACCUCCUAGGUACUGA-CGCUUA | 105 | o | | |
| FC34 | : AAGGCCGAA--CAACGAAGUUUGAUUC-AGGUACUCAGCG-UUC | 106 | o | % | |
| FC35 | : AAGGCCGAA--CAACGAAGAUUGAUUC-AGGUACUCAGCG-UUC | 107 | o | | |
| FCN34 | : AAGGCGGAGGGCAAGCAAGA-ACCU-C-ACGAACAGA-CG-UUAA | 108 | ● | | |
| score 0.428395 | | | | | |
| FC33 | : AGCCUGAGGUAUAGUU---ACG-CU-AUAUGGGA---GGUAGGCUUUA | 109 | * | | |
| FCN13 | : CGUGAUG-ACAGCUCGGACGGCUCAU-UGCGCGGAGUAG-CUA | 110 | * | % | @ |
| FCN56 | : CGGCUCGAUG-CUAGCUGGGACGGCUCAU-UGAGACUGGUUG | 111 | ● | % | |
| score 0.324074 | | | | | |
| FC42 | : AGUGCAACCU-GAACCAAACCAAACUAGCGCGCAGUUGGGU | 112 | o | | |
| FCN36 | : AGCAGAUGGUGCUGAGGUAU-CAU-GAAGACGCUGAC-GCUUA | 113 | ● | / | |
| FCN49 | : GAAUGGAGCCAAGAAAGACAGCGAUGUCUCGGAC-GAUGAG | 114 | o | % | |
| FCN50 | : GAAUGGAGCCAGGAAAGACAGCGAUGUCUCGGAC-GAUGAG | 115 | * | / | |
| FCN58 | : GGAUGGAGCCAAGAAAGACAGCGAUGUCUCGGAC-GAUGAG | 116 | o | % | |
| FCN67 | : CGUG-AGAUUCCCCUGCGUAAGACCA-GAAGACUAUCAG-GCU | 117 | | | |
| score 0.335225 | | | | | |
| FC43 | : AGGGUUGAGGCUUAUCCUUCUUUCGUUCGUGACACGAUCG | 118 | * | | |
| FCN69 | : GAUUGACACGCA--CUCCAAUGGCUC-UGAAGUGUUCGUGUGC | 119 | ● | % | |
| score 0.296296 | | | | | |
| FC46 | : AAAUUCAAUGCUCUGAUGGGUUUAUGAGUUAAUGCGU-GGAC | 120 | o | | |
| FC61 | : AAAGCCCCU-UUCAGCAGGGAUC---GAGGUACUGGAU-GGAUA | 121 | o | | |
| FCN27 | : AAAGUCG-UGUGC-GAGAGGCUCA-GAUUUAAUGCGGAGGA | 122 | o | % | |
| score 0.343669 | | | | | |
| FCN9 | : CGUU-GAAAUCGCUCCUCAGU-G-UGAGUUGAAUCAGCUGACC | 123 | ● | % | |
| FCN21 | : AGUUUGGAUUCG-GCAGGUGCUG-AGACUUUGAU-AGCC-ACUA | 124 | ● | % | |
| FCN22 | : GUGAGAAAU-G-UCGGGGGC-GAUGACUUGGA-CGACCACCG | 125 | ● | % | |
| FCN60 | : CGUU-GAAAUCGCUCCUCAGC-G-UGAGUUGAAUCAGCUGACC | 126 | | | |
| score 0.376263 | | | | | |
| FCN12 | : AGAGAGGAACUGCGAUUCAGACCAAAACGGA---AAUGGCUGU | 127 | ● | % | |
| FCN25 | : GAUAUACUAACUUUCUUUGAAAGCCAAAAGUAUUAAUG-CG | 128 | * | % | |
| FCN48 | : GAUAUACUAACUUUGUUUGAAAGCCAAAAGUAUUAAUG-CG | 129 | * | / | $ |
| FCN52 | : AGCCGAGCUAAUCCCGAAAGUGACCCGGAACGACG-CGGCA | 130 | o | % | |
| score 0.363636 | | | | | |

Table 5 KEY o-low in vitro clot binding

●-moderate in vitro clot binding

*-high in vitro clot binding

%-low fibrinogen affinity, Kd > 1 mM

/-moderate fibrinogen affinity

-high fibrinogen affinity, Kd < 1 mM

@-low binding PE assay $-high binding PE assay

TABLE 6

Truncation Analysis

| | SEQ ID NO: |
|---|---|
| FC #69                                               boundary<br>gggagacaagaauaaacgcucaaACAAAUGUGCGCCCUUGGAC<u>GAAGUUAACUCGGACGGUUC</u>uucgacaggaggcucacaacaggc | 55 |
| 69.1 (25)<br>                                                             CGAAGUUAACUCGGACGGUUCuucg | 131 |
| 69.2 (29)<br>                                                CGAAGUUAACUCGGACGGUUCuucgacag | 132 |
| 69.3 (29)<br>                                      UGGACGAAGUUAACUCGGACGGUUCuucg | 133 |
| 69.4 (41)<br>                        CCCUUGGACGAAGUUAACUCGGACGGUUCuucgacaggagg | 134 |
| FCN #30                                            boundary<br>gggagacaagaauaaacgcucaaUAGGAGCCUAGCAGCCCCUGC<u>AUCGAUCACUAGGAUGGUU</u>uucgacaggaggcucacaacaggc | 59 |
| N30.1 (23)<br>                                                      UCGAUCACUAGGAUGGUUuucga | 135 |
| N30.2 (30)<br>                                                UCGAUCACUAGGAUGGUUuucgacaggagg | 136 |
| N30.3 (31)<br>                                   CCCCUGCAUCGAUCACUAGGAUGGUUuucga | 137 |
| N30.4 (38)<br>                             CCCCUGCAUCGAUCACUAGGAUGGUUuucgacaggagg | 138 |

```
                              A—C                                    C—U
5'-C—G—A—A—G···U—U—A A   U         U—C—G—A···U—C—A        A
3'-g—c—u—u—C      G—G—C   C         a—g—c—u      G—G—U      G
            UU         A—G G                 uUU        A—G
         69.1 (25)                         N30.1 (23)
```

45

TABLE 7

Rat Carotid Artery SELEX

| Round | Method | Buffer | [2'F-40N8], uM | % bound | Discrimination injured/norm |
|---|---|---|---|---|---|
| | *Ex Vivo* | | | | |
| 1 | minced | Ringers lact. | 5 | 6.7 | n.a. |
| 2 | minced | Ringers lact. | 2 | 2.7 | n.a. |
| 3 | minced | Ringers lact. | 3.4 | 6.9 | n.a. |
| 4 | perfused. inj. | Ringers lact. | 2.5 | 0.2 | n.a. |
| 5 | perfused. inj. | Ringers lact. | 5.9 | 0.6 | n.a. |
| 6 | perfused. inj. | Ringers lact. | 2.3 | 0.62 | n.a. |
| 7 | perfused. inj. | Ringers lact. | 2.3 | 0.7 | n.a. |
| 8 | perf. normal | Ringers lact. | 0.75 | 0.54 | |
| | injured | Ringers lact. | 0.75 | 1.04 | 1.9 |
| 9 | perf. normal | PBS | 0.75 | 0.02 | |
| | injured | PBS | 0.75 | 0.07 | 3.3 |
| 10 | perf. normal | PBS | 0.75 | 0.1 | |
| | injured | PBS | 0.75 | 0.5 | 4.5 |

TABLE 7-continued

Rat Carotid Artery SELEX

| Round | Method | Buffer | [2'F-40N8], uM | % bound | Discrimination injured/norm |
|---|---|---|---|---|---|
| 11 | perf. normal | PBS | 0.75 | 0.1 | |
| | injured | PBS | 0.75 | 0.35 | 3.4 |
| 12 | perf. normal | PBS | 0.75 | 0.1 | |
| | injured | PBS | 0.75 | 0.34 | 3.4 |
| | *In Vivo* | | amount injected, nmoles | | |
| 13 | in vivo | PBS | 3 | 0.01 | 2.61 |
| 40N8(control) | in vivo | PBS | 3 | n.a. | 1.16 |
| 14 | in vivo | PBS | 3 | 0.02 | 4.06 |
| 15 | in vivo | PBS | 3.8 | 0.02 | 0.94 (not flushed) |
| 15 | ex vivo | PBS | 3.8 uM | n.a. | 4.61 |
| 16 | in vivo | PBS | 3.9 | 0.005 | 3.54 |

TABLE 8

| MOTIF I | FINAL CLUSTERS | SEQ ID NO | INTENSITY OF STAINING | BINDING SPECIFICITY |
|---|---|---|---|---|
| p3 : | gggagauaaga-auaa-acgcu-caa | 139 | | |
| p5 : | uucgacaggaggcucacaacaggc | 140 | | |
| C4 : | ACCA-CUGGGC-CCAG-UUUAG-AAA---CU-CAUU-----GCCCAAAUCCGG | 141 | | |
| C13 : | AAG--AAGA-AUCG-AAAAAUCUAC--CUUGUUC-GGAGCCUGCUCU | 142 | + | ns |
| C15 : | U-CUAG-AC-AG-CGAAGGCUGAGCUAUGACACUGAACUUCUUA | 143 | − | |
| C22 : | GCAAUCU-GGA-CUAG-ACUAA-CGAC--CUUCGCU-UGACGCUCA | 144 | | |
| C26 : | GCAAUCUCGGA-CUAG-ACUAA-CGAC--CUUCGUU-UGACGC--AAU | 145 | | |
| C33 : | GCAAUCUCGGA-CUAG-ACUAA-CGAC--CUUCGUU-UGACGCUCA | 146 | ++ | s |
| C38 : | GCAAUCUCGGA-CUCG-ACUAA-CGAC--CUUCGUU-UGACGCUCA | 147 | | |
| C53 : | GACAAUAACCGC------ACCAA-CGUU--CU--GUU-CUUCGCUUGCACGU | 148 | − | |
| C57 : | CAAU-UCCCA-CU-G-AUUCG-GGGC---GGUCCUUGCGAUGGCGAGA | 149 | | |
| C59 : | CUCAGA-CAACCAACAG-CA-C--GUUC-UC-UGUU-UUCGUCGUUUG | 150 | +++ | s |
| C60 : | GCAAUCUCGGA-CUAG-ACUAA-CGAC--CUUCGUU-UGACGCUUA | 151 | | |
| C72 : | GCAAUCUCGGA-CUAG-ACUAA-CGAC--CUUCGUU-UGACGCUCG | 152 | | |
| Civ3 : | CGCU-CAUG-ACCAGGCGCUA-CUGACUG-AGAUGUUGAACUUA | 153 | − | |
| Civ14 : | GCAAUCUCGGA-CUAG-ACUAA-CGAC--CCUCGUU-UGACGCUCA | 154 | | |
| Civ27 : | AUAAGAUCAAC-AUUGG-CG----GUU---UA-UGUUAUUCGUCCGUUUG | 155 | | |
| Civ30 : | GCAAUCUCGGA-CUAG-ACUAA-CGAG--CUUCGUU-UGACGCUUA | 156 | | |
| Civ34 : | CACGCGAGAG-CU---UCUAA-AGCU--GCUGAAU-CGA-GCUCCACGA | 157 | | |
| Civ41 : | ACAAUCUCGGA-CUAG-ACUAA-CGAC--CUUCGUU-UGACGCUUA | 158 | +++ | ns |
| Civ42 : | GCAAUCUCGGA-UUAG-ACUAA-CGAC--CUUUGUU-UGACGCUCA | 159 | | |
| Civ48 : | GCAAUCUCGGA-CUAG-ACUAA-CGAC--CUUCGUA-UGACGCUUA | 160 | | |
| Civ50 : | GCAAUCUCGGA-CUAG-ACUAA-CGAC--CUUCGCU-UGACGCUCA | 161 | | |
| Civ53 : | GGAGAUCCUCGA-GGAA-ACU---CGAC-CUUCUUCCCGACGUUGA | 162 | | |
| Civ59 : | ACAGCUCGGA-UAAG-ACUAA-CGAC--CU-AGUU-UG--GCUAAGCAA | 163 | ++ | ns |
| Civ65 : | GCAAUCUCGGA-CUAG-ACUAA-CGAC--CUUCGUU-UGACGCUCA | 164 | | |
| score 0.268867 | | | | |
| C1 : | ACAAGGGAGUCGGUUUAU-UCAGCCUG-UUCGGAACCUGACU | 165 | + | ns |

TABLE 8-continued

| MOTIF I | | FINAL CLUSTERS | SEQ ID NO | INTENSITY OF STAINING | BINDING SPECIFICITY |
|---|---|---|---|---|---|
| C44 | : | AUCCAAGACGCUUAGU---UCUUGCUC-UUCGGGGCUUC-CUA-CG | 166 | | |
| C45 | : | AAGUAAACUCGAGACCGUUCUGGCUGAUUCGGGGC-ACUCU | 167 | | |
| C55 | : | ACUUGACAA-UCCCCCUGAUUCGGGGCCUGACUAUCACGA | 168 | ++ | ns |
| C58 | : | ACACGACA-UCGAAGUUA-UCCCCCUGAUUCGGAGCCAG-CUG | 169 | − | |
| C65 | : | AGCUGGAAA-UCCAAAUGC-UUUGUCUAGUU-GGGGC---CACUU | 170 | | |
| C67 | : | AGACUCUUGAUCA-UCCCCCUAGUUCGGGGC-UGACUG-CACU | 171 | | |
| Civ6 | : | ACUUGACAA-UCCCCCUGAUUCGGGGCCUGACUAUCACGAU | 172 | | |
| Civ24 | : | GGAGCGAAAUUCUUGAAUA-UCC-ACUGAUUCGGACCGUC-CU | 173 | − | |
| Civ29 | : | GCGGGAUUUUCCUGAUCA-UCCCACUGAUUCGGGGCCUUAG | 174 | | |
| Civ31 | : | AGUUUCUCCUUGGCAA-UCCCCCCUAUUCGGGGCUUCAUUG | 175 | | |
| Civ55 | : | GAGCGAAAUUCUUGAAUA-UCC-ACUGAUUCGGAGCGUC-CU | 176 | | |
| Civ56 | : | ACGGCAUUCUAAACAU-UCCCCCUUGUUCGGAGCCACUCU | 177 | | |
| Civ62 | : | GCGGA-UUUUGAUCA-UCCCCCUGAUUCGGAGAC-CUCUUAC | 178 | − | |
| score 0.286720 | | | | | |
| C3 | : | GGGAACGAAUCGUCCAAAA--GA-CCUCGCGGAAUCGGC-G-UUA | 179 | + | ns |
| C17 | : | GCGAGCUCUU-GCACAAAACCGAUCCUCGC--AUACAGCAGGU | 180 | − | |
| C30 | : | GGGAACGAAUCGUUCAAAA--GA-CCACGCG-AAUCGGC-GCUUA | 181 | | |
| score 0.441975 | | | | | |
| C10 | : | GAGCUGUUGACGAAAACUUAUGCGGAGAU--GGAUA-CUCGGU | 182 | + | s |
| C27 | : | GAGCUCUUGACGAAAACCUAUUCG-AGAU--GGAUA-CUCGGUU | 183 | | |
| C35 | : | GGAGCCGAUUG-UACAACCUAGGUG-AGCU---CAAU-CACCUCGC | 184 | | |
| C36 | : | GGGCCCUCUGCUACAACUUCGGCA-AGGA---CAUU-UUCCGGAC | 185 | | |
| C37 | : | GAGCUCUUGACGAAAACCUAUGCG-AGAU--GGAUA-CUCGGUU | 186 | + | ns |
| C49 | : | GAAAGC-CAUGUUGAAAGUUUCACCC-AGAUUCGGA---GUCGUUG | 187 | ++ | ns |
| C62 | : | ACUGAGCUCGUGU--ACAA--UGUUAG-GGAA--GGACAUCUCGAUA | 188 | | |
| C66 | : | GAGCUCUUGACGAAAACCUAUGCG-AGAA--GGAUA-CUCGGUU | 189 | | |
| C69 | : | GAGCUCUUGACGAAAACCUACGCG-AGAU--GGAAA-CUCGGUU | 190 | | |
| Civ32 | : | CACAGGGGUUUC---AAACCUCCCCC-UGAUUCGGAGC-UUC | 191 | | |
| Civ38 | : | AACCUCGCGAGGAAUAACU-UGCG-ACUUUCGGAUC-GUCUUUA | 192 | + | ns |
| Civ54 | : | GAGCUCUUGACGAAAACCUAUGCG-AGAU--GGAUA-CUCGGUU | 193 | | |
| Civ64 | : | CUUUGGAGCUCCUGG----AACGAAAGCG-GAAU---UAAC-UUCCUUA | 194 | | |
| score 0.303419 | | | | | |
| C11 | : | ACAAUUCAGGACGGGG---UUUCUU---GAAUG--GGUUCGACCUU-CA | 195 | | |
| C52 | : | CCAGUA-GAUCAA-CUCCCUGGCAACU---GGUUCGCCGUUAUA | 196 | | |
| Civ5 | : | A-CCUUGAUGUUCA--CUCCCU---AACUCAAGGUUCGACGUC-UA | 197 | | |
| Civ33 | : | ACAA-CCUGGACAAGGAAUUUUUCU----AGUGUUCGUUGGACGU | 198 | ++ | s |
| Civ35 | : | A-CCUUGAUGUUGAA-CUCCCU---AACUCAAGGCUCGACGUC-UA | 199 | ++ | s |
| score 0.301361 | | | | | |
| C19 | : | ACGAAGGCAACUUCA-AACAUUCCUUACGUUCCG-CGCUCA | 200 | | |
| C51 | : | ACGGCGCCAACAGCG-AAUGUUCGCCC-CGUUCGGACGCUUA | 201 | | |
| Civ45 | : | ACCGACACAACCACG--ACGUUCGGUC-G<u>GUUUG</u>UCCGAUUA | 202 | +++ | s |

TABLE 8-continued

| MOTIF I | FINAL CLUSTERS | SEQ ID NO | INTENSITY OF STAINING | BINDING SPECIFICITY |
|---|---|---|---|---|
| Civ63 : | ACGGAGGCAAVVAAG--AGAUUCCAU-CGUUCGUUCGAUUGA | 203 | | |
| Civ70 : | UCC-AUCCAACGCGGCAAGAUUUGAUG-GACUUUGACGAUCA | 204 | | |
| score 0.326357 | | | | |
| C23 : | AA-GCU--CAGC-AGAUCGGGACUUCUGAUCUUCGGGUCGCUUA | 205 | − | |
| Civ67 : | CAACGGUAGCGGCUAGAACGCGCCGACUGAU-UUAGG----CUUA | 206 | | |
| score 0.362963 | | | | |
| C28 : | UCCUCCUG-UUCG-GAGUCUCAAUGUCGACUCGGCCGGACCU | 207 | | |
| Civ12 : | AGA-AAUCCCCUUGAUUCG-GAGUCGUCUUUUCGAG-CGUAGU | 208 | + | ns |
| Civ26 : | AGA-AAUCCCCUUGAUUCG-GAGUCGUCUUUUCGAG-CGAAGG | 209 | | |
| Civ37 : | GAGAGUCAAC-UG---CGAGAAUGG-CUUUCCCAA-CGGCACCUUU | 210 | +++ | s |
| Civ40 : | AGAUAAUCCCCCGGAUUCG-GAGUCCUCUUGACGAA-CUUCC | 211 | | |
| score 0.356944 | | | | |
| C29 : | C-GGA-ACAAACGGAAAUGGCACACAGG-AGAAAGACGAGACC | 212 | | |
| C34 : | CAGGAGAUUAA-GGAACAGGC-CACAGAUAGAGACACG-GAGC | 213 | | |
| score 0.426357 | | | | |
| C31 : | AACUGGACGAGAGGAGCUAGCGUCCAAGUUCGGAGCUA | 214 | + | ns |
| Civ44 : | ACUGAUUCUCAGCGGCUAGCGCUGAAGUUCG-A-CUAGUUCA | 215 | | |
| score 0.410853 | | | | |
| C39 : | GGCCACAAGCAG-AGAACAGAACAA-CAGAGCGAUGGAG-AGA | 216 | | |
| C50 : | GGAG-CAUCCAGGAUAACAGGCUAAACACCGCAA-GGACCAG | 217 | | |
| score 0.333333 | | | | |
| C46 : | CGGAGGAAGGAAGAGG--AACCUUCGC-CUCUGAUUUAGCUUA | 218 | | |
| C68 : | CGUGGGCAAACUGAGG-CAUUCCCCGCGCUCAGAGAUUCAU | 219 | | |
| C71 : | CAAUGGCAACUAGGCCACAAAGUUC-C-CACUGAUUCGACGU | 220 | | |
| Civ19 : | GCAAUCGGACCGAAAGG----CCUUACC-GAUUUCUCGACCUUUC | 221 | +++ | ns |
| Civ43 : | CGGAGGAAGGAAGAGG--AACCUUUGC-CUCUGAUUUAGCUUA | 222 | | |
| Civ47 : | CGGAGGAAGGAAGAGG--AACCUUCGC-CUCUGAUUUAGCUUA | 223 | | |
| Civ57 : | AGUCGAGUUUCAAGG--AUCAUCCCC-CUCUUCGGAGCCUUUC | 224 | | |
| Civ58 : | CGGAGGAAGGAAGAGG--AGCCUUCGC-CUCUGAUUUAGCUUA | 225 | | |
| score 0.347884 | | | | |
| C56 : | CGAGGCCACCGACAAGGAAGUCG---ACCG-GAGUUGAAGUAAA | 226 | | |
| Civ39 : | GGCC-CCUAGCGGGAUGCCGCUAAUCGCGAAUCGAGGUUUA | 227 | | |
| score 0.348485 | | | | |
| Civ7 : | UCGAUGCU--AUC-GAGUUCU-ACUCGGAAGGUUC-AACGUUUAA | 228 | ++ | s |
| Civ9 : | CCCAUACU-GAGA-AAGAACAGACUUCUCAGGUUCGAACGU | 229 | | |
| Civ13 : | CCUGAGACG-GUAC-GAGUUCGGACUC---AGGAUUUAACGCUUU | 230 | | |
| Civ15 : | CUUACUCAACCU-GCGA-ACGCACAG-GUU---AG-UUC-ACCGUUUA | 231 | | |
| Civ17 : | ACCCACACU-GAGA-AAGAACAGACUCCACAGGUUCGAACGU | 232 | | |
| Civ36 : | AAACUCAUUCU-GAGCUAAGCUCA-AGUUC-----UUGCAACGUUUG | 233 | | |
| Civ49 : | ACCGAUUCUCGAAG-CAGCACG--CUCC--AGG-UCUGACGUUUU | 234 | | |
| Civ66 : | ACCUAUACU-GAGA-AAGAACAGACUUCUCAGGUUCGAACGU | 235 | | |

TABLE 8-continued

| MOTIF I | FINAL CLUSTERS | SEQ ID NO | INTENSITY OF STAINING | BINDING SPECIFICITY |
|---|---|---|---|---|
| score 0.316084 | | | | |
| Civ8 : | AGGAACUUAUUCGAC---AUCAG-UCGGUUCCCUGGACGGGUUG | 236 | | |
| Civ51 : | GAACCUAUUCAACCGGAUUAGGUUGGUUCUC-GGAUGUCUA | 237 | | |
| score 0.439394 | | | | |

TABLE 9

Carotid Truncates and Putative Structures

```
G A        UC              C        A
  C C U  G U U U G  A G C U   C  u  g a
 g g  a  c a a a c  u c g g      ag a   c
                 c                   g
```
C12.1
(C33 truncate)
(SEQ ID NO: 238)

```
G A        UC              C        A
  C C U  G U U U G  A G C U U u  u  c  g
 g g  a  c a a a c  u c g g a g g a c   a
                 c
```
(Civ41 truncate)
(SEQ ID NO: 239)

TABLE 9-continued

Carotid Truncates and Putative Structures

```
            U
         G C           C
  C G   G   G         U G U   A
      U U C  G U U U G  A U U u  u  c  g  a
     g g    a  c a a a c  u g g a g g a c
                     c                 c
```
(Civ45 truncate)
(SEQ ID NO: 240)

```
              G
     G U C  U U U G  u  u c
          c  g g g a c  a  g
                    a
```
(C59 truncate)
(SEQ ID NO: 241)

We claim:

1. A method for identifying nucleic acid ligands to a target selected from the group consisting of peripheral blood mononuclear cells, fibrin clots, and carotid arteries comprising:

a) preparing a candidate mixture of nucleic acids;

b) contacting said candidate mixture of nucleic acids with said target, wherein nucleic acids having an increased affinity to the target relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acids with relatively higher affinity and specificity for binding to said target than the remainder of the candidate mixture, whereby nucleic acid ligands of said target may be identified.

2. The method of claim 1 further comprising:

e) repeating steps b), c) and d).

3. The method of claim 1 wherein said candidate mixture is comprised of single-stranded nucleic acids.

4. The method of claim 3 wherein said single-stranded nucleic acids are ribonucleic acids.

5. The method of claim 3 wherein said single-stranded nucleic acids are deoxyribonucleic acids.

6. A method for identifying a nucleic acid ligand to a target selected from the group consisting of peripheral blood mononuclear cells, fibrin clots, and carotid arteries comprising:

a) preparing a candidate mixture of nucleic acids;

b) contacting said candidate mixture with a first target selected from the group consisting of peripheral blood mononuclear cells, fibrin clots, and carotid arteries, wherein nucleic acids having an increased affinity to the first target relative to the candidate mixture may be partitioned from the remainder of the candidate mixture;

c) partitioning the increased affinity nucleic acids from the remainder of the candidate mixture;

d) contacting the increased affinity nucleic acids with a second target, structurally related to said first target, wherein nucleic acids with affinity to the second target are removed;

e) amplifying the remaining nucleic acids to yield a mixture of nucleic acids enriched for nucleic acids with relatively higher affinity and specificity for binding to said first target; and f) identifying said nucleic acid ligand of said first target.

7. A method for identifying a nucleic acid ligand to a target selected from the group consisting of peripheral blood mononuclear cells, fibrin clots, and carotid arteries comprising:

a) preparing a candidate mixture of nucleic acids;

b) contacting said candidate mixture with a first target, structurally related to a second target, wherein nucleic acids with affinity to the first target are removed;

c) contacting the candidate mixture from b) with said second target selected from the group consisting of peripheral blood mononuclear cells, fibrin clots, and carotid arteries, wherein nucleic acids having an increased affinity to the second target relative to the candidate mixture may be partitioned from the remainder of the candidate mixture;

d) partitioning the increased affinity nucleic acids from the remainder of the candidate mixture;

e) amplifying the remaining nucleic acids to yield a mixture of nucleic acids enriched for nucleic acids with relatively higher affinity and specificity for binding to said second target; and f) identifying said nucleic acid ligand of said second target.

* * * * *

SEQUENCE LISTING ( 1 ) GENERAL INFORMATION:

( i i i ) NUMBER OF SEQUENCES: 241

( 2 ) INFORMATION FOR SEQ ID NO:1:

( i ) SEQUENCE CHARACTERISTICS:
  ( A ) LENGTH: 72 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

AGGGAGGACG ATGCGGNNNN NNNNNNNNNN NNNNNNNNNN NNNNNNNNNN  50

NNNNNNCAGA CGACTCGCCC GA  7 2

( 2 ) INFORMATION FOR SEQ ID NO:2:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2:

AGGGAGGACG ATGCGG    16

( 2 ) INFORMATION FOR SEQ ID NO:3:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) FEATURE:
  ( D ) OTHER INFORMATION: N at position 1 represents 3
   biotins ( x i ) SEQUENCE DESCRIPTION: SEQ ID NO:3:

NTCGGGCGAG TCGTCTG    17

( 2 ) INFORMATION FOR SEQ ID NO:4:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:4:

CCGAAGCTTA ATACGACTCA CTATAGGGAG GACGATGCGG    40

( 2 ) INFORMATION FOR SEQ ID NO:5:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:5:

GCCGGATCCT CGGGCGAGTC GTCTG    25

( 2 ) INFORMATION FOR SEQ ID NO:6:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:6:

TTCACACAGG AAACAG    16

( 2 ) INFORMATION FOR SEQ ID NO:7:

( i ) SEQUENCE CHARACTERISTICS:
  ( A ) LENGTH: 71 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:7:

AGGGAGGACG ATGCGGGGG TCGGTTCGGG CATATAGGGT ATTCTTCGTA    50

GAGGGCAGAC GACTCGCCCG A    71

( 2 ) INFORMATION FOR SEQ ID NO:8:

( i ) SEQUENCE CHARACTERISTICS:
  ( A ) LENGTH: 71 base pairs ( B ) TYPE: nucleic acid
( C ) STRANDEDNESS: single
( D ) TOPOLOGY: linear ( x i ) SEQUENCE DESCRIPTION: SEQ ID NO:8:

```
AGGGAGGACG ATGCGGGGGG TCGGTTCGGG CATATAGGGT ATTCTTCGTA      50

AAGGGCAGAC GACTCGCCCG A                                    71
```

( 2 ) INFORMATION FOR SEQ ID NO:9:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AGGGAGGACG ATGCGGGGGG TCGGTTCGGG CATATAGGGT ATCCTTCGTA      50

GAGGGCAGAC GACTCGCCCG A                                    71
```

( 2 ) INFORMATION FOR SEQ ID NO:10:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
AGGGAGGACG ATGCGGCACG TTAGTAGGAT TAGGATTATT CAGGTTGTAG      50

GGAACACAGA CGACTCGCCC GA                                   72
```

( 2 ) INFORMATION FOR SEQ ID NO:11:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGGGAGGACG ATGCGGCACG TTCAGCAGGA TTAGGGTTGT TTNGGTTGTA      50

GGGACACACA GACGACTCGC CCGA                                 74
```

( 2 ) INFORMATION FOR SEQ ID NO:12:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AGGGAGGACG ATGCGGCACG GTAGTAAGTA GTAGGGTATT ATAATTAGGG      50

GATCCACAGA CGACTCGCCC GA                                   72
```

( 2 ) INFORMATION FOR SEQ ID NO:13:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AGGGAGGACG ATGCGGCACG GCAGTATTAT TCAGGGGTCT TAGATATTAG        50

GGGGCACAGA CGACTCGCCC GA        72

( 2 ) INFORMATION FOR SEQ ID NO:14:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AGGGAGGACG ATGCGGCACG GTAGGTTTTA GATAGGGATA TTTGGTGTAG        50

GGAGCACAGA CGACTCGCCC GA        72

( 2 ) INFORMATION FOR SEQ ID NO:15:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

AGGGAGGACG ATGCGGCACG GTAGGTTATA GATAGGGATA TTTNTTGTAG        50

GGAACACAGA CGACTCGCCC GA        72

( 2 ) INFORMATION FOR SEQ ID NO:16:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AGGGAGGACG ATGCGGCACG GTAGGTTTTA GATAGGGATA TTTGATGTAG        50

GGAGCACAGA CGACTCGCCC GA        72

( 2 ) INFORMATION FOR SEQ ID NO:17:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AGGGAGGACG ATGCGGCACG GTAGGTTTTA GATAGGGATA TTTGGTATAG        50

GGAGCACAGA CGACTCGCCC GA        72

( 2 ) INFORMATION FOR SEQ ID NO:18:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AGGGAGGACG ATGCGGCACG GTAGGCTTTA GATAGGGATA TTTGATGTAG        50

GGAGCACAGA CGACTCGCCC GA        72

( 2 ) INFORMATION FOR SEQ ID NO:19:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
AGGGAGGACG  ATGCGGGGGG  AGTAGGGTAT  TTAAAAATGT  TAGGGTAAGT        50
TTCCTCCAGA  CGACTCGCCC  GA                                        72
```

( 2 ) INFORMATION FOR SEQ ID NO:20:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
AGGGAGGACG  ATGCGGGGGG  AGTAGGGTAT  TTAAAAGTGT  CAGGGTAAGT        50
TTCCTCCAGA  CGACTCGCCC  GA                                        72
```

( 2 ) INFORMATION FOR SEQ ID NO:21:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
AGGGAGGACG  ATGCGGCGTA  GTAAGAAGTA  TTATTAGGGA  TATTGTAGGG        50
GCGCTACAGA  CGACTCGCCC  GA                                        72
```

( 2 ) INFORMATION FOR SEQ ID NO:22:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AGGGAGGACG  ATGCGGCGTA  GTAAGAAGTA  TTATTAGGGA  TATTGCAGGG        50
GCGCTACAGA  CGACTCGCCC  GA                                        72
```

( 2 ) INFORMATION FOR SEQ ID NO:23:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
AGGGAGGACG  ATGCGGGGCA  GCAAGAGTTT  GATTAGGGTA  TAGTTAGGGG        50
CGCTGCAGAC  GACTCGCCCG  A                                         71
```

( 2 ) INFORMATION FOR SEQ ID NO:24:

( i ) SEQUENCE CHARACTERISTICS:
        ( A ) LENGTH: 71 base pairs (B) TYPE: nucleic acid
(C) STRANDEDNESS: single
(D) TOPOLOGY: linear (xi) SEQUENCE DESCRIPTION: SEQ ID NO:24:

AGGGAGGACG ATGCGGGCAG CAAGAGTTTG ATTAGGGTAT AGTTAGGGGC  50

GCTGCCAGAC GACTCGCCCG A  71

(2) INFORMATION FOR SEQ ID NO:25:

(i) SEQUENCE CHARACTERISTICS:
(A) LENGTH: 71 base pairs
(B) TYPE: nucleic acid
(C) STRANDEDNESS: single
(D) TOPOLOGY: linear (xi) SEQUENCE DESCRIPTION: SEQ ID NO:25:

AGGGAGGACG ATGCGGGCAG TAAGGGTTTG ATTAGGGTAT AGTTAGGGGC  50

GCTGCCAGAC GACTCGCCCG A  71

(2) INFORMATION FOR SEQ ID NO:26:

(i) SEQUENCE CHARACTERISTICS:
(A) LENGTH: 70 base pairs
(B) TYPE: nucleic acid
(C) STRANDEDNESS: single
(D) TOPOLOGY: linear (xi) SEQUENCE DESCRIPTION: SEQ ID NO:26:

AGGGAGGACG ATGCGGGCAG CAAGAGGTTG ATTAGGGTAT AGTTAGGGGC  50

GCTGCAGACG ACTCGCCCGA  70

(2) INFORMATION FOR SEQ ID NO:27:

(i) SEQUENCE CHARACTERISTICS:
(A) LENGTH: 72 base pairs
(B) TYPE: nucleic acid
(C) STRANDEDNESS: single
(D) TOPOLOGY: linear (xi) SEQUENCE DESCRIPTION: SEQ ID NO:27:

AGGGAGGACG ATGCGGCGGC AAGATGATTG AATAGGGGAT CTAAAGTTAG  50

GGGCGCCAGA CGACTCGCCC GA  72

(2) INFORMATION FOR SEQ ID NO:28:

(i) SEQUENCE CHARACTERISTICS:
(A) LENGTH: 72 base pairs
(B) TYPE: nucleic acid
(C) STRANDEDNESS: single
(D) TOPOLOGY: linear (xi) SEQUENCE DESCRIPTION: SEQ ID NO:28:

AGGGAGGACG ATGCGGGCAG CAGGTGTAGG GGTATAGATG GATAGGGATT  50

TCTTCTCAGA CGACTCGCCC GA  72

(2) INFORMATION FOR SEQ ID NO:29:

(i) SEQUENCE CHARACTERISTICS:
(A) LENGTH: 72 base pairs
(B) TYPE: nucleic acid
(C) STRANDEDNESS: single
(D) TOPOLOGY: linear (xi) SEQUENCE DESCRIPTION: SEQ ID NO:29:

```
AGGGAGGACG ATGCGGCACA TAGGGGAAAT GAGAATAGTA GGGTATTAAT        50

ACAGTGCAGA CGACTCGCCC GA                                     72
```

( 2 ) INFORMATION FOR SEQ ID NO:30:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
AGGGAGGACG ATGCGGCACA TAGGGGAAAT GAGAAGAATA GGGTATTAAT        50

ACAGTGCAGA CGACTCGCCC GA                                     72
```

( 2 ) INFORMATION FOR SEQ ID NO:31:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
AGGGAGGACG ATGCGGCAGG TTAGGGGAAA GGTTTAATAA TTAGGGTATA        50

AATGTGCAGA CGACTCGCCC GA                                     72
```

( 2 ) INFORMATION FOR SEQ ID NO:32:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
AGGGAGGACG ATGCGGCAGG TAGAGATAGG GAAGTTTTAT GTAGGGACA         50

ATTCGTCAGA CGACTCGCCC GA                                     72
```

( 2 ) INFORMATION FOR SEQ ID NO:33:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
AGGGAGGACG ATGCGGCAGG TAGAGATAGG GAAGTTTTAT GTAGGGACA         50

ATTCGTCAGA CGACTCGCCC GA                                     72
```

( 2 ) INFORMATION FOR SEQ ID NO:34:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
AGGGAGGACG ATGCGGCACA ATAGGGAAAT TTGTTGTTAT AGTTAGGGAT        50

ACTGGACAGA CGACTCGCCC GA                                     72
```

( 2 ) INFORMATION FOR SEQ ID NO:35:

( i ) SEQUENCE CHARACTERISTICS:
　　　　　　　　( A ) LENGTH: 72 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:35:

| AGGGAGGACG | ATGCGGGGCC | GAATAGGGAA | ATTTATTATT | ACTAACAGTA | 50 |
|---|---|---|---|---|---|
| ATCCCCAGA | CGACTCGCCC | GA | | | 72 |

( 2 ) INFORMATION FOR SEQ ID NO:36:

( i ) SEQUENCE CHARACTERISTICS:
　　　　　　　　( A ) LENGTH: 71 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:36:

| AGGGAGGACG | ATGCGGCAGG | ACTTAGGGAT | TTAGTTGTTT | TAGGGGTTAT | 50 |
|---|---|---|---|---|---|
| GTAGTCAGAC | GACTCGCCCG | A | | | 71 |

( 2 ) INFORMATION FOR SEQ ID NO:37:

( i ) SEQUENCE CHARACTERISTICS:
　　　　　　　　( A ) LENGTH: 72 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:37:

| AGGGAGGACG | ATGCGGGGGG | GGATGAGATG | TAATCCACAT | GTCACTTATT | 50 |
|---|---|---|---|---|---|
| AAGTCCCAGA | CGACTCGCCC | GA | | | 72 |

( 2 ) INFORMATION FOR SEQ ID NO:38:

( i ) SEQUENCE CHARACTERISTICS:
　　　　　　　　( A ) LENGTH: 72 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:38:

| AGGGAGGACG | ATGCGGCAGG | GGATGGGATG | TAATCCTCAT | GTCACTTATT | 50 |
|---|---|---|---|---|---|
| AAGTCCCAGA | CGACTCGCCC | GA | | | 72 |

( 2 ) INFORMATION FOR SEQ ID NO:39:

( i ) SEQUENCE CHARACTERISTICS:
　　　　　　　　( A ) LENGTH: 72 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:39:

| AGGGAGGACG | ATGCGGTACG | ACTACGATTG | AGTATCCGGC | TATAATATTA | 50 |
|---|---|---|---|---|---|
| CCATTGCAGA | CGACTCGCCC | GA | | | 72 |

( 2 ) INFORMATION FOR SEQ ID NO:40:

( i ) SEQUENCE CHARACTERISTICS:
　　　　　　　　( A ) LENGTH: 87 base pairs ( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:40:

GGGAGAUAAG AAUAAACGCU CAANNNNNNN NNNNNNNNNN NNNNNNNNNN        50

NNNNNNNNNN NNNUUCGACA GGAGGCUCAC AACAGGC        87

( 2 ) INFORMATION FOR SEQ ID NO:41:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:41:

TAATACGACT CACTATAGGG AGAUAAGAAU AAACGCUCAA        40

( 2 ) INFORMATION FOR SEQ ID NO:42:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:42:

GCCTGTTGTG AGCCTCCTGT CGAA        24

( 2 ) INFORMATION FOR SEQ ID NO:43:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:43:

GGGAGAUAAG AAUAAACGCU CAAAGGGCUC GUGUGCCAAA UCGCUAACAA        50

CAAGCUAGCU GAUUUCGACA GGAGGCUCAC AACAGGC        87

( 2 ) INFORMATION FOR SEQ ID NO:44:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:44:

GGGAGAUAAG AAUAAACGCU CAACUGGGCU CAUCCGGCGA AUGAUGCAAG        50

GAAGAUUUCA CAUUUCGACA GGAGGCUCAC AACAGGC        87

( 2 ) INFORMATION FOR SEQ ID NO:45:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:45:

GGGAGAUAAG AAUAAACGCU CAAAAGGAUA GUGUGCUCCU GUACCAAAUU        50

UCCAAAGCGA UAUUUCGACA GGAGGCUCAC AACAGGC        87

( 2 ) INFORMATION FOR SEQ ID NO:46:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:46:

GGGAGAUAAG AAUAAACGCU CAAAAGAGU AAAGCGCGGA ACAGGAUUCA        50

CGUUGCGCUC UUUUCGACAG GAGGCUCACA ACAGGC        86

( 2 ) INFORMATION FOR SEQ ID NO:47:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:47:

GGGAGAUAAG AAUAAACGCU CAAAAGAGU AAAGCGCGGA ACAGGAUUCA        50

CGUUGCGCUC AUUCGACAGG AGGCUCACAA CAGGC        85

( 2 ) INFORMATION FOR SEQ ID NO:48:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:

( D ) OTHER INFORMATION: All U's are 2'-F uracil ( x i ) SEQUENCE DESCRIPTION: SEQ ID NO:48:

GGGAGAUAAG AAUAAACGCU CAACAACGAU UAUCUUUUCG GCCGUGAAAC          50

CCAAACUGAC GCCUUCGACA GGAGGCUCAC AACAGGC          87

( 2 ) INFORMATION FOR SEQ ID NO:49:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:49:

GGGAGAUAAG AAUAAACGCU CAACGCGAGG AUAGGGUGCA GCUUCUGUUC          50

CAAAUACGUG AAUUUCGACA GGAGGCUCAC AACAGGC          87

( 2 ) INFORMATION FOR SEQ ID NO:50:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:50:

GGGAGAUAAG AAUAAACGCU CAAUAAGUCG AAGAGCUCCU GAUCCAAACC          50

AUCGAAAGGA CGUUUCGACA GGAGGCUCAC AACAGGC          87

( 2 ) INFORMATION FOR SEQ ID NO:51:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:51:

GGGAGAUAAG AAUAAACGCU CAAGGUAAGU UGGAGCUCCU UAUCCAAGCA          50

CGCAAUAAGU GACUUCGACA GGAGGCUCAC AACAGGC          87

( 2 ) INFORMATION FOR SEQ ID NO:52:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
       ( D ) OTHER INFORMATION: All C's are 2'-F cytosine ( i x ) FEATURE:
       ( D ) OTHER INFORMATION: All U's are 2'-F uracil ( x i ) SEQUENCE DESCRIPTION: SEQ ID NO:52:

| | | | | | |
|---|---|---|---|---|---|
| GGGAGAUAAG | AAUAAACGCU | CAAUUUGGCG | UGGGAUCCUG | GACUGAAGGA | 50 |
| UUUUGACGAU | GCUUCGACAG | GAGGCUCACA | ACAGGC | | 86 |

( 2 ) INFORMATION FOR SEQ ID NO:53:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
       ( D ) OTHER INFORMATION: All C's are 2'-F cytosine ( i x ) FEATURE:
       ( D ) OTHER INFORMATION: All U's are 2'-F uracil ( x i ) SEQUENCE DESCRIPTION: SEQ ID NO:53:

| | | | | | |
|---|---|---|---|---|---|
| GGGAGAUAAG | AAUAAACGCU | CAAAUUCAAG | ACAGAGACUU | UCCUUGAAUG | 50 |
| CUCUGUCCCA | UAAUUCGACA | GGAGGCUCAC | AACAGGC | | 87 |

( 2 ) INFORMATION FOR SEQ ID NO:54:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
       ( D ) OTHER INFORMATION: All C's are 2'-F cytosine ( i x ) FEATURE:
       ( D ) OTHER INFORMATION: All U's are 2'-F uracil ( x i ) SEQUENCE DESCRIPTION: SEQ ID NO:54:

| | | | | | |
|---|---|---|---|---|---|
| GGGAGAUAAG | AAUAAACGCU | CAAACAAAUG | UGCGACCUUG | GACGAAGUUA | 50 |
| ACUCGGACGG | UUCUUCGACA | GGAGGCUCAC | AACAGGC | | 87 |

( 2 ) INFORMATION FOR SEQ ID NO:55:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
       ( D ) OTHER INFORMATION: All C's are 2'-F cytosine ( i x ) FEATURE:
       ( D ) OTHER INFORMATION: All U's are 2'-F uracil ( x i ) SEQUENCE DESCRIPTION: SEQ ID NO:55:

| | | | | | |
|---|---|---|---|---|---|
| GGGAGAUAAG | AAUAAACGCU | CAAACAAAUG | UGCGCCCUUG | GACGAAGUUA | 50 |
| ACUCGGACGG | UUCUUCGACA | GGAGGCUCAC | AACAGGC | | 87 |

( 2 ) INFORMATION FOR SEQ ID NO:56:

( i ) SEQUENCE CHARACTERISTICS:
        ( A ) LENGTH: 87 base pairs ( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:56:

GGGAGAUAAG AAUAAACGCU CAAACAAAUG UGCGCCCUUG GACGAAGUUA         50

ACUCGGACGG UUGUUCGACA GGAGGCUCAC AACAGGC                      87

( 2 ) INFORMATION FOR SEQ ID NO:57:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:57:

GGGAGAUAAG AAUAAACGCU CAAACAAAUG UGCGCCCUUG GACGAAGUUA         50

ACUCGGACGG UUCUUCGACA GGAGGCUCAC AACAGGC                      87

( 2 ) INFORMATION FOR SEQ ID NO:58:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:58:

GGGAGAUAAG AAUAAACGCU CAAAGUCUG AGACUCCUGG ACUGAAUUAG          50

CUAGGACGGC UGUUCGACAG GAGGCUCACA ACAGGC                       86

( 2 ) INFORMATION FOR SEQ ID NO:59:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:59:

GGGAGAUAAG AAUAAACGCU CAAUAGGAGC CUAGCAGCCC CUGCAUCGAU         50

CACUAGGAUG GUUUUCGACA GGAGGCUCAC AACAGGC                      87

( 2 ) INFORMATION FOR SEQ ID NO:60:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:60:

```
GGGAGAUAAG  AAUAAACGCU  CAAAAGUGU  AGCCUUCCUG  GACUGUAGGU        50

ACUAGGACGG  UCCUUCGACA  GGAGGCUCAC  AACAGGC                      87
```

( 2 ) INFORMATION FOR SEQ ID NO:61:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:61:

```
GGGAGAUAAG  AAUAAACGCU  CAAACAAAUG  UGCUCCCUUG  GACGAAGUUA        50

ACUCGGCGGU  UCGACAGGAG  GCUCACAACA  GGC                           83
```

( 2 ) INFORMATION FOR SEQ ID NO:62:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:62:

```
GGGAGAUAAG  AAUAAACGCU  CAAAAGAAGC  UGGCGACAGG  CGAAAAGCAG        50

ACUUGAGGGG  AAUUCGACAG  GAGGCUCACA  ACAGGC                        86
```

( 2 ) INFORMATION FOR SEQ ID NO:63:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:63:

```
GGGAGAUAAG  AAUAAACGCU  CAAAGUAGGU  GAGGCUUCUG  GACUGAAGUA        50
```

ACUAGGUCGG UUCUUCGACA GGAGGCUCAC AACAGGC    87

( 2 ) INFORMATION FOR SEQ ID NO:64:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:64:

GGGAGAUAAG AAUAAACGCU CAACAUGAGC UGCUGGACCA AACAGAUGGA    50

GGAACCACCG UGUUUCGACA GGAGGCUCAC AACAGGC    87

( 2 ) INFORMATION FOR SEQ ID NO:65:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:65:

GGGAGAUAAG AAUAAACGCU CAAGAGCUCU UGACGAAAAC CUAUGCGAGA    50

UGGAUACUCG GUUUCGACA GGAGGCUCAC AACAGGC    87

( 2 ) INFORMATION FOR SEQ ID NO:66:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:66:

GGGAGAUAAG AAUAAACGCU CAAGAGCUCU UGACGAAAAC CUAUGCGAGA    50

AGGAUACUCG GUUUCGACA GGAGGCUCAC AACAGGC    87

( 2 ) INFORMATION FOR SEQ ID NO:67:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:67:

GGGAGAUAAG AAUAAACGCU CAAGAGCUCU AGACGAAAAC CUAUGCGAGA        50

UGAUACUCGG UCUUCGACAG GAGGCUCAAA CAGGC        85

( 2 ) INFORMATION FOR SEQ ID NO:68:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:68:

GGGAGAUAAG AAUAAACGCU CAAUGAGCUC UUGAAGAAGU CCGAACAUUC        50

UCCUUUCUGC GACUUUCGAC AGGAGGCUCA CAACAGGC        88

( 2 ) INFORMATION FOR SEQ ID NO:69:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:69:

GGGAGAUAAG AAUAAACGCU CAAGAGCUCC GGGAUCCAAG CGUGCAACAA        50

CACUAUGCCC ACUUCGACAG GAGGCUCACA ACAGGC        86

( 2 ) INFORMATION FOR SEQ ID NO:70:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:70:

GGGAGAUAAG AAUAAACGCU CAAAUACCC UCGGGAACCA AUCCGACCCU        50

AUUUUGCAGU UUGUUCGACA GGAGGCUCAC AACAGGC        87

( 2 ) INFORMATION FOR SEQ ID NO:71:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:

(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:71:

GGGAGAUAAG AAUAAACGCU CAAAUGAUGC UCCUGAAGUA AUCACCAGGA    50

CAUCCUCGGC AUUUCGACAG GAGGCUCACA ACAGGC    86

(2) INFORMATION FOR SEQ ID NO:72:

(i) SEQUENCE CHARACTERISTICS:
(A) LENGTH: 87 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:72:

GGGAGAUAAG AAUAAACGCU CAAGCAAUCU CGGACUAGAC CAACGACCUU    50

CGUUUGACGC UCAUUCGACA GGAGGCUCAC AACAGGC    87

(2) INFORMATION FOR SEQ ID NO:73:

(i) SEQUENCE CHARACTERISTICS:
(A) LENGTH: 87 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:73:

GGGAGAUAAG AAUAAACGCU CAACCGAUUU CUAGGACGGA UUUACGGAGA    50

AUUGAGUCGC AAGUUCGACA GGAGGCUCAC AACAGGC    87

(2) INFORMATION FOR SEQ ID NO:74:

(i) SEQUENCE CHARACTERISTICS:
(A) LENGTH: 87 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:74:

GGGAGAUAAG AAUAAACGCU CAAACGGCGA GAAUGACAAU GUUAUUCUAC    50

GAGCGAAGGA UUAUUCGACA GGAGGCUCAC AACAGGC    87

(2) INFORMATION FOR SEQ ID NO:75:

(i) SEQUENCE CHARACTERISTICS:
(A) LENGTH: 87 base pairs
(B) TYPE: nucleic acid (C) STRANDEDNESS: single
(D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:75:

```
GGGAGAUAAG AAUAAACGCU CAAGCAAUCU CGGACUAGAC UAACGACCUU    50
GGUUUGACGC UAAUUCGACA GGAGGCUCAC AACAGGC                  87
```

(2) INFORMATION FOR SEQ ID NO:76:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:76:

```
GGGAGAUAAG AAUAAACGCU CAAGCAAUCU CGGACUAGAC UAACGACCUU    50
CGUUUGACGC UCAUUCGACA GGAGGCUCAC AACAGGC                  87
```

(2) INFORMATION FOR SEQ ID NO:77:

(i) SEQUENCE CHARACTERISTICS:
    (A) LENGTH: 86 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:77:

```
GGGAGAUAAG AAUAAACGCU CAAAGAGCAG CCGGAGGUGU GAGCUCUGAC    50
UCUGAACAGC UGUUCGACAG GAGGCUCACA ACAGGC                   86
```

(2) INFORMATION FOR SEQ ID NO:78:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:78:

```
GGGAGAUAAG AAUAAACGCU CAACGGGAUU UCUCGGAAAA GACUAACGAC    50
UAAUUCCAGA ACCUUCGACA GGAGGCUCAC AACAGGC                  87
```

(2) INFORMATION FOR SEQ ID NO:79:

( i ) SEQUENCE CHARACTERISTICS:
  ( A ) LENGTH: 87 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C's are 2'-F cytosine ( i x ) FEATURE:
  ( D ) OTHER INFORMATION: All U's are 2'-F uracil ( x i ) SEQUENCE DESCRIPTION: SEQ ID NO:79:

```
GGGAGAUAAG AAUAAACGCU CAAGCAAUCU CGGACUAGGC UAACGACCUU        50
UGUUUGACGC UCAUUCGACA GGAGGCUCAC AACAGGC                      87
```

( 2 ) INFORMATION FOR SEQ ID NO:80:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:80:

```
GGGAGAUAAG AAUAAACGCU CAAGCAAUCU CGGACUAGAC UAACGACCUU        50
CGUUUGACGC UUAUUCGACA GGAGGCUCAC AACAGGC                      87
```

( 2 ) INFORMATION FOR SEQ ID NO:81:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:81:

```
GGGAGAUAAG AAUAAACGCU CAAUCCAAGG ACCAAACGGG UGUUCGGCAG        50
UGGACUUUAG CAAUUCGACA GGAGGCUCAC AACAGGC                      87
```

( 2 ) INFORMATION FOR SEQ ID NO:82:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:82:

```
GGGAGAUAAG AAUAAACGCU CAAUGGGCUA CAUGUGAGUA CACCAGCGUG        50
```

AGAGUUCUUA GGUUCGACAG GAGGCUCACA ACAGGC 86

(2) INFORMATION FOR SEQ ID NO:83:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:83:

GGGAGAUAAG AAUAAACGCU CAACUGUGCA GUAACUGCGG AUGAGACCAA 50

CCGGAUGGCU CAACUUCGAC AGGAGGCUCA CAACAGGC 88

(2) INFORMATION FOR SEQ ID NO:84:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:84:

GGGAGAUAAG AAUAAACGCU CAAACAAUCU CGGACUAGAC UAACGACCUU 50

CGUUUGACGC UUAUUCGACA GGAGGCUCAC AACAGGC 87

(2) INFORMATION FOR SEQ ID NO:85:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:85:

GGGAGAUAAG AAUAAACGCU CAAGCAAUCU CGGACGAGAC UAACGACCUU 50

CGUUUGACGC UUAUUCGACA GGAGGCUCAC AACAGGC 87

(2) INFORMATION FOR SEQ ID NO:86:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil ( x i ) SEQUENCE DESCRIPTION: SEQ ID NO:86:

GGGAGAUAAG AAUAAACGCU CAAAGCGCUA GAUGGACGAG AGACUUUUAA  50

GUAGCAAGCG GUAUUCGACA GGAGGCUCAC AACAGGC  87

( 2 ) INFORMATION FOR SEQ ID NO:87:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:87:

GGGAGAUAAG AAUAAACGCU CAACAGACUC AGAGCGCCGU GAGCUUCUGA  50

AGCAAUCGCA GGUUUCGACA GGAGGCUCAC AACAGGC  87

( 2 ) INFORMATION FOR SEQ ID NO:88:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:88:

GGGAGAUAAG AAUAAACGCU CAAGCGGGGA GCUCCUCGAG AAACUGAGUU  50

CAACUUCCCA GGUUUCGACA GGAGGCUCAC AACAGGC  87

( 2 ) INFORMATION FOR SEQ ID NO:89:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:89:

GGGAGAUAAG AAUAAACGCU CAAGUGUUGG AGCUCUUGAU UGGAAAAGUA  50

GAACAAAUCG AAAUUCGACA GGAGGCUCAC AACAGGC  87

( 2 ) INFORMATION FOR SEQ ID NO:90:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:90:

GGGAGAUAAG AAUAAACGCU CAAGUGUUGG AGCUCUUGAU UGGAAAAUUA  50

GAGCAAAUCG AAAUUCGACA GGAGGCUCAC AACAGGC  87

( 2 ) INFORMATION FOR SEQ ID NO:91:

( i ) SEQUENCE CHARACTERISTICS:
                ( A ) LENGTH: 87 base pairs
                ( B ) TYPE: nucleic acid
                ( C ) STRANDEDNESS: single
                ( D ) TOPOLOGY: linear ( i x ) FEATURE:
                ( D ) OTHER INFORMATION: All C's are 2'-F cytosine ( i x ) FEATURE:
                ( D ) OTHER INFORMATION: All U's are 2'-F uracil ( x i ) SEQUENCE DESCRIPTION: SEQ ID NO:91:

GGGAGAUAAG AAUAAACGCU CAACAAUCCG AGCUCUUGAA GCAAUCCUUG  50

AUUGCAAGAU GAUUUCGACA GGAGGCUCAC AACAGGC  87

( 2 ) INFORMATION FOR SEQ ID NO:92:

( i ) SEQUENCE CHARACTERISTICS:
                ( A ) LENGTH: 87 base pairs
                ( B ) TYPE: nucleic acid
                ( C ) STRANDEDNESS: single
                ( D ) TOPOLOGY: linear ( i x ) FEATURE:
                ( D ) OTHER INFORMATION: All C's are 2'-F cytosine ( i x ) FEATURE:
                ( D ) OTHER INFORMATION: All U's are 2'-F uracil ( x i ) SEQUENCE DESCRIPTION: SEQ ID NO:92:

GGGAGAUAAG AAUAAACGCU CAAUCGGAUG AGCUCUUGAA GCAGUUCAAG  50

GACAGACAUA AAGUUCGACA GGAGGCUCAC AACAGGC  87

( 2 ) INFORMATION FOR SEQ ID NO:93:

( i ) SEQUENCE CHARACTERISTICS:
                ( A ) LENGTH: 87 base pairs
                ( B ) TYPE: nucleic acid
                ( C ) STRANDEDNESS: single
                ( D ) TOPOLOGY: linear ( i x ) FEATURE:
                ( D ) OTHER INFORMATION: All C's are 2'-F cytosine ( i x ) FEATURE:
                ( D ) OTHER INFORMATION: All U's are 2'-F uracil ( x i ) SEQUENCE DESCRIPTION: SEQ ID NO:93:

GGGAGAUAAG AAUAAACGCU CAAUUCCAGG UUAGCGGCCA AACCUCGACU  50

UGAACAGACU UUAUUCGACA GGAGGCUCAC AACAGGC  87

( 2 ) INFORMATION FOR SEQ ID NO:94:

( i ) SEQUENCE CHARACTERISTICS:
                ( A ) LENGTH: 87 base pairs
                ( B ) TYPE: nucleic acid
                ( C ) STRANDEDNESS: single (D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:94:

GGGAGAUAAG AAUAAACGCU CAAGUGUUGG AGCUCUUGAU UGGAAAAGUA    50

GAGCAAAACG AAAUUCGACA GGAGGCUCAC AACAGGC    87

(2) INFORMATION FOR SEQ ID NO:95:

(i) SEQUENCE CHARACTERISTICS:
(A) LENGTH: 87 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:95:

GGGAGAUAAG AAUAAACGCU CAAGUGUUGG AGCUCUUGAU UGGAAAAGUA    50

GAGCAAAUCG AAAUUCGACA GGAGGCUCAC AACAGGC    87

(2) INFORMATION FOR SEQ ID NO:96:

(i) SEQUENCE CHARACTERISTICS:
(A) LENGTH: 87 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:96:

GGGAGAUAAG AAUAAACGCU CAAGUGGUGC UGCAAUUGCU CGGUCGGCGU    50

GCUCUCUACU UGAUUCGACA GGAGGCUCAC AACAGGC    87

(2) INFORMATION FOR SEQ ID NO:97:

(i) SEQUENCE CHARACTERISTICS:
(A) LENGTH: 87 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:97:

GGGAGAUAAG AAUAAACGCU CAAGCUCAAG AGACUGAAGG AAAAGCUUAG    50

AGCUCAAAGC AUAUUCGACA GGAGGCUCAC AACAGGC    87

(2) INFORMATION FOR SEQ ID NO:98:

( i ) SEQUENCE CHARACTERISTICS:
  ( A ) LENGTH: 87 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C's are 2'-F cytosine ( i x ) FEATURE:
  ( D ) OTHER INFORMATION: All U's are 2'-F uracil ( x i ) SEQUENCE DESCRIPTION: SEQ ID NO:98:

```
GGGAGAUAAG AAUAAACGCU CAACGUGUUG GGUUCAAAGA CCAGCUUACG        50
GUACACAGUA CGAUUCGACA GGAGGCUCAC AACAGGC                      87
```

( 2 ) INFORMATION FOR SEQ ID NO:99:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:99:

```
GGGAGAUAAG AAUAAACGCU CAAUCUGUUG GUUCAAAGAC UUGCUAAGGG        50
GUCGAAGCAC CCUUUCGACA GGAGGCUCAC AACAGGC                      87
```

( 2 ) INFORMATION FOR SEQ ID NO:100:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:100:

```
GGGAGAUAAG AAUAAACGCU CAAGACGACA AAGAGUCCGU UCCAAACCUC        50
UGAGACAGGG UUUCGACAGG AGGCUCACAA CAGGC                        85
```

( 2 ) INFORMATION FOR SEQ ID NO:101:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:101:

```
GGGAGAUAAG AAUAAACGCU CAAUAGCAAG UCCCACAUCC CAGACGGGCU        50
AAAAGAGGU GGAUUCGACA GGAGGCUCAC AACAGGC                       87
```

( 2 ) INFORMATION FOR SEQ ID NO:102:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:102:

```
GGGAGAUAAG AAUAAACGCU CAAAUGAACG ACCGCGGGCA GUCGCGUUCA        50
AAUGAGUGGU UUUUUCGACA GGAGGCUCAC AACAGGC                      87
```

( 2 ) INFORMATION FOR SEQ ID NO:103:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:103:

```
GGGAGAUAAG AAUAAACGCU CAAAUGAGUA GACCGAGGAA GCACCCGGCU        50
CUCAAAUGAG UGAUUCGACA GGAGGCUCAC AACAGGC                      87
```

( 2 ) INFORMATION FOR SEQ ID NO:104:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:104:

```
GGGAGAUAAG AAUAAACGCU CAAAUGAGUA GACCGAGGAA GCACCCGGCU        50
CUCAAAUGAC UGAUUCGACA GGAGGCUCAC AACAGGC                      87
```

( 2 ) INFORMATION FOR SEQ ID NO:105:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:105:

```
GGGAGAUAAG  AAUAAACGCU  CAAAAGGCCA  UCAGGGCAAA  GACCUCCUAG         50

GUACUGACGC  UUAUUCGACA  GGAGGCUCAC  AACAGGC                         87
```

( 2 ) INFORMATION FOR SEQ ID NO:106:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:106:

```
GGGAGAUAAG  AAUAAACGCU  CAAAAGGCCG  AACAACGAAG  UUUGAUUCAG         50

GUACUCAGCG  UUCUUCGACA  GGAGGCUCAC  AACAGGC                         87
```

( 2 ) INFORMATION FOR SEQ ID NO:107:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:107:

```
GGGAGAUAAG  AAUAAACGCU  CAAAAGGCCG  AACAACGAAG  AUUGAUUCAG         50

GUACUCAGCG  UUCUUCGACA  GGAGGCUCAC  AACAGGC                         87
```

( 2 ) INFORMATION FOR SEQ ID NO:108:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:108:

```
GGGAGAUAAG  AAUAAACGCU  CAAAAGGCGG  AGGGCAAGCA  AGAACCUCAC         50

GAACAGACGU  UAAUUCGACA  GGAGGCUCAC  AACAGGC                         87
```

( 2 ) INFORMATION FOR SEQ ID NO:109:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:109:

GGGAGAUAAG AAUAAACGCU CAAAGCCUGA GGUAUAGUUA CGCUAUAUGG    50

GAGGUAGGCU UUAUUCGACA GGAGGCUCAC AACAGGC    87

( 2 ) INFORMATION FOR SEQ ID NO:110:

( i ) SEQUENCE CHARACTERISTICS:
            ( A ) LENGTH: 87 base pairs
            ( B ) TYPE: nucleic acid
            ( C ) STRANDEDNESS: single
            ( D ) TOPOLOGY: linear ( i x ) FEATURE:
            ( D ) OTHER INFORMATION: All C's are 2'-F cytosine ( i x ) FEATURE:
            ( D ) OTHER INFORMATION: All U's are 2'-F uracil ( x i ) SEQUENCE DESCRIPTION: SEQ ID NO:110:

GGGAGAUAAG AAUAAACGCU CAACGUGAUG ACAGCUCGGA CGGCUCAUUG    50

CGCGGAGUAG CUAUUCGACA GGAGGCUCAC AACAGGC    87

( 2 ) INFORMATION FOR SEQ ID NO:111:

( i ) SEQUENCE CHARACTERISTICS:
            ( A ) LENGTH: 87 base pairs
            ( B ) TYPE: nucleic acid
            ( C ) STRANDEDNESS: single
            ( D ) TOPOLOGY: linear ( i x ) FEATURE:
            ( D ) OTHER INFORMATION: All C's are 2'-F cytosine ( i x ) FEATURE:
            ( D ) OTHER INFORMATION: All U's are 2'-F uracil ( x i ) SEQUENCE DESCRIPTION: SEQ ID NO:111:

GGGAGAUAAG AAUAAACGCU CAACGGCUCG AUGCUAGCUG GGACGGCUCA    50

UUGAGACUGG UUGUUCGACA GGAGGCUCAC AACAGGC    87

( 2 ) INFORMATION FOR SEQ ID NO:112:

( i ) SEQUENCE CHARACTERISTICS:
            ( A ) LENGTH: 87 base pairs
            ( B ) TYPE: nucleic acid
            ( C ) STRANDEDNESS: single
            ( D ) TOPOLOGY: linear ( i x ) FEATURE:
            ( D ) OTHER INFORMATION: All C's are 2'-F cytosine ( i x ) FEATURE:
            ( D ) OTHER INFORMATION: All U's are 2'-F uracil ( x i ) SEQUENCE DESCRIPTION: SEQ ID NO:112:

GGGAGAUAAG AAUAAACGCU CAAAGUGCAA CCUGAACCAA ACCAAACUAG    50

CGCGCAGUUG GGUUUCGACA GGAGGCUCAC AACAGGC    87

( 2 ) INFORMATION FOR SEQ ID NO:113:

( i ) SEQUENCE CHARACTERISTICS:
            ( A ) LENGTH: 87 base pairs
            ( B ) TYPE: nucleic acid
            ( C ) STRANDEDNESS: single
            ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:113:

GGGAGAUAAG AAUAAACGCU CAAAGCAGAU GGUGCUGAGG UAUCAUGAAG     50

ACGCUGACGC UUAUUCGACA GGAGGCUCAC AACAGGC     87

( 2 ) INFORMATION FOR SEQ ID NO:114:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:114:

GGGAGAUAAG AAUAAACGCU CAAGAAUGGA GCCAAGAAAG ACAGCGAUGU     50

CUCGGACGAU GAGUUCGACA GGAGGCUCAC AACAGGC     87

( 2 ) INFORMATION FOR SEQ ID NO:115:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:115:

GGGAGAUAAG AAUAAACGCU CAAGAAUGGA GCCAGGAAAG ACAGCGAUGU     50

CUCGGACGAU GAGUUCGACA GGAGGCUCAC AACAGGC     87

( 2 ) INFORMATION FOR SEQ ID NO:116:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:116:

GGGAGAUAAG AAUAAACGCU CAAGGAUGGA GCCAAGAAAG ACAGCGAUGU     50

CUCGGACGAU GAGUUCGACA GGAGGCUCAC AACAGGC     87

( 2 ) INFORMATION FOR SEQ ID NO:117:

( i ) SEQUENCE CHARACTERISTICS:

( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:117:

GGGAGAUAAG AAUAAACGCU CAACGUGAGA UUCCCUGCG UAAGACCAGA  50

AGACUAUCAG GCUUUCGACA GGAGGCUCAC AACAGGC  87

( 2 ) INFORMATION FOR SEQ ID NO:118:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:118:

GGGAGAUAAG AAUAAACGCU CAAAGGGUUG AGGCUUAUCC UUCUUUCGUU  50

CGUGACACGA UCGUUCGACA GGAGGCUCAC AACAGGC  87

( 2 ) INFORMATION FOR SEQ ID NO:119:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:119:

GGGAGAUAAG AAUAAACGCU CAAGAUUGAC ACGCACUCCA AUGGCUCUGA  50

AGUGUUCGUG UGCUUCGACA GGAGGCUCAC AACAGGC  87

( 2 ) INFORMATION FOR SEQ ID NO:120:

( i ) SEQUENCE CHARACTERISTICS:
( A ) LENGTH: 88 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:120:

GGGAGAUAAG AAUAAACGCU CAAAAAUUCA AUGCUCUGAU GGGUUUAUGA  50

GUUAAUGCGU GGACUUCGAC AGGAGGCUCA CAACAGGC  88

( 2 ) INFORMATION FOR SEQ ID NO:121:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:121:

```
GGGAGAUAAG AAUAAACGCU CAAAAAGGCC CUUUCAGCAG GGAUCGAGGU      50

ACUGGAUGGA UAUUCGACAG GAGGCUCACA ACAGGC                    86
```

( 2 ) INFORMATION FOR SEQ ID NO:122:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:122:

```
GGGAGAUAAG AAUAAACGCU CAAAAGUCG UGUGCGAGAG GCUCAGAUUU       50

AAUGCGGAGG AUUCGACAGG AGGCUCACAA CAGGC                     85
```

( 2 ) INFORMATION FOR SEQ ID NO:123:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:123:

```
GGGAGAUAAG AAUAAACGCU CAACGUUGAA AUCGCUCCUC AGUGUGAGUU      50

GAAUCAGCUG ACCUUCGACA GGAGGCUCAC AACAGGC                   87
```

( 2 ) INFORMATION FOR SEQ ID NO:124:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:124:

GGGAGAUAAG AAUAAACGCU CAAAGUUUGG AUUCGGCAGG UGCUGAGACU    50

UUGAUAGCCA CUAUUCGACA GGAGGCUCAC AACAGGC    87

( 2 ) INFORMATION FOR SEQ ID NO:125:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:125:

GGGAGAUAAG AAUAAACGCU CAAGUGAGAA AUGUCGGGG CGAUGACUUG    50

GACGGUCCAC CGUUCGACAG GAGGCUCACA ACAGGC    86

( 2 ) INFORMATION FOR SEQ ID NO:126:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:126:

GGGAGAUAAG AAUAAACGCU CAACGUUGAA AUCGCUCCUC AGCGUGAGUU    50

GAAUCAGCUG ACCUUCGACA GGAGGCUCAC AACAGGC    87

( 2 ) INFORMATION FOR SEQ ID NO:127:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:127:

GGGAGAUAAG AAUAAACGCU CAAAGAGAGG AACUGCGAUU CAGACCAAAA    50

CGGAAAUGGC UGUUUCGACA GGAGGCUCAC AACAGGC    87

( 2 ) INFORMATION FOR SEQ ID NO:128:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:

-continued ( D ) OTHER INFORMATION: All U's are 2'-F uracil ( x i ) SEQUENCE DESCRIPTION: SEQ ID NO:128:

| GGGAGAUAAG | AAUAAACGCU | CAAGAUAUAC | UAACUUUCUU | UGAAAGCCAA | 50 |
| AAGUAUUAAU | GCGUUCGACA | GGAGGCUCAC | AACAGGC | | 87 |

( 2 ) INFORMATION FOR SEQ ID NO:129:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:129:

| GGGAGAUAAG | AAUAAACGCU | CAAGAUAUAC | UAACUUUGUU | UGAAAGCCAA | 50 |
| AAGUAUUAAU | GCGUUCGACA | GGAGGCUCAC | AACAGGC | | 87 |

( 2 ) INFORMATION FOR SEQ ID NO:130:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:130:

| GGGAGAUAAG | AAUAAACGCU | CAAAGCCGAG | CUAAUCCCGA | AAGUGACCCG | 50 |
| GAACGACGCG | GCAUUCGACA | GGAGGCUCAC | AACAGGC | | 87 |

( 2 ) INFORMATION FOR SEQ ID NO:131:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:131:

| CGAAGUUAAC | UCGGACGGUU | CUUCG | 25 |

( 2 ) INFORMATION FOR SEQ ID NO:132:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
  ( D ) OTHER INFORMATION: All U's are 2'-F uracil ( x i ) SEQUENCE DESCRIPTION: SEQ ID NO:132:

CGAAGUUAAC UCGGACGGUU CUUCGACAG                              29

( 2 ) INFORMATION FOR SEQ ID NO:133:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:133:

UGGACGAAGU UAACUCGGAC GGUUCUUCG                              29

( 2 ) INFORMATION FOR SEQ ID NO:134:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:134:

CCCUUGGACG AAGUUAACUC GGACGGUUCU UCGACAGGAG G                41

( 2 ) INFORMATION FOR SEQ ID NO:135:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:135:

UCGAUCACUA GGAUGGUUUU CGA                                    23

( 2 ) INFORMATION FOR SEQ ID NO:136:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:136:

UCGAUCACUA GGAUGGUUUU CGACAGGAGG 30

( 2 ) INFORMATION FOR SEQ ID NO:137:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:137:

CCCCUGCAUC GAUCACUAGG AUGGUUUCG A 31

( 2 ) INFORMATION FOR SEQ ID NO:138:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:138:

CCCCUGCAUC GAUCACUAGG AUGGUUUCG ACAGGAGG 38

( 2 ) INFORMATION FOR SEQ ID NO:139:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:139:

GGGAGAUAAG AAUAAACGCU CAA 23

( 2 ) INFORMATION FOR SEQ ID NO:140:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:140:

UUCGACAGGA GGCUCACAAC AGGC 24

( 2 ) INFORMATION FOR SEQ ID NO:141:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:141:

```
GGGAGAUAAG  AAUAAACGCU  CAAACCACUG  GGCCCAGUUU  AGAAACUCAU      50

UGCCCAAAUC  CGGUUCGACA  GGAGGCUCAC  AACAGGC                     87
```

( 2 ) INFORMATION FOR SEQ ID NO:142:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:142:

```
GGGAGAUAAG  AAUAAACGCU  CAAAGAAGA  AUCGAAAAU  CUACCUUGUU       50

CGGAGCCUGC  UCUUUCGACA  GGAGGCUCAC  AACAGGC                     87
```

( 2 ) INFORMATION FOR SEQ ID NO:143:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:143:

```
GGGAGAUAAG  AAUAAACGCU  CAAUCUAGAC  AGCGAAGGCU  GAGCUAUGAC      50

ACUGAACUUC  UUAUUCGACA  GGAGGCUCAC  AACAGGC                     87
```

( 2 ) INFORMATION FOR SEQ ID NO:144:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:144:

```
GGGAGAUAAG  AAUAAACGCU  CAAGCAAUCU  GGACUAGACU  AACGACCUUC       50

GCUUGACGCU  CAUUCGACAG  GAGGCUCACA  ACAGGC                       86
```

( 2 ) INFORMATION FOR SEQ ID NO:145:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:145:

```
GGGAGAUAAG  AAUAAACGCU  CAAGCAAUCU  CGGACUAGAC  UAACGACCUU       50

CGUUUGACGC  AAUUUCGACA  GGAGGCUCAC  AACAGGC                      87
```

( 2 ) INFORMATION FOR SEQ ID NO:146:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:146:

```
GGGAGAUAAG  AAUAAACGCU  CAAGCAAUCU  CGGACUAGAC  UAACGACCUU       50

CGUUUGACGC  UCAUUCGACA  GGAGGCUCAC  AACAGGC                      87
```

( 2 ) INFORMATION FOR SEQ ID NO:147:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:147:

```
GGGAGAUAAG  AAUAAACGCU  CAAGCAAUCU  CGGACUCGAC  UAACGACCUU       50

CGUUUGACGC  UCAUUCGACA  GGAGGCUCAC  AACAGGC                      87
```

( 2 ) INFORMATION FOR SEQ ID NO:148:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:

(D) OTHER INFORMATION: All U's are 2'-F uracil (x i) SEQUENCE DESCRIPTION: SEQ ID NO:148:

GGGAGAUAAG AAUAAACGCU CAAGACAAUA ACCGCACCAA CGUUCUGUUC         50

UUCGCUUGCA CGUUUCGACA GGAGGCUCAC AACAGGC         87

(2) INFORMATION FOR SEQ ID NO:149:

(i) SEQUENCE CHARACTERISTICS:
      (A) LENGTH: 87 base pairs
      (B) TYPE: nucleic acid
      (C) STRANDEDNESS: single
      (D) TOPOLOGY: linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:149:

GGGAGAUAAG AAUAAACGCU CAACAAUUCC CACUGAUUCG GGGCGGUCCU         50

UGCGAUGGCG AGAUUCGACA GGAGGCUCAC AACAGGC         87

(2) INFORMATION FOR SEQ ID NO:150:

(i) SEQUENCE CHARACTERISTICS:
      (A) LENGTH: 87 base pairs
      (B) TYPE: nucleic acid
      (C) STRANDEDNESS: single
      (D) TOPOLOGY: linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:150:

GGGAGAUAAG AAUAAACGCU CAACUCAGAC AACCAACAGC ACGUUCUCUG         50

UUUUCGUCGU UUGUUCGACA GGAGGCUCAC AACAGGC         87

(2) INFORMATION FOR SEQ ID NO:151:

(i) SEQUENCE CHARACTERISTICS:
      (A) LENGTH: 87 base pairs
      (B) TYPE: nucleic acid
      (C) STRANDEDNESS: single
      (D) TOPOLOGY: linear (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:151:

GGGAGAUAAG AAUAAACGCU CAAGCAAUCU CGGACUAGAC UAACGACCUU         50

CGUUUGACGC UUAUUCGACA GGAGGCUCAC AACAGGC         87

(2) INFORMATION FOR SEQ ID NO:152:

(i) SEQUENCE CHARACTERISTICS:
      (A) LENGTH: 87 base pairs
      (B) TYPE: nucleic acid
      (C) STRANDEDNESS: single
      (D) TOPOLOGY: linear ( i x ) FEATURE:
  ( D ) OTHER INFORMATION: All C's are 2'-F cytosine ( i x ) FEATURE:
  ( D ) OTHER INFORMATION: All U's are 2'-F uracil ( x i ) SEQUENCE DESCRIPTION: SEQ ID NO:152:

GGGAGAUAAG AAUAAACGCU CAAGCAAUCU CGGACUAGAC UAACGACCUU    50

CGUUUGACGC UCGUUCGACA GGAGGCUCAC AACAGGC    87

( 2 ) INFORMATION FOR SEQ ID NO:153:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:153:

GGGAGAUAAG AAUAAACGCU CAACGCUCAU GACCAGGCGC UACUGACUGA    50

GAUGUUGAAC UUAUUCGACA GGAGGCUCAC AACAGGC    87

( 2 ) INFORMATION FOR SEQ ID NO:154:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:154:

GGGAGAUAAG AAUAAACGCU CAAGCAAUCU CGGACUAGAC UAACGACCCU    50

CGUUUGACGC UCAUUCGACA GGAGGCUCAC AACAGGC    87

( 2 ) INFORMATION FOR SEQ ID NO:155:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:155:

GGGAGAUAAG AAUAAACGCU CAAAUAAGAU CAACAUUGGC GGUUUAUGUU    50

AUUCGUCCGU UUGUUCGACA GGAGGCUCAC AACAGGC    87

( 2 ) INFORMATION FOR SEQ ID NO:156:

( i ) SEQUENCE CHARACTERISTICS:
    ( A ) LENGTH: 87 base pairs (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:156:

GGGAGAUAAG AAUAAACGCU CAAGCAAUCU CGGACUAGAC UAACGACCUU     50

CGUUUGACGC UUAUUCGACA GGAGGCUCAC AACAGGC     87

(2) INFORMATION FOR SEQ ID NO:157:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:157:

GGGAGAUAAG AAUAAACGCU CAACACGCGA GAGCUUCUAA AGCUGCUGAA     50

UCGAGCUCCA CGAUUCGACA GGAGGCUCAC AACAGGC     87

(2) INFORMATION FOR SEQ ID NO:158:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:158:

GGGAGAUAAG AAUAAACGCU CAAACAAUCU CGGACUAGAC UAACGACCUU     50

CGUUUGACGC UUAUUCGACA GGAGGCUCAC AACAGGC     87

(2) INFORMATION FOR SEQ ID NO:159:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:159:

GGGAGAUAAG AAUAAACGCU CAAGCAAUCU CGGAUUAGAC UAACGACCUU     50

UGUUUGACGC UCAUUCGACA GGAGGCUCAC AACAGGC     87

( 2 ) INFORMATION FOR SEQ ID NO:160:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:160:

```
GGGAGAUAAG AAUAAACGCU CAAGCAAUCU CGGACUAGAC UAACGACCUU        50
CGUAUGACGC UUAUUCGACA GGAGGCUCAC AACAGGC                     87
```

( 2 ) INFORMATION FOR SEQ ID NO:161:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:161:

```
GGGAGAUAAG AAUAAACGCU CAAGCAAUCU CGGACUAGAC UAACGACCUU        50
CGCUUGACGC UCAUUCGACA GGAGGCUCAC AACAGGC                     87
```

( 2 ) INFORMATION FOR SEQ ID NO:162:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:162:

```
GGGAGAUAAG AAUAAACGCU CAAGGAGAUC CUCGAGGAAA CUCGAACUUC        50
UUCCCGACGU UGAUUCGACA GGAGGCUCAC AACAGGC                     87
```

( 2 ) INFORMATION FOR SEQ ID NO:163:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:163:

```
GGGAGAUAAG AAUAAACGCU CAAACAGCUC GGAUAAGACU AACGACCAG        50
```

UUUGGCUAAG CAAUUCGACA GGAGGCUCAC AACAGGC    87

( 2 ) INFORMATION FOR SEQ ID NO:164:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:164:

GGGAGAUAAG AAUAAACGCU CAAGCAAUCU CGGACUAGAC UAACGACCUU    50

CGUUUGACGC UCAUUCGACA GGAGGCUCAC AACAGGC    87

( 2 ) INFORMATION FOR SEQ ID NO:165:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:165:

GGGAGAUAAG AAUAAACGCU CAAACAAGGG AGUCGGUUUA UUCAGCCUGU    50

UCGGAACCUG ACUUCGACA GGAGGCUCAC AACAGGC    87

( 2 ) INFORMATION FOR SEQ ID NO:166:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:166:

GGGAGAUAAG AAUAAACGCU CAAAUCCAAG ACGCUUAGUU CUUGCUCUUC    50

GGGGCUUCCU ACGUUCGACA GGAGGCUCAC AACAGGC    87

( 2 ) INFORMATION FOR SEQ ID NO:167:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:167:

GGGAGAUAAG AAUAAACGCU CAAAAGUAAA CUCGAGACCG UUCUGGCUGA    50

UUCGGGGCAC UCUUUCGACA GGAGGCUCAC AACAGGC    87

( 2 ) INFORMATION FOR SEQ ID NO:168:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:168:

GGGAGAUAAG AAUAAACGCU CAAACUUGAC AAUCCCCUG AUUCGGGCC    50

UGACUAUCAC GAUUCGACAG GAGGCUCACA ACAGGC    86

( 2 ) INFORMATION FOR SEQ ID NO:169:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:169:

GGGAGAUAAG AAUAAACGCU CAAACACGAC AUCGAAGUUA UCCCCCUGAU    50

UCGGAGCCAG CUGUUCGACA GGAGGCUCAC AACAGGC    87

( 2 ) INFORMATION FOR SEQ ID NO:170:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:170:

GGGAGAUAAG AAUAAACGCU CAAAGCUGGA AAUCCAAAUG CUUUGUCUAG    50

UUGGGGCCAC UUUUCGACAG GAGGCUCACA ACAGGC    86

( 2 ) INFORMATION FOR SEQ ID NO:171:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:

( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:171:

GGGAGAUAAG AAUAAACGCU CAAAGACUCU UGAUCAUCCC CCUAGUUCGG     50

GGCUGACUGC ACUUUCGACA GGAGGCUCAC AACAGGC     87

( 2 ) INFORMATION FOR SEQ ID NO:172:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:172:

GGGAGAUAAG AAUAAACGCU CAAACUUGAC AAUCCCCUG AUUCGGGCC     50

UGACUAUCAC GAUUUCGACA GGAGGCUCAC AACAGGC     87

( 2 ) INFORMATION FOR SEQ ID NO:173:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:173:

GGGAGAUAAG AAUAAACGCU CAAGGAGCGA AAUUCUUGAA UAUCCACUGA     50

UUCGGACCGU CCUUUCGACA GGAGGCUCAC AACAGGC     87

( 2 ) INFORMATION FOR SEQ ID NO:174:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:174:

GGGAGAUAAG AAUAAACGCU CAAGCGGGAU UUUCCUGAUC AUCCCACUGA     50

UUCGGGGCCU UAGUUCGACA GGAGGCUCAC AACAGGC     87

( 2 ) INFORMATION FOR SEQ ID NO:175:

( i ) SEQUENCE CHARACTERISTICS:
        ( A ) LENGTH: 87 base pairs
        ( B ) TYPE: nucleic acid (C) STRANDEDNESS: single
            (D) TOPOLOGY: linear (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:175:

GGGAGAUAAG AAUAAACGCU CAAAGUUUCU CCUUGGCAAU CCCCCUAUU        50

CGGGGCUUCA UUGUUCGACA GGAGGCUCAC AACAGGC        87

(2) INFORMATION FOR SEQ ID NO:176:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:176:

GGGAGAUAAG AAUAAACGCU CAAGAGCGAA AUUCUUGAAU AUCCACUGAU        50

UCGGAGCGUC CUUUCGACAG GAGGCUCACA ACAGGC        86

(2) INFORMATION FOR SEQ ID NO:177:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:177:

GGGAGAUAAG AAUAAACGCU CAAACGGCAU UCUAAACAUU CCCCCUUGUU        50

CGGAGCCACU CUUUCGACAG GAGGCUCACA ACAGGC        86

(2) INFORMATION FOR SEQ ID NO:178:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:178:

GGGAGAUAAG AAUAAACGCU CAAGCGGAUU UUGAUCAUCC CCCUGAUUCG        50

GAGACCUCUU ACUUCGACAG GAGGCUCACA ACAGGC        86

(2) INFORMATION FOR SEQ ID NO:179:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:179:

GGGAGAUAAG AAUAAACGCU CAAGGGAACG AAUCGUCCAA AGACCUCGC    50

GGAAUCGGCG UUAUUCGACA GGAGGCUCAC AACAGGC    87

(2) INFORMATION FOR SEQ ID NO:180:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:180:

GGGAGAUAAG AAUAAACGCU CAAGCGAGCU CUUGCACAAA ACCGAUCCUC    50

GCAUACAGCA GGUUUCGACA GGAGGCUCAC AACAGGC    87

(2) INFORMATION FOR SEQ ID NO:181:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:181:

GGGAGAUAAG AAUAAACGCU CAAGGGAACG AAUCGUUCAA AAGACCACGC    50

GAAUCGGCGC UUAUUCGACA GGAGGCUCAC AACAGGC    87

(2) INFORMATION FOR SEQ ID NO:182:

(i) SEQUENCE CHARACTERISTICS:
    (A) LENGTH: 87 base pairs
    (B) TYPE: nucleic acid
    (C) STRANDEDNESS: single
    (D) TOPOLOGY: linear (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:182:

GGGAGAUAAG AAUAAACGCU CAAGAGCUGU UGACGAAAAC UUAUGCGGAG    50

AUGGAUACUC GGUUUCGACA GGAGGCUCAC AACAGGC 87

( 2 ) INFORMATION FOR SEQ ID NO:183:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:183:

GGGAGAUAAG AAUAAACGCU CAAGAGCUCU UGACGAAAAC CUAUUCGAGA 50

UGGAUACUCG GUUUUCGACA GGAGGCUCAC AACAGGC 87

( 2 ) INFORMATION FOR SEQ ID NO:184:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:184:

GGGAGAUAAG AAUAAACGCU CAAGGAGCCG AUUGUACAAC CUAGGUGAGC 50

UCAAUCACCU CGCUUCGACA GGAGGCUCAC AACAGGC 87

( 2 ) INFORMATION FOR SEQ ID NO:185:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:185:

GGGAGAUAAG AAUAAACGCU CAAGGGCCCU CUGCUACAAC UUCGGCAAGG 50

ACAUUUUCCG GACUUCGACA GGAGGCUCAC AACAGGC 87

( 2 ) INFORMATION FOR SEQ ID NO:186:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:186:

GGGAGAUAAG AAUAAACGCU CAAGAGCUCU UGACGAAAAC CUAUGCGAGA    50

UGGAUACUCG GUUUUCGACA GGAGGCUCAC AACAGGC    87

( 2 ) INFORMATION FOR SEQ ID NO:187:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:187:

GGGAGAUAAG AAUAAACGCU CAAGAAAGCC AUGUUGAAAG UUUCACCCAG    50

AUUCGGAGUC GUUGUUCGAC AGGAGGCUCA CAACAGGC    88

( 2 ) INFORMATION FOR SEQ ID NO:188:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:188:

GGGAGAUAAG AAUAAACGCU CAAACUGAGC UCGUGUACAA UGUUAGGGAA    50

GGACAUCUCG AUAUUCGACA GGAGGCUCAC AACAGGC    87

( 2 ) INFORMATION FOR SEQ ID NO:189:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:189:

GGGAGAUAAG AAUAAACGCU CAAGAGCUCU UGACGAAAAC CUAUGCGAGA    50

AGGAUACUCG GUUUUCGACA GGAGGCUCAC AACAGGC    87

( 2 ) INFORMATION FOR SEQ ID NO:190:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:190:

GGGAGAUAAG AAUAAACGCU CAAGAGCUCU UGACGAAAAC CUACGCGAGA      50

UGGAAACUCG GUUUUCGACA GGAGGCUCAC AACAGGC      87

( 2 ) INFORMATION FOR SEQ ID NO:191:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:191:

GGGAGAUAAG AAUAAACGCU CAACACAGGG GUUUCAAACC UCCCCCUGAU      50

UCGGAGCUUC UUCGACAGGA GGCUCACAAC AGGC      84

( 2 ) INFORMATION FOR SEQ ID NO:192:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:192:

GGGAGAUAAG AAUAAACGCU CAAAACCUCG CCAGGAAUAA CUUGCGACUU      50

UCGGAUCGUC UUAUUCGACA GGAGGCUCAC AACAGGC      87

( 2 ) INFORMATION FOR SEQ ID NO:193:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:193:

GGGAGAUAAG AAUAAACGCU CAAGAGCUCU UGACGAAAAC CUAUGCGAGA      50

UGGAUACUCG GUUUUCGACA GGAGGCUCAC AACAGGC      87

( 2 ) INFORMATION FOR SEQ ID NO:194:

( i ) SEQUENCE CHARACTERISTICS:
        ( A ) LENGTH: 87 base pairs
        ( B ) TYPE: nucleic acid
        ( C ) STRANDEDNESS: single

```
              ( D ) TOPOLOGY: linear ( i x ) FEATURE:
              ( D ) OTHER INFORMATION: All C's are 2'-F cytosine ( i x ) FEATURE:
              ( D ) OTHER INFORMATION: All U's are 2'-F uracil ( x i ) SEQUENCE DESCRIPTION: SEQ ID NO:194:

GGGAGAUAAG  AAUAAACGCU  CAACUUUGGA  GCUCCUGGAA  CGAAAGCGGA           50

AUUAACUUCC  UUAUUCGACA  GGAGGCUCAC  AACAGGC                          87

( 2 ) INFORMATION FOR SEQ ID NO:195:

( i ) SEQUENCE CHARACTERISTICS:
              ( A ) LENGTH: 87 base pairs
              ( B ) TYPE: nucleic acid
              ( C ) STRANDEDNESS: single
              ( D ) TOPOLOGY: linear ( i x ) FEATURE:
              ( D ) OTHER INFORMATION: All C's are 2'-F cytosine ( i x ) FEATURE:
              ( D ) OTHER INFORMATION: All U's are 2'-F uracil ( x i ) SEQUENCE DESCRIPTION: SEQ ID NO:195:

GGGAGAUAAG  AAUAAACGCU  CAAACAAUUC  AGGACGGGGU  UUCUUGAAUG           50

GGUUCGACCU  UCAUUCGACA  GGAGGCUCAC  AACAGGC                          87

( 2 ) INFORMATION FOR SEQ ID NO:196:

( i ) SEQUENCE CHARACTERISTICS:
              ( A ) LENGTH: 86 base pairs
              ( B ) TYPE: nucleic acid
              ( C ) STRANDEDNESS: single
              ( D ) TOPOLOGY: linear ( i x ) FEATURE:
              ( D ) OTHER INFORMATION: All C's are 2'-F cytosine ( i x ) FEATURE:
              ( D ) OTHER INFORMATION: All U's are 2'-F uracil ( x i ) SEQUENCE DESCRIPTION: SEQ ID NO:196:

GGGAGAUAAG  AAUAAACGCU  CAACCAGUAG  AUCAACUCCC  UGGCAACUGG           50

UUCGCCGUUA  UAUUCGACAG  GAGGCUCACA  ACAGGC                           86

( 2 ) INFORMATION FOR SEQ ID NO:197:

( i ) SEQUENCE CHARACTERISTICS:
              ( A ) LENGTH: 86 base pairs
              ( B ) TYPE: nucleic acid
              ( C ) STRANDEDNESS: single
              ( D ) TOPOLOGY: linear ( i x ) FEATURE:
              ( D ) OTHER INFORMATION: All C's are 2'-F cytosine ( i x ) FEATURE:
              ( D ) OTHER INFORMATION: All U's are 2'-F uracil ( x i ) SEQUENCE DESCRIPTION: SEQ ID NO:197:

GGGAGAUAAG  AAUAAACGCU  CAAACCUUGA  UGUUCACUCC  CUAACUCAAG           50

GUUCGACGUC  UAUUCGACAG  GAGGCUCACA  ACAGGC                           86

( 2 ) INFORMATION FOR SEQ ID NO:198:
```

( i ) SEQUENCE CHARACTERISTICS:
 ( A ) LENGTH: 87 base pairs
 ( B ) TYPE: nucleic acid
 ( C ) STRANDEDNESS: single
 ( D ) TOPOLOGY: linear ( i x ) FEATURE:
 ( D ) OTHER INFORMATION: All C's are 2'-F cytosine ( i x ) FEATURE:
 ( D ) OTHER INFORMATION: All U's are 2'-F uracil ( x i ) SEQUENCE DESCRIPTION: SEQ ID NO:198:

```
GGGAGAUAAG AAUAAACGCU CAAACAACCU GGACAAGGAA UUUUUCUAGU        50
GUUCGUUGGA CGUUUCGACA GGAGGCUCAC AACAGGC                      87
```

( 2 ) INFORMATION FOR SEQ ID NO:199:

( i ) SEQUENCE CHARACTERISTICS:
 ( A ) LENGTH: 87 base pairs
 ( B ) TYPE: nucleic acid
 ( C ) STRANDEDNESS: single
 ( D ) TOPOLOGY: linear ( i x ) FEATURE:
 ( D ) OTHER INFORMATION: All C's are 2'-F cytosine ( i x ) FEATURE:
 ( D ) OTHER INFORMATION: All U's are 2'-F uracil ( x i ) SEQUENCE DESCRIPTION: SEQ ID NO:199:

```
GGGAGAUAAG AAUAAACGCU CAAACCUUGA UGUUGAACUC CCUAACUCAA        50
GGCUCGACGU CUAUUCGACA GGAGGCUCAC AACAGGC                      87
```

( 2 ) INFORMATION FOR SEQ ID NO:200:

( i ) SEQUENCE CHARACTERISTICS:
 ( A ) LENGTH: 87 base pairs
 ( B ) TYPE: nucleic acid
 ( C ) STRANDEDNESS: single
 ( D ) TOPOLOGY: linear ( i x ) FEATURE:
 ( D ) OTHER INFORMATION: All C's are 2'-F cytosine ( i x ) FEATURE:
 ( D ) OTHER INFORMATION: All U's are 2'-F uracil ( x i ) SEQUENCE DESCRIPTION: SEQ ID NO:200:

```
GGGAGAUAAG AAUAAACGCU CAAACGAAGG CAACUUCAAA CAUUUCCUUA        50
CGUUCCGCGC UCAUUCGACA GGAGGCUCAC AACAGGC                      87
```

( 2 ) INFORMATION FOR SEQ ID NO:201:

( i ) SEQUENCE CHARACTERISTICS:
 ( A ) LENGTH: 87 base pairs
 ( B ) TYPE: nucleic acid
 ( C ) STRANDEDNESS: single
 ( D ) TOPOLOGY: linear ( i x ) FEATURE:
 ( D ) OTHER INFORMATION: All C's are 2'-F cytosine ( i x ) FEATURE:
 ( D ) OTHER INFORMATION: All U's are 2'-F uracil ( x i ) SEQUENCE DESCRIPTION: SEQ ID NO:201:

```
GGGAGAUAAG AAUAAACGCU CAAACGGCGC CAACAGCGAA UGUUCGCCCC        50
GUUCGGACGC UUAUUCGACA GGAGGCUCAC AACAGGC                      87
```

( 2 ) INFORMATION FOR SEQ ID NO:202:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:202:

```
GGGAGAUAAG AAUAAACGCU CAAACCGACA CAACCACGAC GUUCGGUCGG      50
UUUGUCCGAU UAUUCGACAG GAGGCUCACA ACAGGC                    86
```

( 2 ) INFORMATION FOR SEQ ID NO:203:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:203:

```
GGGAGAUAAG AAUAAACGCU CAAACGGAGG CAACCAAGAG AUUUCCAUCG      50
UUCGUUCGAU UGAUUCGACA GGAGGCUCAC AACAGGC                   87
```

( 2 ) INFORMATION FOR SEQ ID NO:204:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:204:

```
GGGAGAUAAG AAUAAACGCU CAAUCCAUCC AACGCGGCAA GAUUUGAUGG      50
ACUUUGACGA UCAUUCGACA GGAGGCUCAC AACAGGC                   87
```

( 2 ) INFORMATION FOR SEQ ID NO:205:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:205:

```
GGGAGAUAAG  AAUAAACGCU  CAAAAGCUCA  GCAGAUCGGG  ACUUCUGAUC        50

UUCGGGUCGC  UUAUUCGACA  GGAGGCUCAC  AACAGGC                       87
```

( 2 ) INFORMATION FOR SEQ ID NO:206:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:206:

```
GGGAGAUAAG  AAUAAACGCU  CAACAACGGU  AGCGGCUAGA  ACGCGCCGAC        50

UGAUUUAGGC  UUAUUCGACA  GGAGGCUCAC  AACAGGC                       87
```

( 2 ) INFORMATION FOR SEQ ID NO:207:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:207:

```
GGGAGAUAAG  AAUAAACGCU  CAAUCCUCCU  GUUCGGAGUC  UCAAUGUCGA        50

CUCGGCCGGA  CCUUUCGACA  GGAGGCUCAC  AACAGGC                       87
```

( 2 ) INFORMATION FOR SEQ ID NO:208:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:208:

```
GGGAGAUAAG  AAUAAACGCU  CAAAGAAAUC  CCCUUGAUUC  GGAGUCGUCU        50

UUUCGAGCGU  AGUUUCGACA  GGAGGCUCAC  AACAGGC                       87
```

( 2 ) INFORMATION FOR SEQ ID NO:209:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:209:

GGGAGAUAAG AAUAAACGCU CAAAGAAAUC CCCUUGAUUC GGAGUCGUCU     50

UUUCGAGCGA AGGUUCGACA GGAGGCUCAC AACAGGC     87

( 2 ) INFORMATION FOR SEQ ID NO:210:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:210:

GGGAGAUAAG AAUAAACGCU CAAGAGAGUC AACUGCGAGA AUGGCUUUCC     50

CAACGGCACC UUUUUCGACA GGAGGCUCAC AACAGGC     87

( 2 ) INFORMATION FOR SEQ ID NO:211:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:211:

GGGAGAUAAG AAUAAACGCU CAAAGAUAAU CCCCCGGAUU CGGAGUCCUC     50

UUGACGAACU UCCUUCGACA GGAGGCUCAC AACAGGC     87

( 2 ) INFORMATION FOR SEQ ID NO:212:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:212:

GGGAGAUAAG AAUAAACGCU CAACGGAACA AACGGAAAUG GCACACAGGA     50

GAAAGACGAG ACCUUCGACA GGAGGCUCAC AACAGGC     87

( 2 ) INFORMATION FOR SEQ ID NO:213:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
       ( D ) OTHER INFORMATION: All C's are 2'-F cytosine ( i x ) FEATURE:
       ( D ) OTHER INFORMATION: All U's are 2'-F uracil ( x i ) SEQUENCE DESCRIPTION: SEQ ID NO:213:

```
GGGAGAUAAG  AAUAAACGCU  CAACAGGAGA  UUAAGGAACA  GGCCACAGAU        50
AGAGACACGG  AGCUUCGACA  GGAGGCUCAC  AACAGGC                        87
```

( 2 ) INFORMATION FOR SEQ ID NO:214:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:214:

```
GGGAGAUAAG  AAUAAACGCU  CAAAACUGGA  CGAGAGGAGC  UAGCGUCCAA        50
GUUCGGAGCU  AUUCGACAGG  AGGCUCACAA  CAGGC                          85
```

( 2 ) INFORMATION FOR SEQ ID NO:215:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:215:

```
GGGAGAUAAG  AAUAAACGCU  CAAACUGAUU  CUCAGCGGCU  AGCGCUGAAG        50
UUCGACUAGU  UCAUUCGACA  GGAGGCUCAC  AACAGGC                        87
```

( 2 ) INFORMATION FOR SEQ ID NO:216:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:216:

```
GGGAGAUAAG  AAUAAACGCU  CAAGGCCACA  AGCAGAGAAC  AGAACAACAG        50
AGCGAUGGAG  AGAUUCGACA  GGAGGCUCAC  AACAGGC                        87
```

( 2 ) INFORMATION FOR SEQ ID NO:217:

( i ) SEQUENCE CHARACTERISTICS:

( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:217:

GGGAGAUAAG AAUAAACGCU CAAGGAGCAU CCAGGAUAAC AGGCUAAACA          50

CCGCAAGGAC CAGUUCGACA GGAGGCUCAC AACAGGC                        87

( 2 ) INFORMATION FOR SEQ ID NO:218:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:218:

GGGAGAUAAG AAUAAACGCU CAACGGAGGA AGGAAGAGGA ACCUUCGCCU          50

CUGAUUUAGC UUAUUCGACA GGAGGCUCAC AACAGGC                        87

( 2 ) INFORMATION FOR SEQ ID NO:219:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:219:

GGGAGAUAAG AAUAAACGCU CAACGUGGGC AAACUGAGGC AUUCCCGCG          50

CUCAGAGAUU CAUUCGACA GGAGGCUCAC AACAGGC                        87

( 2 ) INFORMATION FOR SEQ ID NO:220:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:220:

GGGAGAUAAG AAUAAACGCU CAACAAUGGC AACUAGGCCA CAAAGUUCCC          50

ACUGAUUCGA CGUUUCGACA GGAGGCUCAC AACAGGC                        87

( 2 ) INFORMATION FOR SEQ ID NO:221:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:221:

```
GGGAGAUAAG AAUAAACGCU CAAGCAAUCG GACCGAAAGG CCUUACCGAU        50

UUCUCGACCU UUCUUCGACA GGAGGCUCAC AACAGGC                      87
```

( 2 ) INFORMATION FOR SEQ ID NO:222:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:222:

```
GGGAGAUAAG AAUAAACGCU CAACGGAGGA AGGAAGAGGA ACCUUUGCCU        50

CUGAUUUAGC UUAUUCGACA GGAGGCUCAC AACAGGC                      87
```

( 2 ) INFORMATION FOR SEQ ID NO:223:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:223:

```
GGGAGAUAAG AAUAAACGCU CAACGGAGGA AGGAAGAGGA ACCUUCGCCU        50

CUGAUUUAGC UUAUUCGACA GGAGGCUCAC AACAGGC                      87
```

( 2 ) INFORMATION FOR SEQ ID NO:224:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:224:

```
GGGAGAUAAG  AAUAAACGCU  CAAAGUCGAG  UUUCAAGGAU  CAUCCCCUC      50

UUCGGAGCCU  UUCUUCGACA  GGAGGCUCAC  AACAGGC                    87
```

( 2 ) INFORMATION FOR SEQ ID NO:225:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:225:

```
GGGAGAUAAG  AAUAAACGCU  CAACGGAGGA  AGGAAGAGGA  GCCUUCGCCU     50

CUGAUUUAGC  UUAUUCGACA  GGAGGCUCAC  AACAGGC                    87
```

( 2 ) INFORMATION FOR SEQ ID NO:226:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:226:

```
GGGAGAUAAG  AAUAAACGCU  CAACGAGGCC  ACCGACAAGG  AAGUCGACCG     50

GAGUUGAAGU  AAAUUCGACA  GGAGGCUCAC  AACAGGC                    87
```

( 2 ) INFORMATION FOR SEQ ID NO:227:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:227:

```
GGGAGAUAAG  AAUAAACGCU  CAAGGCCCCU  AGCGGGAUGC  CGCUAAUCGC     50

GAAUCGAGGU  UUAUUCGACA  GGAGGCUCAC  AACAGGC                    87
```

( 2 ) INFORMATION FOR SEQ ID NO:228:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:

( D ) OTHER INFORMATION: All U's are 2'-F uracil ( x i ) SEQUENCE DESCRIPTION: SEQ ID NO:228:

| GGGAGAUAAG | AAUAAACGCU | CAAUCGAUGC | UAUCGAGUUC | UACUCGGAAG | 50 |
| GUUCAACGUU | UAAUUCGACA | GGAGGCUCAC | AACAGGC | | 87 |

( 2 ) INFORMATION FOR SEQ ID NO:229:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:229:

| GGGAGAUAAG | AAUAAACGCU | CAACCCAUAC | UGAGAAAGAA | CAGACUUCUC | 50 |
| AGGUUCGAAC | GUUUCGACAG | GAGGCUCACA | ACAGGC | | 86 |

( 2 ) INFORMATION FOR SEQ ID NO:230:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:230:

| GGGAGAUAAG | AAUAAACGCU | CAACCUGAGA | CGGUACGAGU | UCGGACUCAG | 50 |
| GAUUUAACGC | UUUUUCGACA | GGAGGCUCAC | AACAGGC | | 87 |

( 2 ) INFORMATION FOR SEQ ID NO:231:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F cytosine ( i x ) FEATURE:
        ( D ) OTHER INFORMATION: All U's are 2'-F uracil ( x i ) SEQUENCE DESCRIPTION: SEQ ID NO:231:

| GGGAGAUAAG | AAUAAACGCU | CAACUUACUC | AACCUGCGAA | CGCACAGGUU | 50 |
| AGUUCACCGU | UUAUUCGACA | GGAGGCUCAC | AACAGGC | | 87 |

( 2 ) INFORMATION FOR SEQ ID NO:232:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:232:

```
GGGAGAUAAG AAUAAACGCU CAAACCCACA CUGAGAAAGA ACAGACUCCA      50

CAGGUUCGAA CGUUUCGACA GGAGGCUCAC AACAGGC                   87
```

( 2 ) INFORMATION FOR SEQ ID NO:233:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:233:

```
GGGAGAUAAG AAUAAACGCU CAAAAACUCA UUCUGAGCUA AGCUCAAGUU      50

CUUGCAACGU UUGUUCGACA GGAGGCUCAC AACAGGC                   87
```

( 2 ) INFORMATION FOR SEQ ID NO:234:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:234:

```
GGGAGAUAAG AAUAAACGCU CAAACCGAUU CUCGAAGCAG CACGCUCCAG      50

GUCUGACGUU UUUUCGACAG GAGGCUCACA ACAGGC                    86
```

( 2 ) INFORMATION FOR SEQ ID NO:235:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F cytosine ( i x ) FEATURE:
    ( D ) OTHER INFORMATION: All U's are 2'-F uracil ( x i ) SEQUENCE DESCRIPTION: SEQ ID NO:235:

```
GGGAGAUAAG AAUAAACGCU CAAACCUAUA CUGAGAAAGA ACAGACUUCU      50

CAGGUUCGAA CGUUUCGACA GGAGGCUCAC AACAGGC                   87
```

( 2 ) INFORMATION FOR SEQ ID NO:236:

( i ) SEQUENCE CHARACTERISTICS:
    ( A ) LENGTH: 87 base pairs

- continued ( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:236:

GGGAGAUAAG AAUAAACGCU CAAAGGAACU UAUUCGACAU CAGUCGGUUC 50

CCUGGACGGG UUGUUCGACA GGAGGCUCAC AACAGGC 87

( 2 ) INFORMATION FOR SEQ ID NO:237:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:237:

GGGAGAUAAG AAUAAACGCU CAAGAACCUA UUCAACCGGA UUAGGUUGGU 50

UCUCGGAUGU CUAUUCGACA GGAGGCUCAC AACAGGC 87

( 2 ) INFORMATION FOR SEQ ID NO:238:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:238:

GACCUUCGUU UGACGCUCAU UCGACAGGAG GCUCACAACA GG 42

( 2 ) INFORMATION FOR SEQ ID NO:239:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F cytosine ( i x ) FEATURE:
( D ) OTHER INFORMATION: All U's are 2'-F uracil ( x i ) SEQUENCE DESCRIPTION: SEQ ID NO:239:

GACCUUCGUU UGACGCUUAU UCGACAGGAG GCUCACAACA GG 42

( 2 ) INFORMATION FOR SEQ ID NO:240:

( i ) SEQUENCE CHARACTERISTICS:
( A ) LENGTH: 46 base pairs (B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:240:

CGUUCGGUCG GUUUGUCCGA UUAUUCGACA GGAGGCUCAC AACAGG    46

(2) INFORMATION FOR SEQ ID NO:241:

(i) SEQUENCE CHARACTERISTICS:
(A) LENGTH: 21 base pairs
(B) TYPE: nucleic acid
(C) STRANDEDNESS: single
(D) TOPOLOGY: linear (ix) FEATURE:
(D) OTHER INFORMATION: All C's are 2'-F cytosine (ix) FEATURE:
(D) OTHER INFORMATION: All U's are 2'-F uracil (xi) SEQUENCE DESCRIPTION: SEQ ID NO:241:

GUCGUUUGUU CGACAGGAGG C    21